(12) United States Patent
Chow et al.

(10) Patent No.: US 7,998,112 B2
(45) Date of Patent: Aug. 16, 2011

(54) DEFLECTABLE CATHETER ASSEMBLY AND METHOD OF MAKING SAME

(75) Inventors: Mina Chow, Campbell, CA (US); Barbara Stramberg, San Jose, CA (US); William E. Webler, Escondido, CA (US); John A. Simpson, Carlsbad, CA (US); August R. Yambao, Temecula, CA (US); Gabriel F. Asongwe, San Jose, CA (US); Jessica G. Chiu, Belmont, CA (US); Lili Liu, St. Paul, MN (US); Dagmar Beyerlein, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1146 days.

(21) Appl. No.: 10/676,616

(22) Filed: Sep. 30, 2003

(65) Prior Publication Data
US 2005/0070844 A1    Mar. 31, 2005

(51) Int. Cl.
*A61M 31/00* (2006.01)
(52) U.S. Cl. .................... 604/93.01; 604/95.04; 604/528
(58) Field of Classification Search ............... 604/93.01, 604/528, 264, 200, 202, 95.04, 96.01, 523–284, 604/164.01–170.03
See application file for complete search history.

(56) References Cited

U.S. PATENT DOCUMENTS

| | | |
|---|---|---|
| 3,177,543 A | 11/1962 | Fountain |
| 3,716,058 A | 2/1973 | Tanner, Jr. |
| 4,128,100 A | 12/1978 | Wendorff |
| 4,719,924 A | 1/1988 | Crittenden et al. |
| 4,781,186 A | 11/1988 | Simpson et al. |
| 4,817,250 A | 4/1989 | Kurosaki |
| 4,830,023 A | 5/1989 | de Toledo et al. |
| 4,920,980 A | 5/1990 | Jackowski |
| 4,927,421 A | 5/1990 | Goble et al. |
| 4,994,067 A | 2/1991 | Summers |
| 5,040,548 A | 8/1991 | Yock |
| 5,061,273 A | 10/1991 | Yock |
| 5,100,418 A | 3/1992 | Yoon et al. |
| 5,100,421 A | 3/1992 | Christoudias |

(Continued)

FOREIGN PATENT DOCUMENTS

DE    10161543    6/2003

(Continued)

OTHER PUBLICATIONS

PCT International Preliminary Report on Patentability and Written Opinion for PCT Appln. No. US2004/031403, mailed Apr. 13, 2006 (8 pages).

(Continued)

*Primary Examiner* — Kevin C Sirmons
*Assistant Examiner* — Phillip Gray
(74) *Attorney, Agent, or Firm* — Blakely Sokoloff Taylor & Zafman LLP

(57) ABSTRACT

A deflectable catheter assembly is disclosed. The assembly comprises a catheter shaft having a catheter proximal section and a catheter distal section, and at least one lumen extending therethrough. The catheter distal section is more flexible than the catheter proximal section. A tendon is disposed within a first lumen of said catheter shaft. The first lumen is approximately centrally located within the catheter shaft at the catheter proximal section. The first lumen is located off-center of the catheter shaft at the catheter distal section. The tendon is able to deflect the catheter distal section when being pulled on. A catheter handle is coupled to the catheter shaft at the catheter proximal section, the catheter handle includes a control mechanism to control the tendon.

29 Claims, 42 Drawing Sheets

U.S. PATENT DOCUMENTS

| | | | |
|---|---|---|---|
| 5,102,421 A | 4/1992 | Anspach, Jr. | |
| 5,116,337 A | 5/1992 | Johnson | |
| 5,129,902 A | 7/1992 | Goble et al. | |
| 5,141,520 A | 8/1992 | Goble et al. | |
| 5,156,616 A | 10/1992 | Meadows et al. | |
| 5,171,233 A | 12/1992 | Amplatz et al. | |
| 5,201,598 A | 4/1993 | Tehan | |
| 5,234,443 A | 8/1993 | Phan et al. | |
| 5,242,456 A | 9/1993 | Nash et al. | |
| 5,246,441 A | 9/1993 | Ross et al. | |
| 5,350,395 A | 9/1994 | Yock | |
| 5,358,479 A | 10/1994 | Wilson | |
| 5,370,662 A | 12/1994 | Stone et al. | |
| 5,374,275 A | 12/1994 | Bradley et al. | |
| 5,383,260 A | 1/1995 | Deschenes et al. | |
| 5,431,673 A | 7/1995 | Summers et al. | |
| 5,441,483 A | 8/1995 | Avitall | |
| 5,441,499 A * | 8/1995 | Fritzsch | 606/45 |
| 5,451,233 A | 9/1995 | Yock | |
| 5,456,667 A * | 10/1995 | Ham et al. | 604/107 |
| 5,487,757 A | 1/1996 | Truckai et al. | |
| 5,495,974 A | 3/1996 | Deschenes et al. | |
| 5,518,162 A | 5/1996 | Deschenes et al. | |
| 5,522,873 A | 6/1996 | Jackman et al. | |
| 5,531,686 A | 7/1996 | Lundquist et al. | |
| 5,554,184 A | 9/1996 | Machiraju | |
| 5,569,277 A | 10/1996 | Evans et al. | |
| 5,571,215 A | 11/1996 | Sterman et al. | |
| 5,588,188 A | 12/1996 | Jermyn, Jr. | |
| 5,609,598 A | 3/1997 | Laufer et al. | |
| 5,613,937 A | 3/1997 | Garrison et al. | |
| 5,617,854 A | 4/1997 | Munsif | |
| 5,626,613 A | 5/1997 | Schmieding | |
| 5,632,754 A | 5/1997 | Farley et al. | |
| 5,640,955 A | 6/1997 | Ockuly et al. | |
| 5,642,736 A | 7/1997 | Avitall | |
| 5,681,280 A | 10/1997 | Rusk et al. | |
| 5,681,346 A | 10/1997 | Orth et al. | |
| 5,682,906 A | 11/1997 | Sterman et al. | |
| 5,687,723 A | 11/1997 | Avitall | |
| 5,728,129 A | 3/1998 | Summers | |
| 5,782,828 A | 7/1998 | Chen et al. | |
| 5,810,882 A | 9/1998 | Bolduc et al. | |
| 5,823,955 A | 10/1998 | Kuck et al. | |
| 5,824,008 A | 10/1998 | Bolduc et al. | |
| 5,865,800 A | 2/1999 | Mirarchi et al. | |
| 5,868,733 A | 2/1999 | Ockuly et al. | |
| 5,868,767 A | 2/1999 | Farley et al. | |
| 5,916,213 A | 6/1999 | Haissaguerre et al. | |
| 5,954,731 A | 9/1999 | Yoon | |
| 5,961,440 A | 10/1999 | Schweich, Jr. et al. | |
| 5,964,772 A | 10/1999 | Bolduc et al. | |
| 5,972,022 A | 10/1999 | Huxel | |
| 5,989,284 A | 11/1999 | Laufer | |
| 6,001,095 A | 12/1999 | de la Rama et al. | |
| 6,001,104 A | 12/1999 | Benderev et al. | |
| 6,001,127 A | 12/1999 | Schoon et al. | |
| 6,004,332 A | 12/1999 | Yoon et al. | |
| 6,017,358 A | 1/2000 | Yoon et al. | |
| 6,021,340 A | 2/2000 | Randolph et al. | |
| 6,027,514 A | 2/2000 | Stine | |
| 6,036,715 A | 3/2000 | Yock | |
| 6,045,497 A | 4/2000 | Schweich, Jr. et al. | |
| 6,050,936 A | 4/2000 | Schweich, Jr. et al. | |
| 6,051,008 A | 4/2000 | Saadat et al. | |
| 6,059,715 A | 5/2000 | Schweich, Jr. et al. | |
| 6,077,214 A | 6/2000 | Mortier et al. | |
| 6,090,096 A | 7/2000 | St. Goar et al. | |
| 6,093,199 A | 7/2000 | Brown et al. | |
| 6,102,887 A | 8/2000 | Altman | |
| 6,110,100 A | 8/2000 | Talpade | |
| 6,113,609 A | 9/2000 | Adams | |
| 6,117,176 A | 9/2000 | Chen | |
| 6,120,520 A | 9/2000 | Saadat et al. | |
| 6,123,699 A * | 9/2000 | Webster, Jr. | 604/528 |
| 6,149,669 A | 11/2000 | Li | |
| 6,161,543 A | 12/2000 | Cox et al. | |
| 6,162,168 A | 12/2000 | Schweich, Jr. et al. | |
| 6,164,283 A | 12/2000 | Lesh | |
| 6,165,119 A | 12/2000 | Schweich, Jr. et al. | |
| 6,165,120 A | 12/2000 | Schweich, Jr. et al. | |
| 6,165,164 A | 12/2000 | Hill et al. | |
| 6,165,183 A | 12/2000 | Kuehn et al. | |
| 6,165,197 A | 12/2000 | Yock | |
| 6,174,323 B1 | 1/2001 | Biggs et al. | |
| 6,176,240 B1 | 1/2001 | Nikolchev et al. | |
| 6,178,346 B1 | 1/2001 | Amundson et al. | |
| 6,182,664 B1 | 2/2001 | Cosgrove | |
| 6,183,411 B1 | 2/2001 | Mortier et al. | |
| 6,187,040 B1 | 2/2001 | Wright | |
| 6,190,401 B1 | 2/2001 | Green et al. | |
| 6,190,408 B1 | 2/2001 | Melvin | |
| 6,203,531 B1 | 3/2001 | Ockuly et al. | |
| 6,210,407 B1 | 4/2001 | Webster, Jr. | |
| 6,210,432 B1 | 4/2001 | Solem et al. | |
| 6,231,561 B1 | 5/2001 | Frazier et al. | |
| 6,231,587 B1 | 5/2001 | Makower | |
| 6,241,728 B1 | 6/2001 | Gaiser et al. | |
| 6,254,568 B1 | 7/2001 | Ponzi | |
| 6,254,598 B1 * | 7/2001 | Edwards et al. | 606/41 |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,267,781 B1 | 7/2001 | Tu | |
| 6,269,819 B1 | 8/2001 | Oz et al. | |
| 6,270,526 B1 | 8/2001 | Cox | |
| 6,283,127 B1 | 9/2001 | Sterman et al. | |
| 6,283,962 B1 | 9/2001 | Tu et al. | |
| 6,299,622 B1 | 10/2001 | Snow et al. | |
| 6,306,133 B1 | 10/2001 | Tu et al. | |
| 6,312,447 B1 | 11/2001 | Grimes | |
| 6,325,823 B1 | 12/2001 | Horzewski et al. | |
| 6,355,030 B1 | 3/2002 | Aldrich et al. | |
| 6,371,978 B1 | 4/2002 | Wilson | |
| 6,374,476 B1 | 4/2002 | Ponzi et al. | |
| 6,402,780 B2 | 6/2002 | Williamson, IV et al. | |
| 6,402,781 B1 | 6/2002 | Langberg et al. | |
| 6,408,214 B1 | 6/2002 | Williams et al. | |
| 6,419,696 B1 | 7/2002 | Ortiz et al. | |
| 6,461,366 B1 | 10/2002 | Seguin | |
| 6,482,224 B1 | 11/2002 | Michler et al. | |
| 6,488,689 B1 | 12/2002 | Kaplan et al. | |
| 6,493,575 B1 | 12/2002 | Kesten et al. | |
| 6,497,707 B1 | 12/2002 | Bowman et al. | |
| 6,500,167 B1 | 12/2002 | Webster, Jr. | |
| 6,517,553 B2 | 2/2003 | Klein et al. | |
| 6,537,198 B1 | 3/2003 | Vidlund et al. | |
| 6,537,314 B2 | 3/2003 | Langberg et al. | |
| 6,551,271 B2 | 4/2003 | Nguyen | |
| 6,554,794 B1 | 4/2003 | Mueller et al. | |
| 6,554,852 B1 | 4/2003 | Oberlander | |
| 6,585,718 B2 | 7/2003 | Hayzelden et al. | |
| 6,599,311 B1 | 7/2003 | Biggs et al. | |
| 6,605,086 B2 | 8/2003 | Hayzelden et al. | |
| 6,610,058 B2 | 8/2003 | Flores | |
| 6,619,291 B2 | 9/2003 | Hlavka et al. | |
| 6,626,899 B2 | 9/2003 | Houser et al. | |
| 6,626,930 B1 | 9/2003 | Allen et al. | |
| 6,629,534 B1 | 10/2003 | St. Goar et al. | |
| 6,638,286 B1 | 10/2003 | Burbank et al. | |
| 6,648,903 B1 | 11/2003 | Pierson, III | |
| 6,656,221 B2 | 12/2003 | Taylor et al. | |
| 6,676,702 B2 | 1/2004 | Mathis | |
| 6,706,065 B2 | 3/2004 | Langberg et al. | |
| 6,709,442 B2 | 3/2004 | Miller et al. | |
| 6,709,456 B2 | 3/2004 | Langberg et al. | |
| 6,712,804 B2 | 3/2004 | Roue et al. | |
| 6,718,985 B2 | 4/2004 | Hlavka et al. | |
| 6,719,767 B1 | 4/2004 | Kimblad | |
| 6,723,038 B1 | 4/2004 | Schroeder | |
| 6,733,500 B2 | 5/2004 | Kelley et al. | |
| 6,746,472 B2 | 6/2004 | Frazier et al. | |
| 6,755,812 B2 | 6/2004 | Peterson et al. | |
| 6,761,734 B2 | 7/2004 | Suhr | |
| 6,764,510 B2 | 7/2004 | Vidlund et al. | |
| 6,770,070 B1 * | 8/2004 | Balbierz | 606/41 |
| 6,790,231 B2 | 9/2004 | Liddicoat et al. | |

| | | |
|---|---|---|
| 6,800,090 B2 | 10/2004 | Alferness et al. |
| 6,810,882 B2 | 11/2004 | Langberg |
| 6,824,562 B2 | 11/2004 | Mathis et al. |
| 6,852,124 B2 | 2/2005 | Cox et al. |
| 6,890,353 B2 | 5/2005 | Cohn et al. |
| 6,905,476 B2 | 6/2005 | Ponzi |
| 6,908,478 B2 | 6/2005 | Alferness et al. |
| 6,911,035 B1 | 6/2005 | Blomme |
| 6,951,549 B1 | 10/2005 | Beyerlein |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinski et al. |
| 6,997,951 B2 | 2/2006 | Solem et al. |
| 7,073,504 B2 | 7/2006 | Callister et al. |
| 7,087,064 B1 | 8/2006 | Hyde |
| 7,104,999 B2 | 9/2006 | Overaker |
| 7,160,318 B2 | 1/2007 | Greenberg et al. |
| 7,186,264 B2 | 3/2007 | Liddicoat et al. |
| 7,247,149 B2 | 7/2007 | Beyerlein |
| 7,364,567 B2 | 4/2008 | Beyerlein |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0027322 A1 | 10/2001 | Bowman |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0077647 A1 | 6/2002 | Snow et al. |
| 2002/0087169 A1 | 7/2002 | Brock et al. |
| 2002/0087173 A1 | 7/2002 | Alferness et al. |
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0169502 A1 | 11/2002 | Mathis |
| 2002/0169504 A1 | 11/2002 | Alferness |
| 2002/0183836 A1 | 12/2002 | Liddicoat et al. |
| 2002/0183837 A1 | 12/2002 | Streeter et al. |
| 2002/0183841 A1 | 12/2002 | Cohn et al. |
| 2002/0188170 A1 | 12/2002 | Santamore et al. |
| 2003/0050598 A1 | 3/2003 | Hayzelden |
| 2003/0069593 A1 | 4/2003 | Tremulis et al. |
| 2003/0078465 A1 | 4/2003 | Pai et al. |
| 2003/0083538 A1 | 5/2003 | Adams et al. |
| 2003/0093071 A1 | 5/2003 | Hauck et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130731 A1 | 7/2003 | Vidlund et al. |
| 2003/0144697 A1 | 7/2003 | Mathis |
| 2003/0144732 A1 | 7/2003 | Cosgrove et al. |
| 2003/0167071 A1 | 9/2003 | Martin et al. |
| 2003/0171776 A1 | 9/2003 | Adams et al. |
| 2003/0212453 A1 | 11/2003 | Mathis et al. |
| 2003/0216764 A1 | 11/2003 | Tu et al. |
| 2004/0010231 A1 | 1/2004 | Leonhardt et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0059351 A1 | 3/2004 | Eigler et al. |
| 2004/0098092 A1 | 5/2004 | Butaric et al. |
| 2004/0138683 A1 | 7/2004 | Shelton et al. |
| 2004/0138744 A1 | 7/2004 | Lashinski et al. |
| 2004/0148020 A1 | 7/2004 | Vidlund et al. |
| 2004/0153147 A1 | 8/2004 | Mathis |
| 2005/0045183 A1 | 3/2005 | Callister et al. |
| 2005/0055089 A1 | 3/2005 | Macoviak et al. |
| 2005/0085844 A1 | 4/2005 | Tremulis et al. |
| 2005/0209633 A1 | 9/2005 | Callister et al. |
| 2005/0267571 A1 | 12/2005 | Spence et al. |
| 2005/0267573 A9 | 12/2005 | Macoviak et al. |
| 2006/0041306 A1 | 2/2006 | Vidlund et al. |
| 2006/0095025 A1 | 5/2006 | Levine et al. |

FOREIGN PATENT DOCUMENTS

| | | |
|---|---|---|
| EP | 0 377 269 A | 7/1990 |
| EP | 0980693 | 2/2000 |
| JP | 5329216 | 12/1993 |
| WO | WO-9111213 | 8/1991 |
| WO | WO-9503843 | 2/1995 |
| WO | PCT-WO 98/29041 A1 | 7/1998 |
| WO | WO 99/00059 | 1/1999 |
| WO | WO 99/13777 | 3/1999 |
| WO | PCT-WO 99/30647 A1 | 6/1999 |
| WO | PCT-WO 99/44534 A1 | 9/1999 |
| WO | WO 00/03759 | 1/2000 |
| WO | PCT-WO 00/06026 A2 | 2/2000 |
| WO | PCT-WO 00/06028 A1 | 2/2000 |
| WO | PCT-WO 00/66027 A2 | 2/2000 |
| WO | WO-0006027 | 2/2000 |
| WO | WO-0009185 | 2/2000 |
| WO | PCT-WO 00/16700 A1 | 3/2000 |
| WO | WO 00/60995 | 10/2000 |
| WO | WO 01/00111 A1 | 1/2001 |
| WO | WO 01/00114 A1 | 1/2001 |
| WO | PCT-WO 01/28455 A1 | 4/2001 |
| WO | WO 01/26557 A1 | 4/2001 |
| WO | WO 01/28432 A1 | 4/2001 |
| WO | WO 01/49213 A2 | 7/2001 |
| WO | WO 01/49213 A3 | 7/2001 |
| WO | WO 01/54618 A1 | 8/2001 |
| WO | WO 01/89440 A2 | 11/2001 |
| WO | WO 02/00099 A2 | 1/2002 |
| WO | WO 02/01999 A2 | 1/2002 |
| WO | WO 02/34167 A2 | 5/2002 |
| WO | WO 02/39925 A2 | 5/2002 |
| WO | WO 02/053206 A2 | 7/2002 |
| WO | WO 02/060352 | 8/2002 |
| WO | WO 02/062263 A2 | 8/2002 |
| WO | WO 02/062270 A1 | 8/2002 |
| WO | WO 02/062408 A2 | 8/2002 |
| WO | WO-02063533 | 8/2002 |
| WO | WO-02078576 | 10/2002 |
| WO | WO 03/049619 A2 | 6/2003 |
| WO | WO 03/073913 A2 | 9/2003 |
| WO | WO 04/012789 A2 | 2/2004 |
| WO | WO 04/014282 A2 | 2/2004 |

OTHER PUBLICATIONS

"PCT International Search Report and Written Opinion of the International Searching Authority" for PCT International Appln No. US2004/031403, mailed May 18, 2005 (14 pages).

PCT International Search Report for PCT Application No. US2004/031403. Mailed on Feb. 15, 2005 (5 Pages).

Messas, et al., "Chordal Cutting a New Therapeutic Approach for Ischmic Mitral Regurgitaion," 2001, American Heart Association Inc., pp. 1958-1963.

Bonow, Robert O., et al.; "Guidelines for the Management of Patients with Valvular Health Disease," Report of American College of Cardiology/American Heart Assoc. Task Force on Practice Guidelnes (Committee on Mangement of Pateints with Valvular Heart Disease), American College of Cardiology and American Heart Assoc., Inc., 1998, pp. 1949-1984.

PCT Invitation to Pay Additional fees for PCT International Appln. No. US03/36633, mailed May 19, 2004 (5 pages).

Abbott Cardiovascular Systems, Non final office action dated Feb. 23, 2010 for U.S. Appl. No. 10/464,132.

Abbott Cardiovascular Systems, Office Action dated Jan. 25, 2010 for Japanese Patent Application No. 2006-533979.

Abbott Cardiovascular Systems, Final office action dated Aug. 3, 2010 for U.S. Appl. No. 10/464,132.

Abbott Cardiovascular Systems, European search report dated Feb. 18, 2011 for EP Application No. 10185686.2.

Abbott Cardiovascular Systems, Office Action dated Feb. 7, 2011 for Japanese Patent Application No. 2006-533979.

* cited by examiner

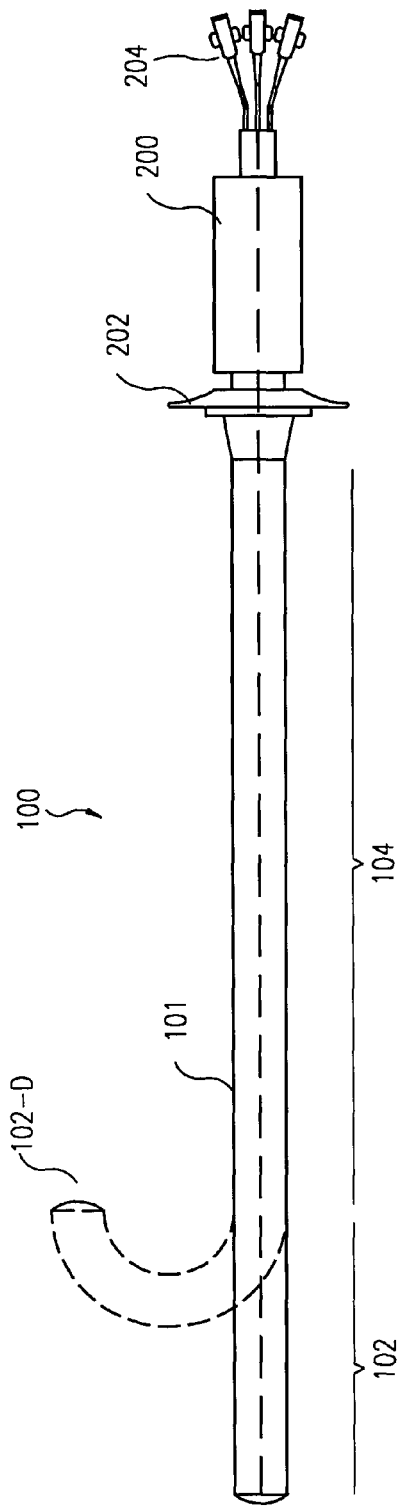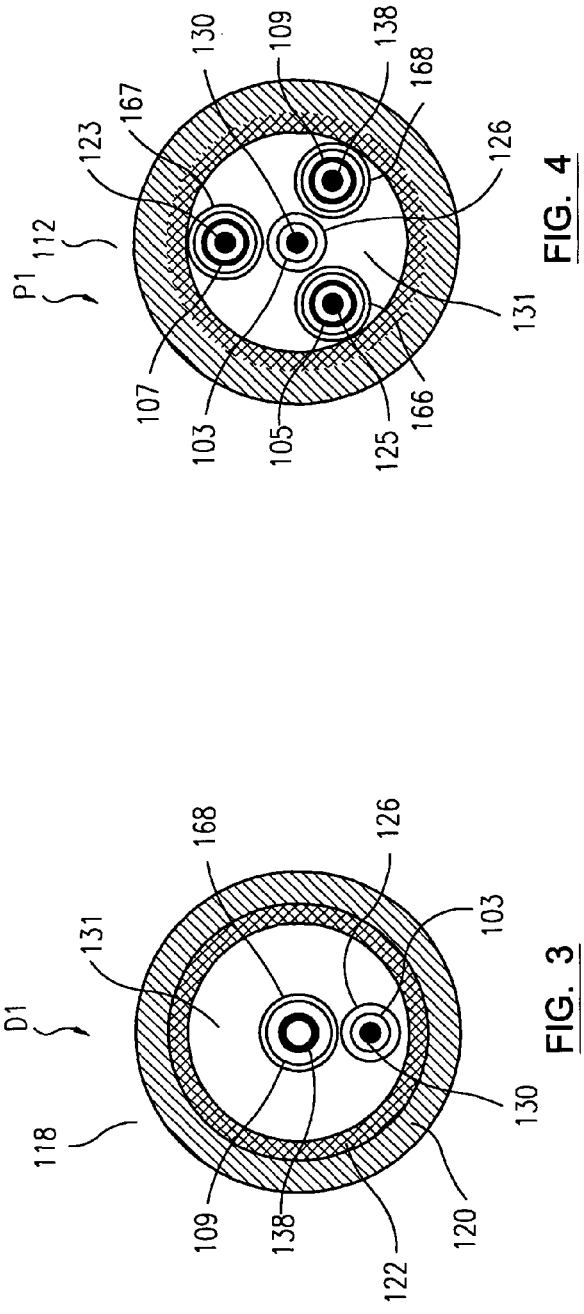

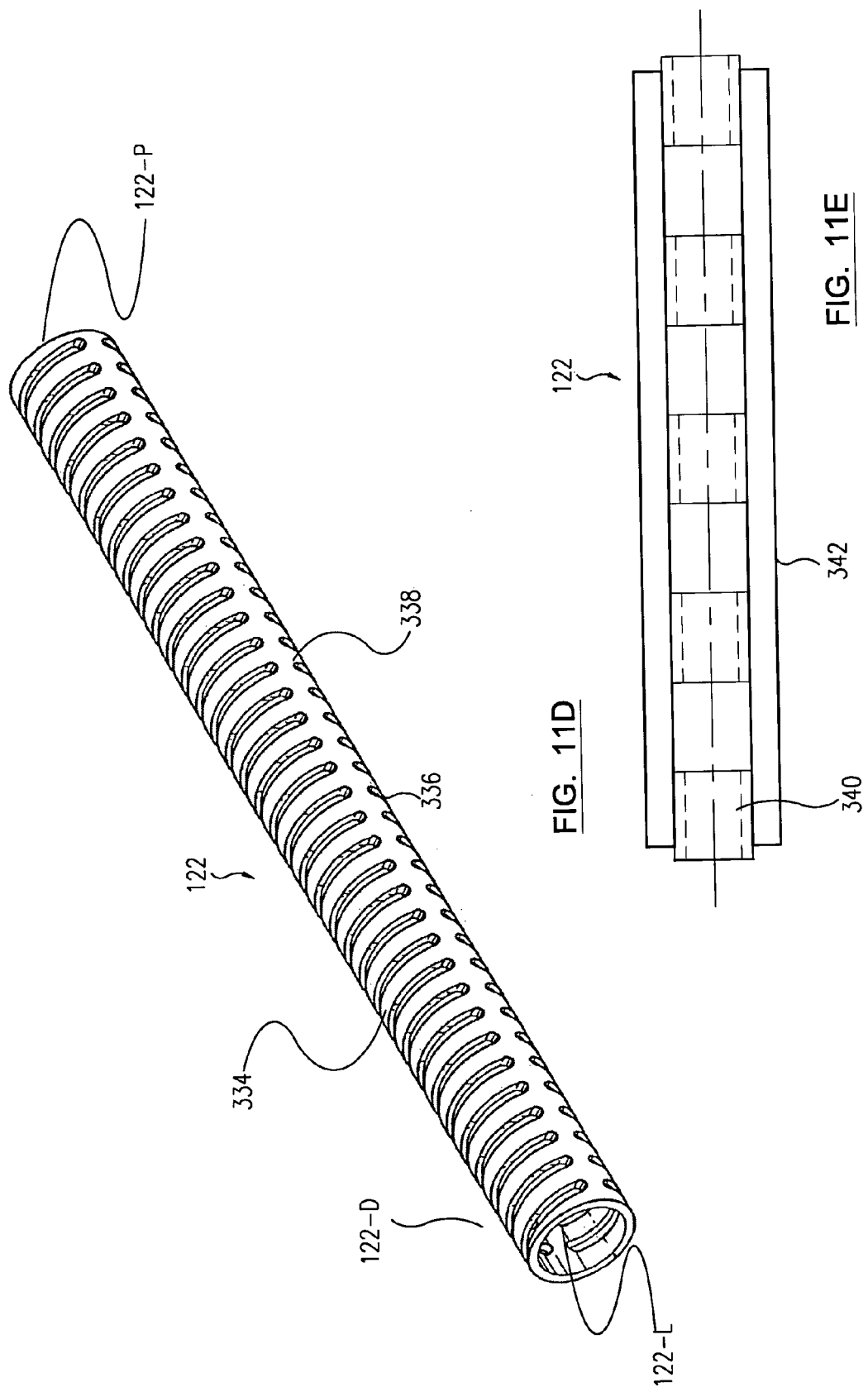

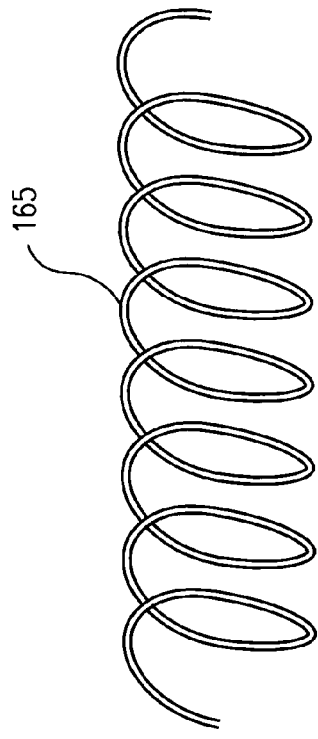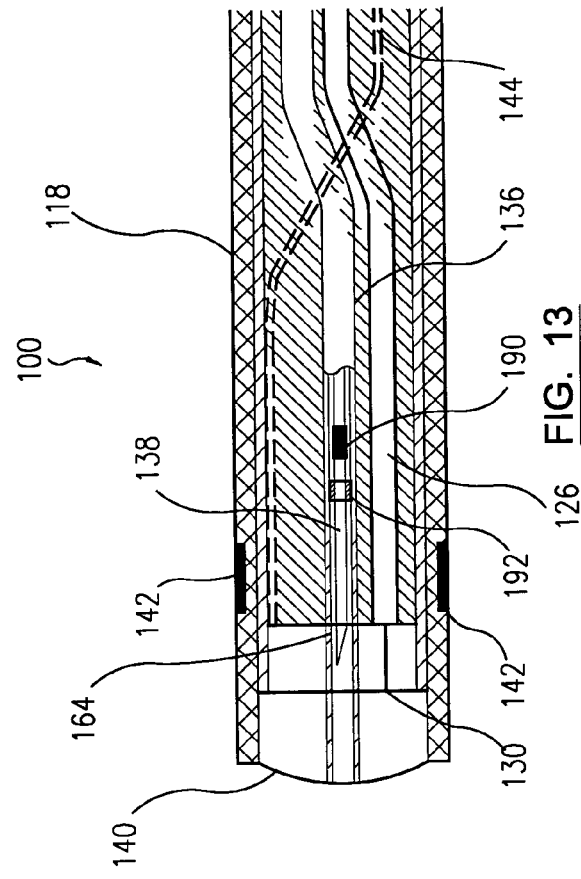

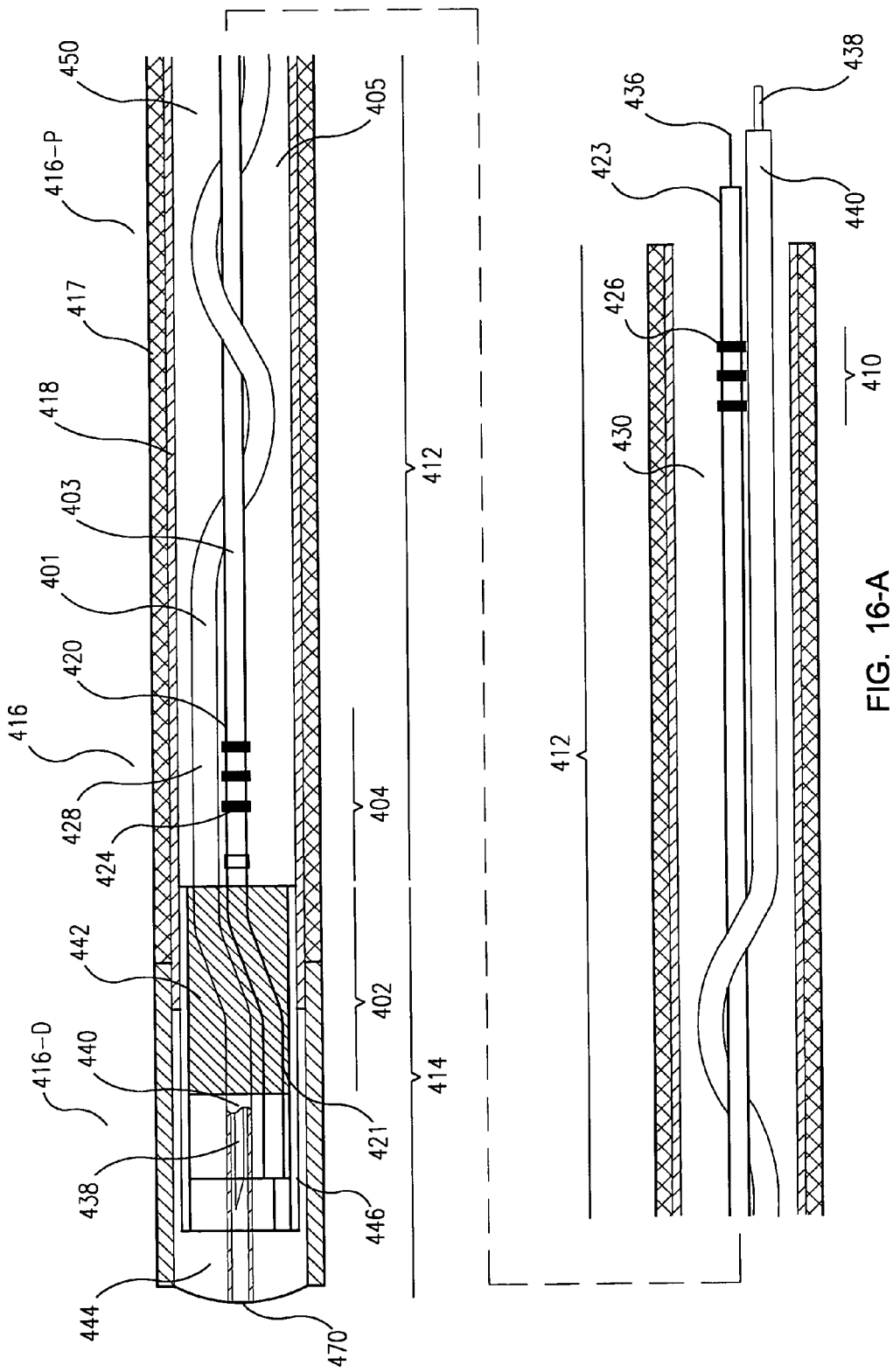
FIG. 16-A

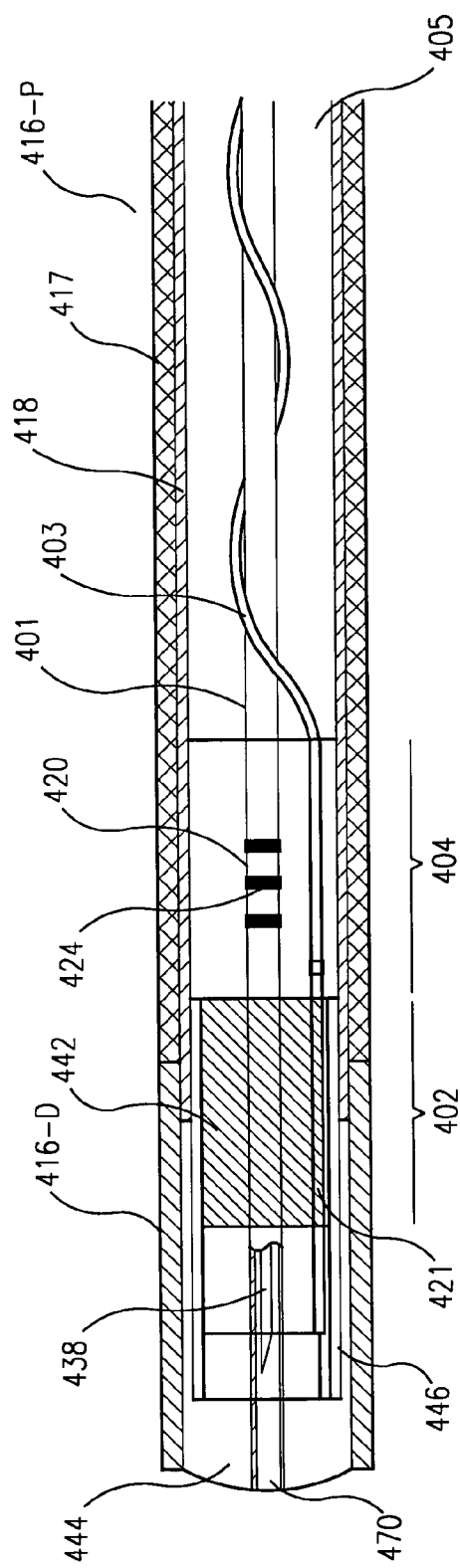
FIG. 16-B
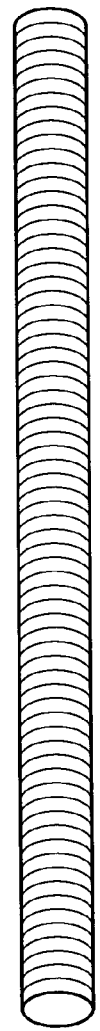
FIG. 17

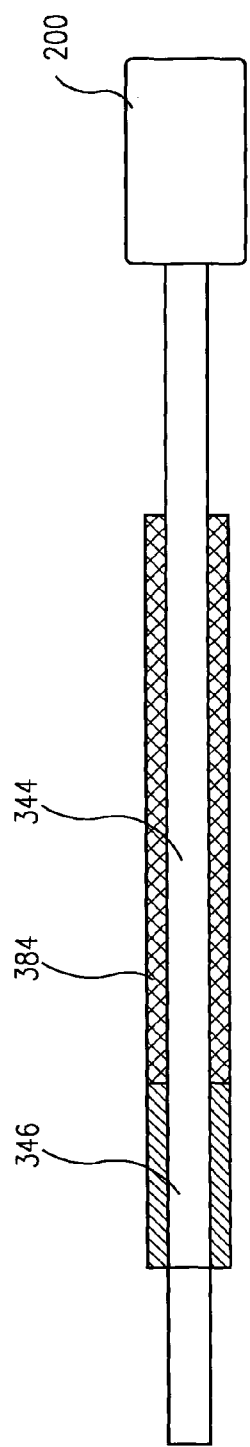
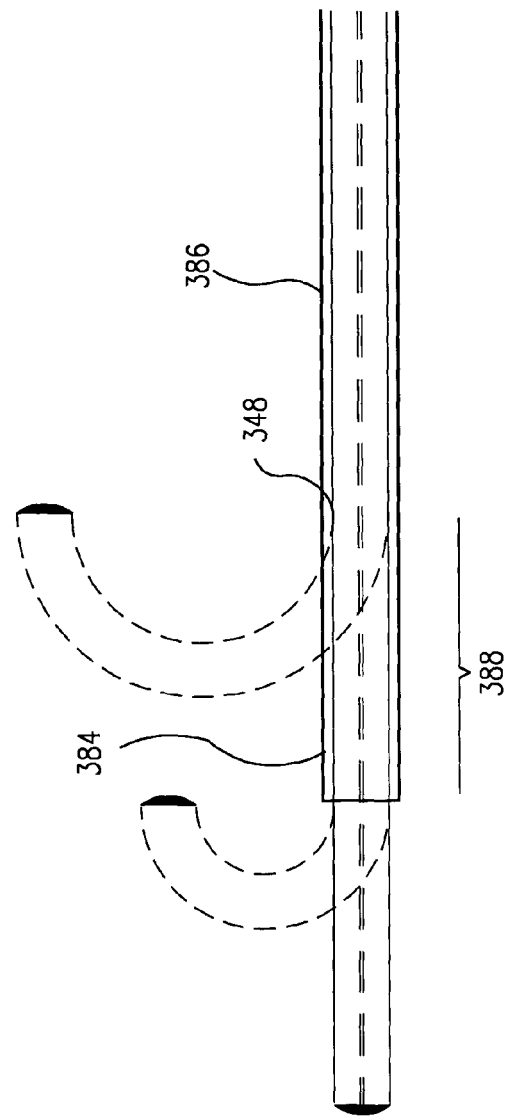
FIG. 27A
FIG. 27B

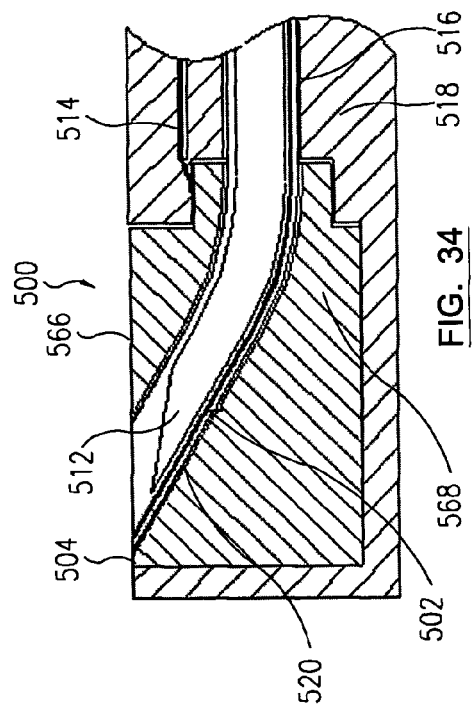
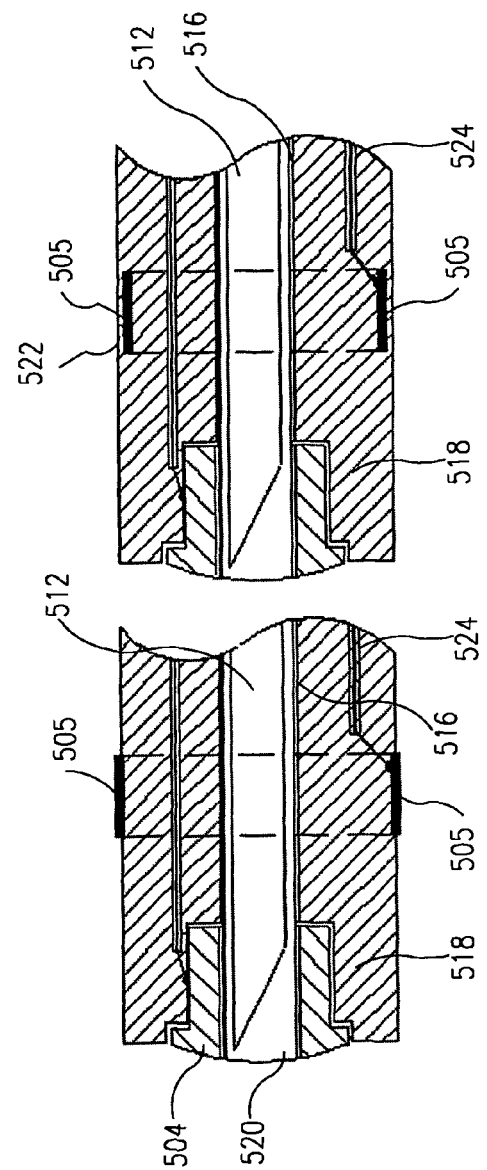

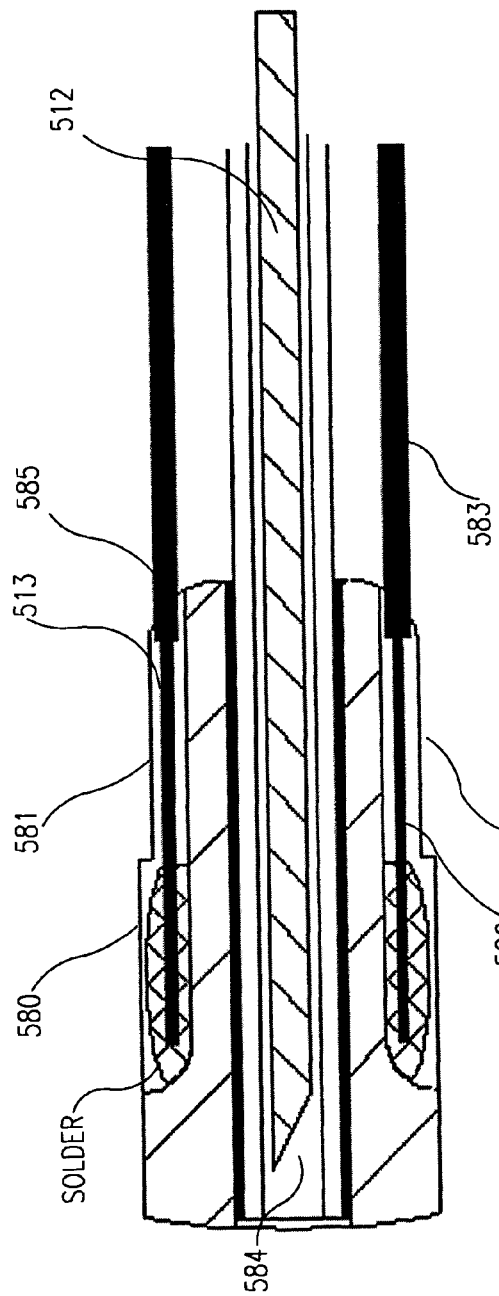
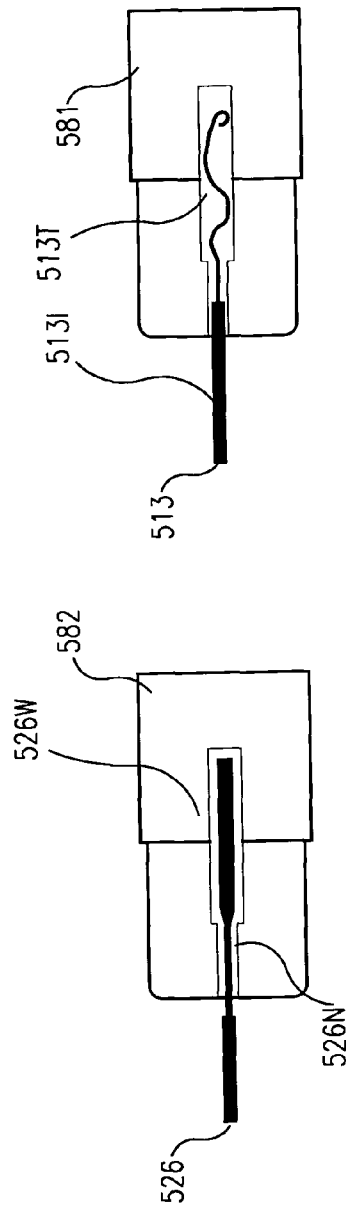
FIG. 35C
FIG. 35D
FIG. 35E

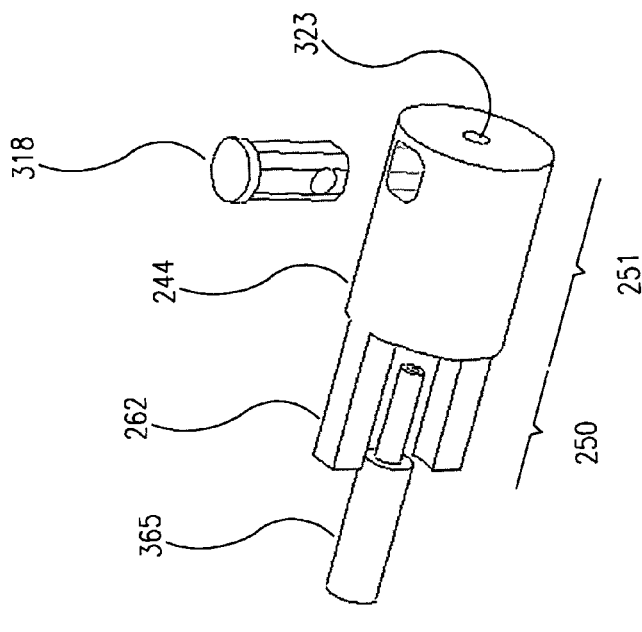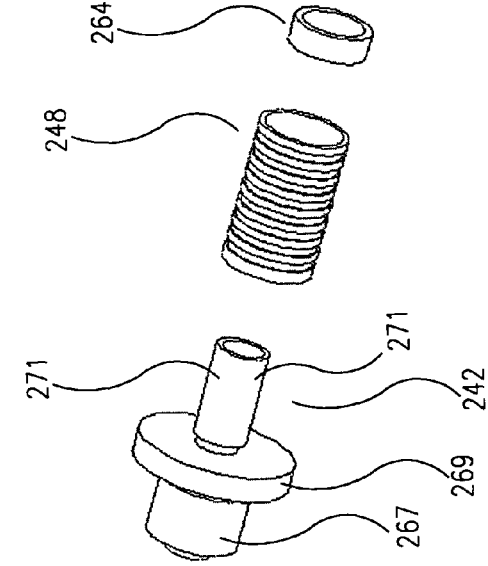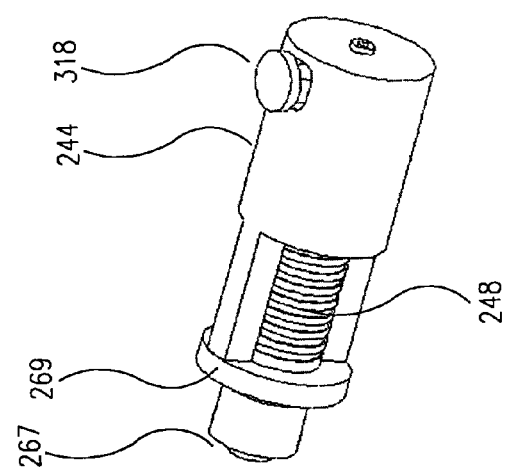
FIG. 39C
FIG. 39D

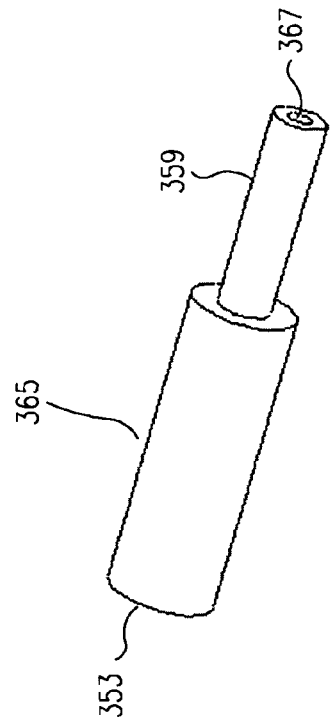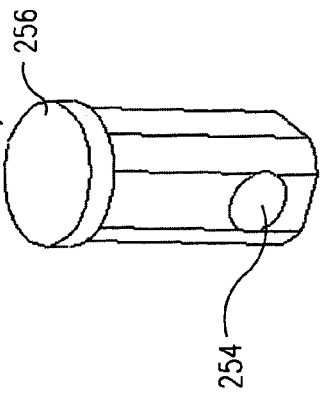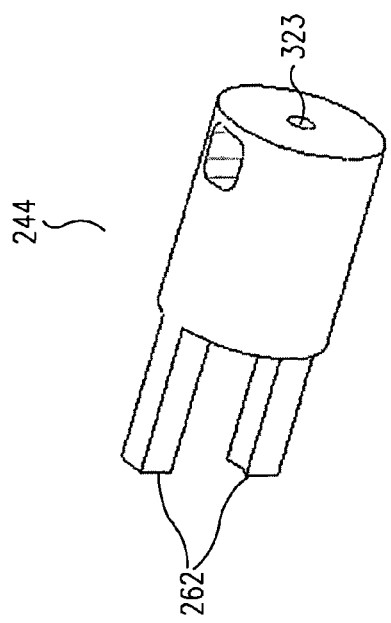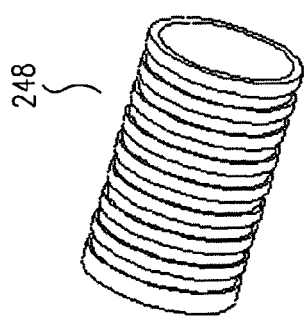
FIG. 39E
FIG. 39F
FIG. 39G
FIG. 39H

DEFLECTABLE CATHETER ASSEMBLY AND METHOD OF MAKING SAME

BACKGROUND

1. Field

Many aspects of this disclosure relate to a deflectable catheter assembly and methods of making and using such deflectable catheter assembly. For example, the catheter assembly of an exemplary embodiment includes a deflectable distal section, a non-deflectable section, a proximal catheter handle, and a tool such as a needle, a therapeutic device, and a diagnostic device.

2. Discussion of Related Art

Steerable catheters have been commonly used in applications such as mapping (e.g., cardiac mapping), drug delivery (e.g., intramyocardial drug delivery), and ablation, (e.g., arrhythmia ablation).

A steerable catheter has a deflectable flexible distal section and a stiffer proximal torqueable shaft. The steerable function is accomplished by three modes of actions: 1) translational catheter movement along the shaft direction, 2) deflection of the distal deflectable section, and 3) turning of the catheter shaft to direct the deflection toward the target therapy site. A tendon wire is included to control the deflection of the distal section. This tendon wire is located inside of a sheath running along and within the catheter shaft with its distal end attached near the distal tip of the catheter. A pulling mechanism is included within the proximal catheter handle, which is coupled to the proximal end of the catheter shaft. The pulling mechanism controls the tendon wire to deflect the distal section of the catheter shaft. Radially, the tendon wire is located off-center of the catheter shaft center to create a moment toward the intended deflection side in the catheter distal deflectable section. When the tendon wire is pulled, the catheter deflects toward the radial direction to which the tendon wire is located. The deflection section is typically made to be much more flexible than the rest of the catheter shaft. When the tendon wire is pulled in tension, the catheter shaft wants to "curl up." The distal section is the most flexible section of the catheter shaft and thus it deflects when the tendon wire is pulled. To direct the deflected section toward the target site, an operator turns the catheter shaft on the proximal end. The deflection section responds to the torque in a fashion that is governed by the way the catheter is constructed.

Depending on the therapeutic use of the catheter, a therapeutic tool, such as a needle, may run in parallel to the tendon wire within the catheter shaft.

One problem commonly occurring in the working of this kind of catheter is that the catheter whips when rotated from the proximal end of the shaft. Whipping is caused by the resistance of the catheter to turn away from its preferred orientation, which is generated by unbalanced stiffness over the cross-section of the catheter shaft. This whipping problem gets further magnified when the catheter distal section is deflected and/or when the catheter is resident in tortuous vasculature.

For example, in a catheter that has a needle running through a central lumen within the catheter shaft, the tendon is placed off-center. As can be imagined, the cross-section of the catheter shaft now has an unbalanced radial cross-section created by the tendon wire in its lumen construction. When the catheter shaft is placed over a curved anatomy section, such as the aortic arch, the stiffer tendon wire section has a tendency to stabilize itself toward the outside of the curve (resulting in the lowest energy state). If one tries to rotate the catheter shaft out of this preferred orientation, with the stiff section turning to the inside of the bending curve, the catheter shaft will resist this turning, requiring an applied torque in excess of that required if the catheter shaft had a balanced stiffness and resulting in an increased amount of shaft torsional distortion (wind-up) and accompanying stored torque in the catheter shaft. As one continues to rotate the catheter shaft just past the point with the stiff section directly at the inside of the bending curve, the resistance to turning is suddenly reduced, because the catheter shaft is returning toward its preferred orientation. The stored torque of the catheter shaft now exceeds that required for turning and the catheter shaft rapidly unwinds its wind-up until they are in balance. From the viewpoint of an operator who is turning the proximal end of the catheter shaft at a relatively constant rate, the distal end of the catheter shaft appears to slowly rotate away from its preferred orientation, then when it gets to 180-degree away from its preferred orientation, it suddenly and uncontrollably speeds up and rotates past an adjacent arc of rotation. This sudden and uncontrollable rotation is referred to as whipping. To attain an orientation in the adjacent arc that the distal end of the catheter shaft rotated past, the proximal end of the catheter shaft is required to be rotated back in the opposite direction. In many cases, it is impossible to get the distal end of the catheter shaft to maintain an orientation in the vicinity of 180-degrees away from its preferred orientation with the rotation of the proximal end of the catheter shaft even if the proximal end of the catheter shaft is rotated in the opposite direction. For an operator that only has control of the catheter's proximal end, whipping makes accurate control of the orientation of the catheter's distal end difficult, time consuming, and often very frustrating.

The whipping problem becomes more pronounced when the tendon is pulled to deflect the distal section. Pulling of the tendon creates compression ("curling up") in the radial side where the tendon locates. Therefore, this compressed side has a preference to reside on the inside of the bending curve. The turning of the catheter shaft now has to work against not just the preferred orientation due to unbalanced stiffness but also against the compression load occurring preferentially on one side of the catheter shaft.

SUMMARY

There is a need for catheter assemblies that can compensate for the unbalanced moment and asymmetric stiffness in deflectable catheter assemblies. Many exemplary embodiments of this disclosure provide deflectable catheter assemblies with components that provide a balanced force distribution and a balanced moment.

In one embodiment, a deflectable catheter assembly comprises a catheter shaft having a catheter proximal section and a catheter distal section, and at least one lumen extending therethrough. The catheter distal section is more flexible than the catheter proximal section. A tendon is disposed within a first lumen of said catheter shaft. The first lumen is approximately centrally located within the catheter shaft at the catheter proximal section. The first lumen is located off-center of the catheter shaft at the catheter distal section. The tendon is able to deflect the catheter distal section when being pulled on. A catheter handle is coupled to the catheter shaft at the catheter proximal section. The catheter handle includes a first control mechanism to control the tendon.

In an alternative embodiment, a needle is included and wrapped around an approximately center tendon to create a balance in the deflectable catheter assembly. The tendon and the needle are disposed within the first lumen of the catheter shaft. The needle is wrapped around the tendon at the catheter proximal section. The tendon may be located in the center of the catheter shaft or located approximately near the center of the catheter shaft at the catheter proximal section. Along the catheter distal section, the tendon is placed so that it is located off-center of the catheter shaft to allow deflection of the catheter distal section and the needle is not wrapped around the tendon. The needle may be brought to the center or approximately at the center of the catheter distal shaft. The catheter handle includes a second control mechanism to control the needle.

In an alternative embodiment, the tendon is wrapped around a needle to create a balance in the deflectable catheter assembly. Along the catheter distal section, the tendon is placed so that it is located off-center of the catheter shaft to allow defection of the catheter distal section and the tendon is not wrapped around the needle.

In an alternative embodiment, a stiffening member is used to allow for adjustment of the deflection length along the catheter distal section. A stiffening member is moveably disposed within a second lumen of the catheter shaft. The second lumen is proximate and parallel to the first lumen, at least at the catheter distal section. The catheter handle includes a third control mechanism to control the stiffening member. The needle and the tendon may or may not be wrapped around each other.

In an alternative embodiment, a stiffening outer sheath is disposed outside the deflectable catheter assembly to allow for adjustment of the deflection length along the catheter distal section. A stiffening outer sheath is moveably disposed around the catheter shaft and extending from catheter proximal section to a point along the catheter distal section that defines the beginning of a deflection point. The catheter handle includes a control mechanism to control the stiffening outer sheath. The needle and the tendon may or may not be wrapped around each other.

In another embodiment, a two tendon-system is used to allow for the deflection of the catheter distal section with various deflection shapes or curvatures. Here, a deflectable catheter assembly comprises a catheter shaft having a catheter proximal section and a catheter distal section, and a plurality of lumens disposed therethrough. The catheter distal section is more flexible than the catheter proximal section. A fixed tendon is disposed within a first lumen of the catheter shaft. The first lumen is located off-center of the catheter shaft and extending along a first section of catheter shaft. The fixed tendon includes a plurality of anchors extending outside of the first lumen. A lateral tendon is disposed within a second lumen of the catheter shaft. The second lumen is located approximately in the center of the catheter shaft at the catheter proximal section and located off-center of the catheter shaft at the catheter distal section. The lateral tendon includes an anchor hook extending outside of the second lumen. The anchor hook is capable of engaging any one of the plurality of anchors, wherein an engagement of the anchor hook to one of the plurality of anchors defines the shape or curvature of the deflection of the catheter distal section. A catheter handle is coupled to the catheter shaft. The catheter handle includes a first control mechanism to control the lateral tendon.

The catheter handle for any one of the exemplary catheter assembly embodiments includes a first control mechanism that moves the tendon. In addition, the catheter handle comprises an inner housing and an outer housing that is moveable relative to each other, wherein the first control mechanism is moveably disposed within the outer housing. The first control mechanism is fixedly attached to the inner housing and coupled to the tendon. Moving the outer housing relative to the inner housing moves the first control mechanism and at least one tendon.

In an alternative embodiment, a multiple-tendon system is used to allow the deflectable catheter to have a deflectable distal section with multiple radial directions of deflection. A plurality of tendons is disposed within the catheter shaft wherein the plurality of tendons is disposed within a first lumen of the catheter shaft. Alternatively, each tendon is disposed within an individual lumen selected from the plurality of lumens. Each tendon is located approximately in the center of the catheter shaft at the catheter proximal section and each tendon is disposed radially off-center of the catheter shaft at the catheter distal section. The plurality of tendons is able to deflect the catheter distal section in multiple radial directions. The catheter handle includes a mechanism to move the plurality of tendons to deflect the catheter distal section wherein the catheter handle enables multiple radial directions of deflection.

In an alternative embodiment, a compression cage is disposed within the distal section of the deflectable catheter assembly to prevent undesirable compression to this section during deflection. The compression cage is sized to fit within the catheter distal section and configured to deflect laterally relative to the centerline of the catheter shaft and to resist axial compression along the centerline.

In an alternative embodiment, the deflectable catheter assembly includes a pressure transducer coupled to the needle to aid in monitoring the penetration depth of the needle.

Other embodiments of the present invention pertain to methods of using the various deflectable catheter assemblies to treat a patient as well as methods of making the various deflectable catheter assemblies.

These and other features and advantages of embodiments of the present invention will be more readily apparent from the detailed description of the embodiments, set forth below, taken in conjunction with the accompanying drawings.

BRIEF DESCRIPTION OF THE DRAWINGS

The present invention is illustrated by way of example and not limitation in the figures of the accompanying drawings, in which like references indicate similar elements and in which:

FIG. 1 illustrates an exemplary embodiment of a deflectable catheter assembly having a catheter distal section that is deflectable by a tendon;

FIG. 3 illustrates a cross-sectional view of the catheter distal section of the catheter assembly illustrated in FIG. 2;

FIG. 4 illustrates a cross-sectional view of the catheter assembly illustrated in FIG. 2 along the catheter proximal section;

FIGS. 11A-11E illustrate various configurations of a compression cage that can be used to resist compression of the catheter distal section of a deflectable catheter assembly;

FIG. 12 illustrates a helical coil structure that can resist the compression of the catheter shaft distal section;

FIG. 13 illustrates an exemplary catheter assembly that includes a needle disposed therethrough and a needle stop mechanism that can control the travel distance of the needle;

FIG. 16A illustrates a catheter assembly having a central tendon and at least one needle wrapped around the central tendon to provide balance to the catheter assembly;

FIG. 16B illustrates a catheter assembly having a central needle and a tendon wrapped around the central needle to provide balance to the catheter assembly;

FIG. 17 illustrates a stacked coil structure that can be used with a tendon assembly of a catheter assembly;

FIGS. 27A-27B illustrate a stiffening outer sheath that can be incorporated into a catheter assembly to provide multiple deflection points to the catheter distal section;

FIGS. 32-34, 35A-35H, 36A-36B, and 37A-37B illustrate various configurations of an electrode system that can be incorporated into a catheter assembly;

FIGS. 39A-39H illustrates a needle extension control that can be coupled to a catheter handle;

FIGS. 53A-53B illustrate exemplary catheter assembly that incorporates a pressure sensor system to detect needle penetration depths.

The features of the described embodiments are specifically set forth in the appended claims. The embodiments are best understood by referring to the following description and accompanying drawings, in which similar parts are identified by like reference numerals.

DETAILED DESCRIPTION

Figure 2:
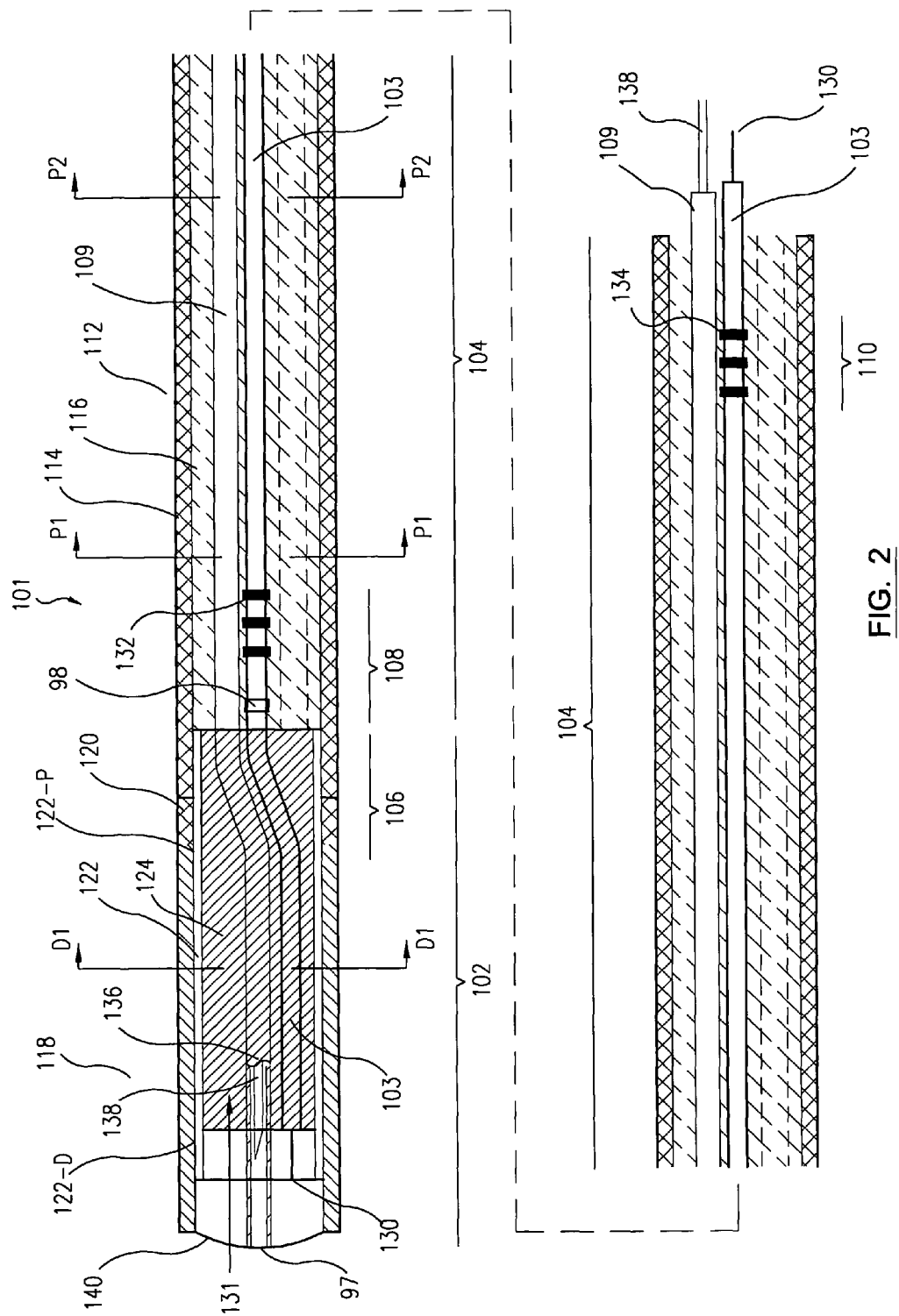
FIG. 2 illustrates a deflectable catheter assembly with the tendon being placed in the center along the catheter proximal section and brought to the side at the catheter distal section.

Many aspects of this disclosure relate to a deflectable catheter assembly and methods of making and using such deflectable catheter assembly. For example, one aspect of this disclosure relates to a needle injection catheter assembly, for delivery of a biologic agent into the wall tissue of the heart, which includes an injection needle, a catheter shaft that includes a deflectable distal section, and a torque-transmitting shaft, and a proximal catheter handle. The catheter shaft is constructed in such a way that it balances moments and length variations commonly occurring in the operation of steerable catheters of this kind. This results in a catheter with superior rotation control and responses.

In the following description, for purposes of explanation, numerous specific details are set forth in order to provide a thorough understanding of the exemplary embodiments of the present invention. It will be evident, however, to one skilled in the art, that these embodiments may be practiced without these specific details. In other instances, specific structures and methods have not been described so as not to obscure the present invention. The following description and drawings are illustrative of the invention and are not to be construed as limiting the invention.

FIG. 1 illustrates one exemplary embodiment of a deflectable catheter assembly 100 that comprises an elongated catheter shaft 101 having a catheter proximal section 104 and a catheter distal section 102. The catheter proximal section 104 may be further divided into two sections, a middle section 104' and a proximal section 104. Each section is constructed with different stiffness to optimize the performance of the catheter shaft 101. In one embodiment, the catheter distal section 102 is more flexible than the catheter proximal section 104. In the embodiment where the catheter proximal section 104 is divided into two sections, the middle section 104' is more flexible than the proximal section 104. Thus, the catheter distal section 102 is the most flexible section followed by the middle section 104'. The catheter proximal section 104 is the least flexible section of the catheter shaft 101. The middle section 104' and the proximal section 104 are used to transmit torque while the distal section 102 does the deflection for the catheter assembly 100.

At least one tendon (see below) is disposed within the catheter shaft 101 to deflect the catheter distal section 102. As shown in FIG. 1, when deflected, the catheter distal section 102 curls up to become a deflected section 102-D. A catheter handle 200 having a deflection control 202 is coupled to the catheter shaft 101 at the catheter proximal section 104. The catheter handle 200 includes a control mechanism (see below) to control the tendon that deflects the catheter distal section 102. At least one therapeutic tool such as a needle (see below) is disposed within the catheter shaft 101. A plurality of connection ports 204 is provided at the catheter handle 200 that allows for necessary communication or connection to the therapeutic tool disposed within the catheter shaft 101. In some embodiments, only one therapeutic tool such as a needle is disposed within the catheter shaft 101. Other therapeutic tool such as an optical fiber bundle emitting light energy for therapies such as photodynamic therapy or a channeling tool to perform transmyocaridal revascularization can also be included in place of the needle or in addition to the needle. In those embodiments, only one connection port 204 is provided at the catheter handle 200.

FIG. 2 illustrates a side view of the catheter shaft 101 of the catheter assembly 100. The catheter shaft 101 includes a tendon assembly 103, which includes a tendon 130 and a needle assembly 109, which includes a needle 138. The tendon assembly 103 and the needle assembly 109 are disposed within a central lumen 131 and extend continuously from the catheter distal section 102 to the catheter proximal section 104. At the catheter proximal section 104, the tendon assembly 103 is located in the center (or approximately in the center) and the needle assembly 109 is located off-center of the catheter shaft 101. It is to be appreciated that the catheter assembly 100 may include more than one needle assembly. Alternatively, other therapeutic or diagnostic tools may replace the needle assembly 109 or may be included in addition to the needle assembly 109. Other therapeutic tool such as an optical fiber bundle emitting light energy for therapies such as photodynamic therapy or a channeling tool to perform transmyocaridal revascularization can also be included in place of the needle or in addition to the needle assembly 109.

In one embodiment, each of the tendon assembly 103 and the needle assembly 109 is disposed within a lumen provided within the central lumen 131 of the catheter shaft 101 (FIGS. 3-4). The tendon assembly 103 is disposed within a tendon lumen 126 and the needle assembly 109 is disposed within a lumen 168.

FIG. 3 shows a cross-section D1 of the distal catheter shaft 118. As shown in FIG. 3, the tendon assembly 103 is located off-center of the distal catheter shaft 118; and, the needle assembly 109 is located approximately in the center of the distal catheter shaft 118. The tendon assembly 103 needs to be off-center to be able to deflect the distal section 102 of the catheter assembly 100. The tendon assembly 103 is disposed within the tendon lumen 126, which is positioned off-centered in the distal catheter shaft 118. The needle assembly 109 is disposed within the needle lumen 168, which is a positioned approximately in the center of the distal catheter shaft in one embodiment. The central lumen 131 may be filled with polymer to secure the tendon assembly 103 and the needle assembly 109. Surrounding the central lumen 131 is a compression cage 122 (details below) and surrounding the compression cage 122 is a distal jacket 120 that defines the outer diameter for the distal catheter shaft 118. The distal catheter shaft 118 may have more lumens disposed therein to house additional tools, components, or needle assemblies if necessary.

FIG. 4 shows a cross-section P1 of the proximal catheter shaft 112. As shown in FIG. 4, the tendon assembly 103 is located approximately in the center of the proximal catheter shaft 112. In some embodiments, the proximal catheter shaft 112 have several off-center lumens, lumens 166, 167, and 168, formed therein. The needle lumen 168 is occupied by the needle assembly 109 as previously mentioned. Both or none of the lumens 166 and 167 may be occupied by additional needle assembly (e.g., a needle assembly 105 having a needle 125 and a needle assembly 107 having a needle 123), or alternatively by a lumen filler. Having the additional off-center lumens provides a balance to the proximal catheter shaft 112. When the lumens 166 and 167 are included for balancing purpose, they need not be extended into the distal catheter shaft 118 as the tendon lumen 126.

Returning to FIG. 2, the details the configuration of components of the deflectable catheter assembly 100 are shown. In FIG. 2, the catheter shaft 101 is divided into two sections referred to as a proximal catheter shaft 112 and a distal catheter shaft 118.

The distal catheter shaft 118 includes a distal core shaft 124 and the proximal catheter shaft 112 includes a proximal core shaft 116. Each of the distal core shaft 124 and the proximal core shaft 116 is made of a polymer such as polyether block amides (Pebax®; Pebax is a registered trademarks of Ato Fina Chemicals), Nylon, or Polyurethane. The material used for the distal core shaft 124 is more flexible (e.g., lower in hardness durometer) than the material used for the proximal core shaft 116.

In some embodiments, the proximal catheter shaft 112 is further divided into a middle catheter shaft (not labeled) and the proximal catheter shaft 112. The middle catheter shaft and the proximal catheter shaft 112 are constructed similarly but may have different flexibilities. When being used, the proximal catheter shaft 112 lays in relatively straight sections of the vascular anatomy such as the femoral arteries and the aorta. The proximal catheter shaft 112 functions mainly to transmit torque. Therefore, the proximal catheter shaft 112 is the stiffest section of the catheter assembly 100. The middle catheter shaft may lie around an arch section such as the aortic arch. The middle catheter shaft thus has to transmit torque over a curve. Therefore, the middle catheter shaft has to be relatively flexible compared to the proximal catheter shaft 112. To create the proximal catheter shaft 112 with different stiffness sections, different durometer materials are used for the proximal catheter shaft 112. For example, the proximal catheter shaft 112 can be constructed with high durometer materials such as Nylon 12 and Pebax72D while the middle catheter shaft can be constructed with slightly lower durometer materials such as Pebax63D, a blend of Pebax63D, or even lower durometer Pebax materials.

As illustrated in FIG. 2, at the catheter proximal section 104, the outer most layer of the catheter shaft 101 is the proximal catheter shaft 112 which functions as a torque shaft that can deliver torque from a proximal handle manipulation to the catheter distal section 102. In one embodiment, the proximal catheter shaft 112 is made of a polymer tube reinforced with a support braided layer 114 made of braided wires embedded within a support polymer layer. The support braided layer 114 can have forms of wires and ribbon, round or flat and can be made of metals such as stainless steel, NiTi, or strong polymer such as Nylon, and Peek. The wire cross-section of the wires in the layer 114 can be round, rectangular, or any other suitable shape. The support polymer layer can be made of polymers commonly used in catheter construction such as Nylon, Pebax, Polyurethane, Polyolefin, etc.

The distal catheter shaft 118 is a flexible section that allows the catheter distal section 102 to deflect when the tendon 130 is pulled. The distal catheter shaft 118 includes a layer of a low durometer material such as a low durometer Pebax. The low durometer material used for the distal catheter shaft 118 has a lower hardness scale compared to the proximal catheter shaft 112 for example, the material used for the distal catheter shaft 118 may have a hardness scale of about 35 D.

The distal catheter shaft 118 has at least two functions: to house the distal portions of the internal components of the catheter assembly 100 and to facilitate the deflection of the catheter distal section. As illustrated in FIGS. 2-3, the distal section 102 is comprised of two components: a distal jacket 120, a compression cage 122 and a distal core shaft 124. The distal jacket 120 acts as an outer packaging layer for the internal components of the catheter assembly 100 that are housed in the catheter distal section 102. It is made of polymeric materials such as Nylon, Pebax, Pebax blend and low durometer material. In order to facilitate a bias to deflect the catheter distal section 102, the distal catheter shaft 118 needs to be made of lower durometer and more flexible materials than those used for the catheter proximal section 112 to allow the tendon 130 to deflect the distal catheter shaft 118 when being pulled.

The following sections describe in details the construction of the catheter assembly 100. The catheter assembly 100 is constructed in the order of constructing the inside components to the outside components. In addition, the catheter proximal section 104 and the catheter distal section 102 are constructed separately and joined together to form the catheter assembly 100.

Figure 5:
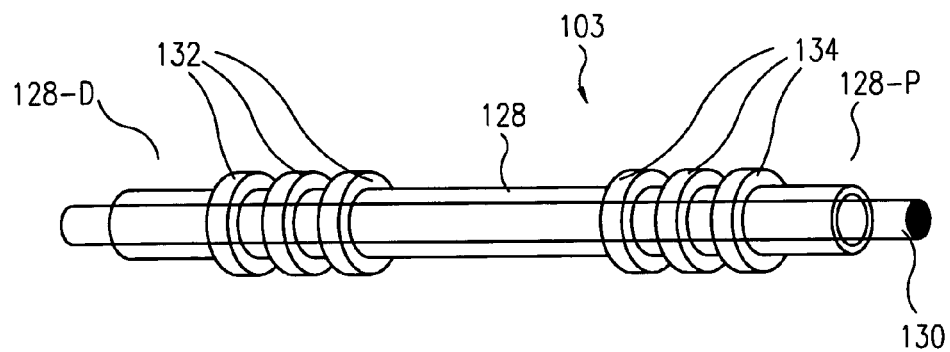
FIG. 5 illustrates a tendon assembly.
Figure 6:
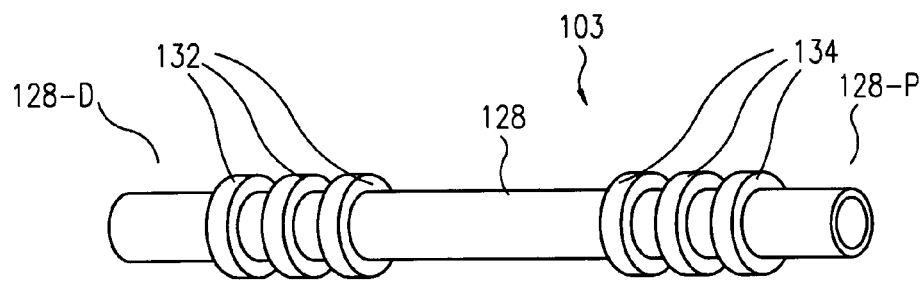
FIGS. 6-8 illustrate the various components of a tendon assembly.

First, the tendon assembly 103 is prepared. The tendon assembly 103 is made stiffer at the catheter proximal section 104 than at the catheter distal section 102. Starting with the catheter proximal section 104, the tendon assembly 103 is prepared. As illustrated in FIG. 5, the tendon assembly 103 includes an axial spine 128, at least two set of slip bands 132 and 134 and a tendon 130. In FIG. 6, the axial spine 128 is provided. The first set of slip bands 132 is bonded to the distal end of the axial spine 128. The most distal slip band 132 is placed at a short distance (e.g., about 2-9 cm) from the distal end 128-D of the axial spine 128. The remaining slip bands 132 are spaced at a similar distance away from each other. The most proximal slip band 134 is placed at a short distance (e.g., about 2-9 cm) from the proximal end 128-P of the axial spine 128. The slip bands 132 and 134 prevent slippage between the axial spine 128 and the proximal core shaft 116. The tendon 130 is disposed within the axial spine 128 after the construction of the catheter shaft 101 is completed.

The axial spine 128 is made of a longitudinally stiff material that can provide resistance to catheter compression during deflection. It also provides a lumen for the tendon 130 to reside therein. The axial spine 128 runs longitudinally within the proximal catheter shaft 112 as illustrated in FIG. 2. The axial spine 128 may run the entire length of the proximal catheter shaft 112 or have approximately the same length as and be positioned substantially coincident with the proximal catheter shaft 112. The axial spine 128 is thus substantially aligned with the proximal catheter shaft 112. The axial spine 128 is used to resists catheter compression (e.g., along the proximal catheter shaft 112) and/or needle assembly compression when the tendon 130 is pulled to deflect the catheter distal section 102. Catheter compression results in a length change to the catheter shaft 101 and distorts torque response integrity and is thus not desirable. Needle assembly compression results in a length change to the needle assembly affecting accuracy of the needle extension. The axial spine 128 is made of a metallic tube made of material such as NiTi, stainless steel, or other metallic alloy. The axial spine 128 should be sufficiently sized so that its inner diameter can accommodate the tendon 130.

The slip bands 132 and 134 can be made of metallic tubes, bands, or rings. In an alternative embodiment, each of the slip-bands 132 and 134 can be replaced with a stack coil assembly (not shown). The ends of the axial spine 128 with the slip bands 132 and 134 are indicated as a section 108 and a section 110, respectively, in FIG. 2. With the axial spine 128 surrounding the tendon 130, when the catheter assembly 100 is pulled under compression by the tendon 130 to deflect the catheter distal section 102, the axial spine 128 holds the length of the catheter proximal section 104 constant.

Figure 7:
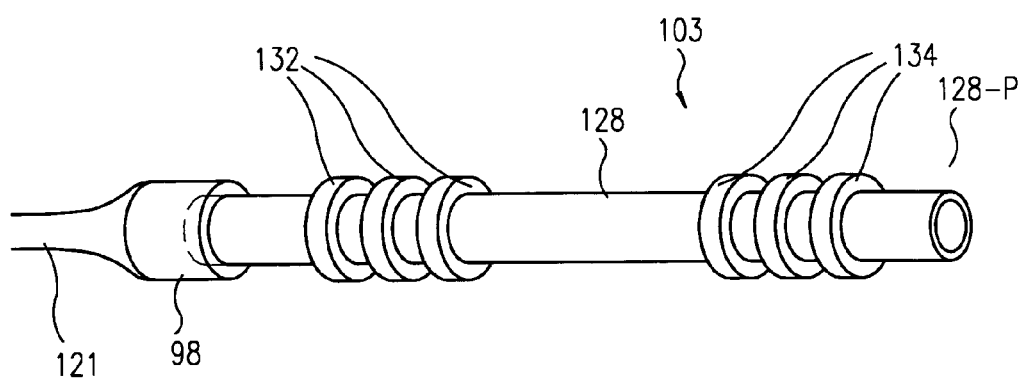

For the catheter distal section 102, the tendon assembly 103 is prepared as illustrated FIG. 7. The axial spine 128 of the tendon assembly 103 is replaced with a flexible tendon sheath 121. One reason for that is that the tendon assembly 103 needs to be flexible at the distal section 102 of the catheter assembly 100 whereas the tendon assembly 103 needs to be stiff at the proximal section 104 to be able to resist compression as an axial spine. As shown in FIG. 7, the flexible tendon sheath 121 is joined onto the axial spine 128. The flexible tendon sheath 121 can be joined to the axial spine 128 by overlapping a proximal section of the tendon sheath 121 over a distal section of the axial spine 128 to form an overlapping space 98 as shown in FIG. 7. In one embodiment, adhesive is dispensed between the overlapping space 98 between the flexible tendon sheath 121 and the axial spine 128. Alternatively, openings (not shown) are created through the wall of the tendon sheath 121 in the overlapping space 98 and adhesive can be dispensed into the openings to join the flexible tendon sheath 121 to the axial spine 128. In one embodiment, to maintain the opening in the flexible tendon sheath 121 during subsequent heat fusion processes to form the catheter shaft 101, a mandrel 148 is inserted into the flexible tendon sheath 121. The mandrel 148 defines the inner diameter of the flexible tendon sheath 121. The inner diameter of the flexible tendon sheath 121 should be sufficiently sized to accommodate the tendon 130. The flexible tendon sheath 121 is substantially aligned with the distal catheter shaft 118 and thus extends along the entire distal catheter shaft 118.

In on embodiment, the flexible tendon sheath 121 is made of polytetrafluoroethylene (PTEF) or TEFLON® (TEFLON is a registered trademark of Dupont), high-density polyethylene (HDPE), polyetheretherketone (PEEK), or polyimide with a somewhat lubricious lumenal wall. The axial spine 128 is made of stainless steel, nickel titanium or Nitinol, or other suitable material. The tendon 130 is a metallic wire having a strong tensile strength such as stainless steel.

Figure 9:
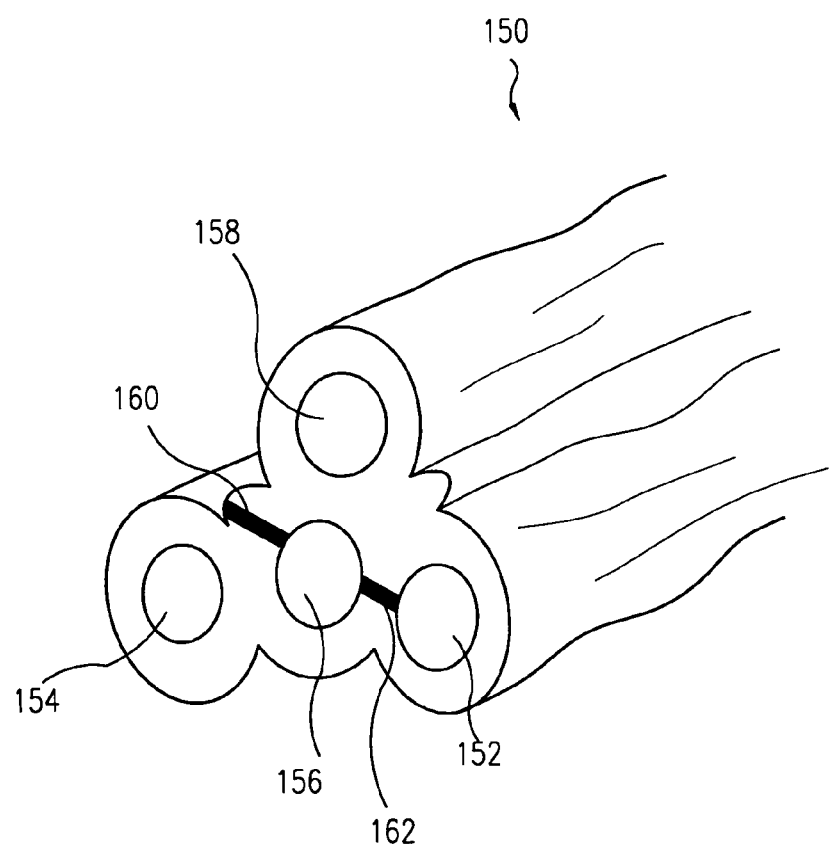
FIGS. 9 and 10A-10E illustrate simplified three-dimensional views of exemplary methods of making the catheter assembly illustrated in FIG. 3.

Next, the distal catheter shaft 118 is prepared. In FIG. 9, a multi-lumen extruded tube 150 is provided. The multi-lumen extruded tube 150 will later form a distal core shaft 124 for the catheter distal shaft 118. In one embodiment, the multi-lumen tube 150 includes lumens 152, 154, 156, and 158 with the lumen 156 being in the central lumen while the lumens 152, 154, and 158 are located radially around the lumen 156. It is to be appreciated that more or less lumens than shown in FIG. 9 may be used depending on how many lumens are needed for the catheter shaft 101. A slit is cut into the lumen 156 and into one of the side lumens (e.g., the lumen 152). This is done so that the tendon assembly 103 can be transitioned from the center of the catheter shaft 101 to the side of the catheter shaft 101 in order to deflect the catheter distal section 102 when the tendon 130 is being pulled. In addition, the needle assembly 109 can also be transitioned from the side of the catheter shaft 101 into the center of the catheter shaft 101. In one embodiment, a first slit 160 is cut into the central lumen 156. The first slit 160 has a length that covers most of the length of the multi-lumen extruded tube 150 except for a short distance (e.g., 0.5-1.5 cm) from the proximal end of the tube 150. A second slit 162 is cut through the wall between the side lumen 152 and the central lumen 156. The second slit 162 is located on the oppose side of the first slit 160. The second slit 162 has a length that covers most of the length of the multi-lumen extruded tube 150 except for a short distance (e.g., 0.5-1.5 cm) from the proximal end of the tube 150. The first slit 160 is formed to allow the tendon assembly 103 to move from being in (or approximately in) the center of the catheter shaft 101 to the side of the catheter shaft 101 at the distal catheter shaft 118. The second slit is formed to allow the needle assembly 109 to move from an off-center location to an approximately center location.

Figure 10A:
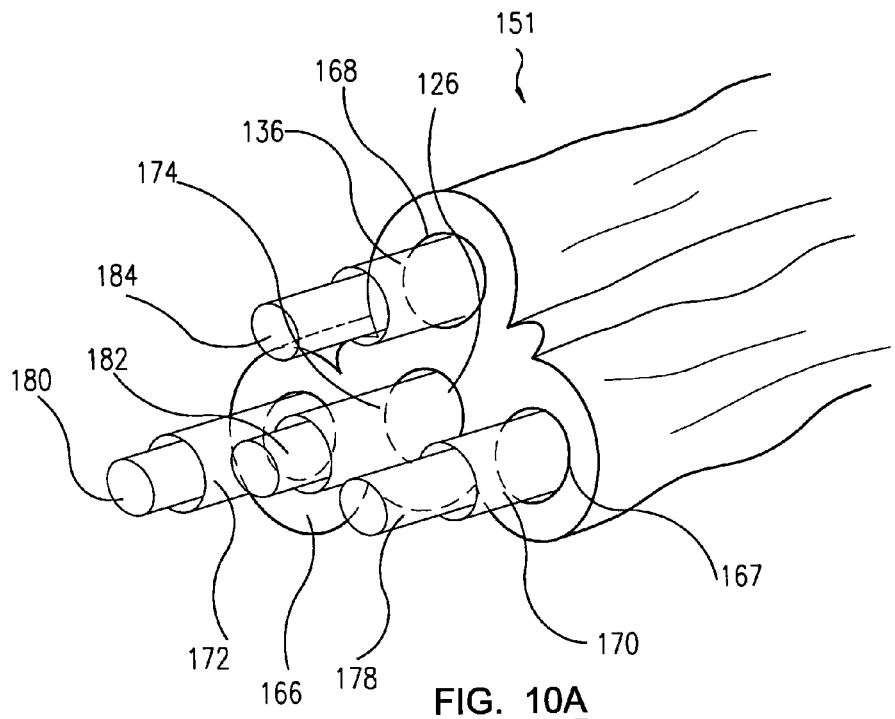

Next, the proximal catheter shaft 112 is prepared. In FIG. 10A, a multi-lumen extruded tube 151 is provided. The multi-lumen extruded tube 151 will later form the proximal core shaft 116 for the catheter proximal shaft 112. In one embodiment, the multi-lumen extruded tube 151 includes a tendon lumen 126, needle lumens 166, 167, and 168, with the tendon lumen 126 being in the central lumen while the needle lumens 166, 167, and 168 are located radially around the lumen 126. It is to be appreciated that more or less lumens may be used depending on how many lumen are needed for the catheter assembly 100. Low-friction liners are inserted into the lumens: a liner 174 is inserted into the tendon lumen 126; a liner 136 is inserted into the needle lumen 168; a liner 170 is inserted into the needle lumen 167; and, a liner 172 is inserted into the needle lumen 166. The liners can be made of PTFE, or TEFLON, HDPE, PEEK, or polyimide. A mandrel is inserted into each of the liners to define the inner diameter of each lumen: a mandrel 182 is inserted into the liner 174; a mandrel 180 is inserted into the liner 172; a mandrel 178 is inserted into the liner 170; and, a mandrel 184 is inserted into the liner 136.

The liner 174 for the tendon lumen 126 is shorter than the length for catheter proximal section 104 (FIG. 2). The liner 174 has a length that is about equal to the length of the section that is between the sections 108 and 110 of the catheter proximal section 104. The liner 174 also has an internal diameter that is slightly larger than the outer diameter of the axial spine 128 to give freedom for the axial spine 128 to self adjust and, therefore, reduce torque response resistance, during the turning or advancing of the catheter shaft 101. Having no liner in the sections 108 and 110 allows the material from the catheter proximal shaft 112 to collapse under compression of a shrink tube in a heat fusion process, around the slip bands 132 and 134 and the axial spine 128 to anchor both ends of the axial spine 128. The liners 136, 170, and 172 for the side lumens are longer than the length for the liner 174. The extra length of each of the liners 136, 170, and 172 will go into the lumens in the distal catheter shaft 118 that is prepared as shown in FIG. 9. Each of the liners 136, 170, 172, and 174 may be chemically treated (e.g., etched) to increase adhesion of the liners to the polymer of the tubes 151 and 150.

In embodiments where some of the lumens are included only for balancing purposes, the liners and mandrels will not be extended into the lumens in the distal catheter shaft 118. After the final heat fusion, the extra lumens in the distal catheter shaft 118 are closed since there is no liner and mandrel to keep the lumen open. Balancing of the catheter shaft 101 is only needed in the proximal catheter shaft 112.

Figure 10B:
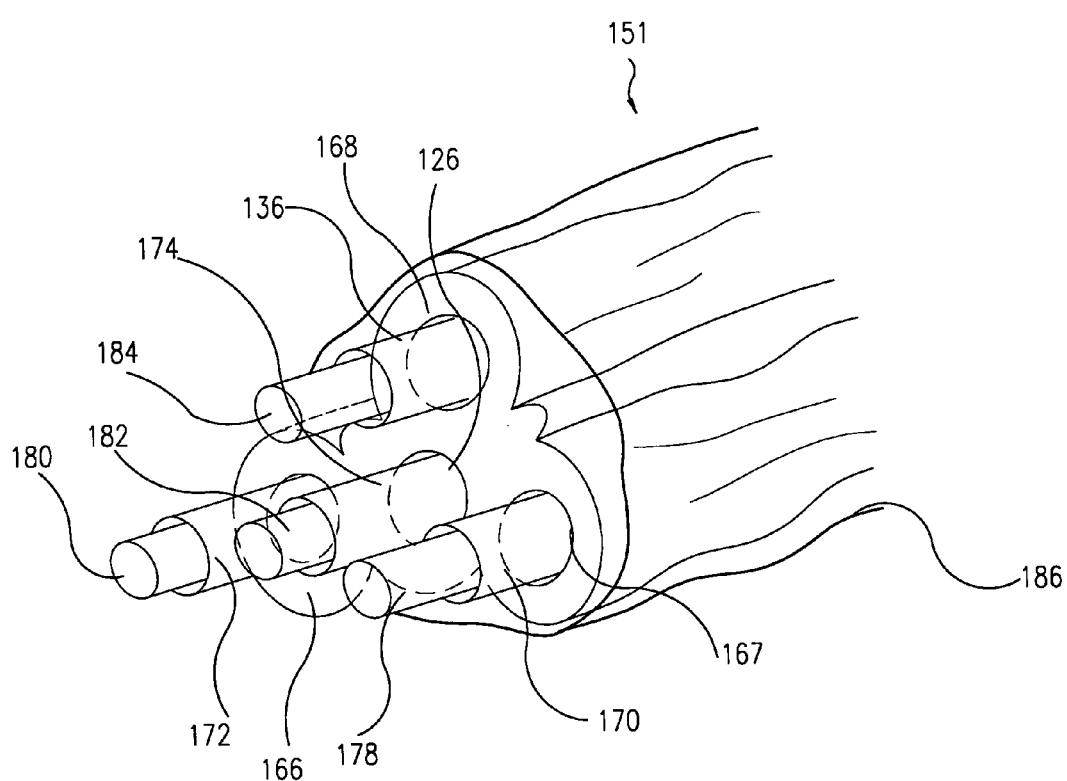

In FIG. 10B, a shrink tube 186 is placed over the tube 151 that now has the liners and mandrels and the whole assembly is reformed under a heat source. Only the section that is located between the section 108 and the section 110 (FIG. 2) is heated. The polymer in the heated section melts and collapses onto the liners under the compression of the shrink tube forming a multi-lumen proximal core shaft 116. The shrink tube helps define the outer diameter of the proximal core shaft 116 while the mandrels define the inner diameter of the lumens.

Figure 8:
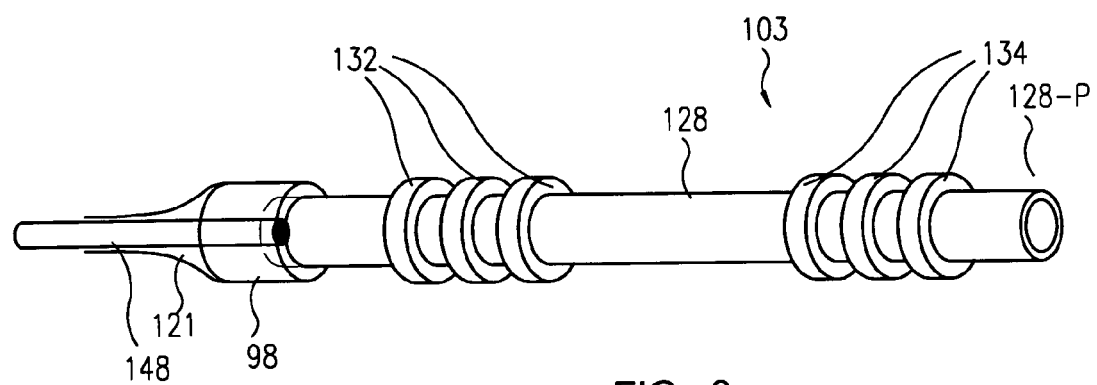
Figure 10C:
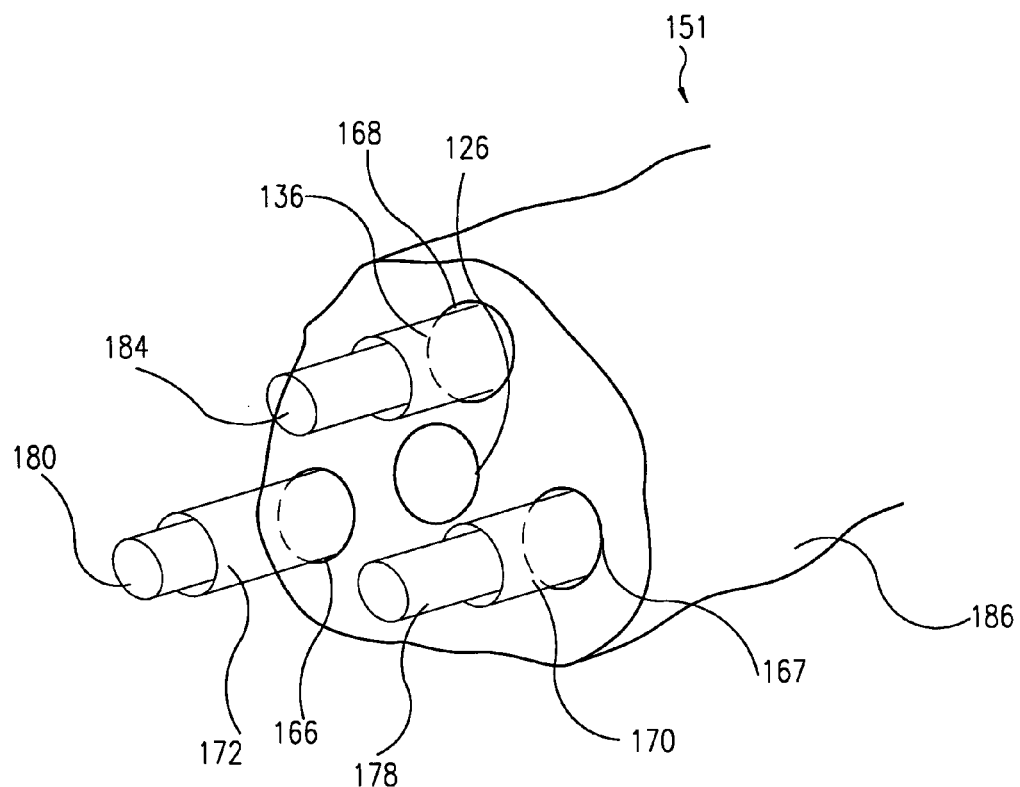
Figure 10D:
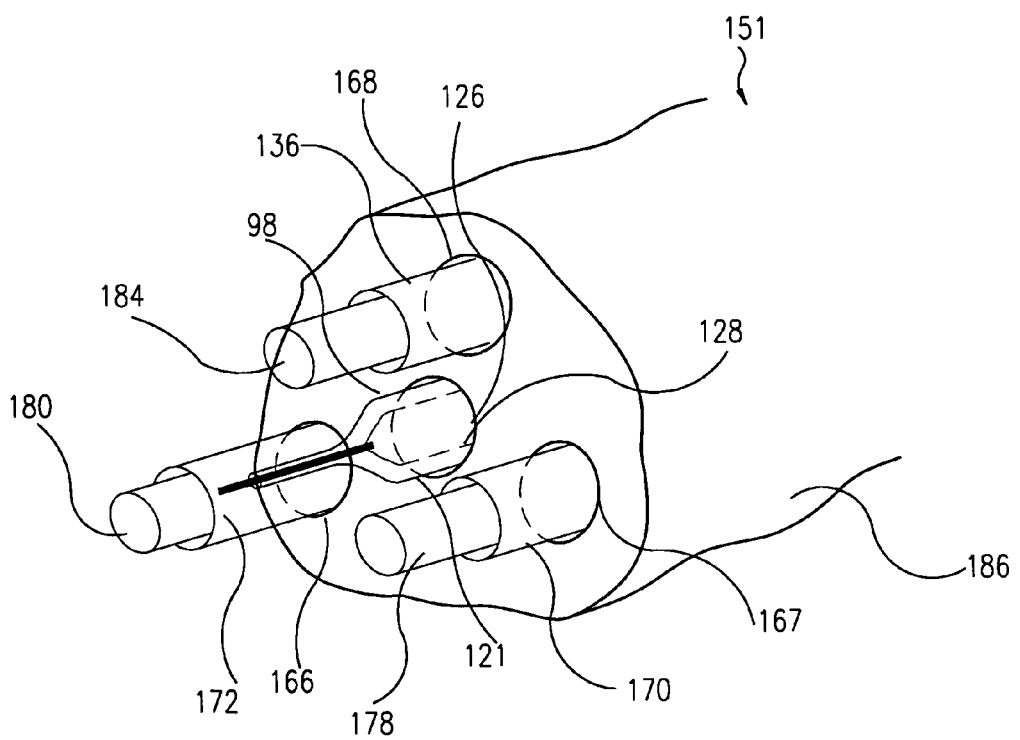

In FIG. 10C, the mandrel 182 for the tendon lumen 126 is removed. At this point, the proximal catheter shaft 112 is prepared. In FIG. 10D, the tendon assembly 103 that includes, up to this point, the flexible tendon sheath 121, the axial spine 128, and the slip bands 132 and 134, along with the mandrel 148 shown in FIG. 8 is inserted within tendon lumen 126. The slip bands 132 and 134 should be located under the sections 108 and 110 of the proximal catheter shaft 112, respectively.

Figure 10E:
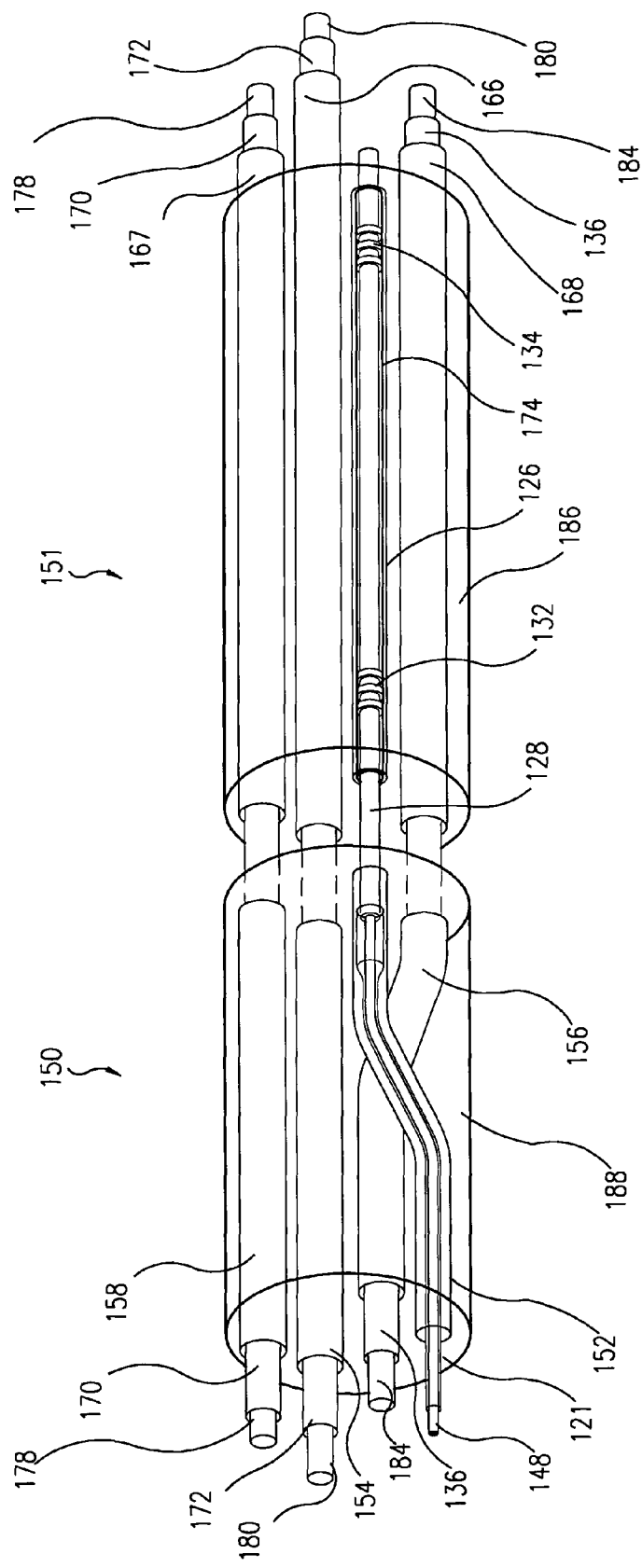

Next, as shown in FIG. 10E, the distal core shaft (the multi-lumen extruded tube 150) is coupled to the proximal core shaft (the multi-lumen extruded tube 151). The mandrels and the respective extra length of the liners 136, 170, and 172 originally over hanging from the multi-lumen extruded tube 151 are inserted into the lumens of the multi-lumen extruded tube 150. The mandrel 148 and the flexible tendon sheath 121 are inserted into the central lumen 156 of the multi-lumen extruded tube 150. At the proximal end of the first slit 160, the tendon sheath 121 and the mandrel 148 are brought out of the central lumen 156 and placed along the wall space made by the first slit 160. This will form the off-center tendon lumen 126 (shown in FIGS. 2-3) in the catheter distal section 102 after a heat fusion process. The tendon 130 of the tendon assembly 103 is later disposed within the tendon lumen 126 as will be described below.

Also in FIG. 10E, each of the liners 136, 170, and 172 (along with their respective mandrels) is inserted into one of the side lumens. In one embodiment, at the proximal end of the second slit 162, the liner 136 and the mandrel 184 are brought into the center of the tube 150 to prepare for the forming of a central lumen 164. This will form the center needle lumen 164 for the catheter distal section 102.

Next, the distal core shaft 124 and the proximal core shaft 116 are formed. In FIG. 10E, a shrink tube 188 is placed over the multi-lumen 150 and section 108 (FIG. 2) of the multi-lumen tube 151. The shrink tube 188 defines the outer diameter of the distal core shaft 124. The shrink tube 186 that defines the outer diameter of the proximal core shaft 116 is also placed over the multi-lumen 150 as illustrated in FIGS. 10B-10E. The distal section 102 and the section 108 of the proximal section 104 are heated under a heat source. In addition, the section 110 of the proximal section 104 is also placed under a heat source. The polymer melts and collapses into the support mandrels under the compression from the shrink tubes 188 and 186, allowing for the formation of the distal core shaft 124 and the proximal core shaft 116. After the heat fusion process, the shrink tubes 188 and 186 are removed from the formed distal core shaft 124 and the proximal core shaft 116.

Next, the distal catheter shaft 118 and the proximal catheter shaft 112 are formed. In one embodiment, a compression cage 122 (details below) is placed over the distal core shaft 124 (FIGS. 2-3). A support braided layer 114 is placed over the proximal core shaft 116 (FIG. 2). The support braided layer 114 can be made of materials such as stainless steel, Nylon, PEEK, or cold worked Nitinol. A layer of support polymer that will form the distal jacket 120 is placed over the compression cage 122. An outer shrink tube (not shown) is then placed over the support polymer. In addition, a layer of support polymer is placed over the support braided layer 114 and an outer shrink tube is placed over the polymer layer. After heat fusion, the polymer will embed the braided layer 114 there within. These outer shrink tubes define the outer diameter of the catheter shaft 101. The outer shrink tubes are removed after the heat fusion that completes the distal catheter shaft 118 and the proximal catheter shaft 112.

In one embodiment, for the distal catheter shaft 118, heat is applied only to the two ends of the outer shrink tube that covers the distal jacket 120. After the heat fusion process, only the two ends of the compression cage 122 is attached to the distal jacket 120. The compression cage 122 is thus allowed to move more freely within the distal jacket 120. The compression cage 122 thus allows the internal components within catheter distal section 102 to move during deflection thus lowering the deflection stiffness.

For the proximal catheter shaft 112, heat is applied across the entire length of the outer shrink tube. The polymer fuses into the support braided layer 114 forming the proximal catheter shaft 112.

The mandrels can be removed after the catheter shaft 101 is formed. After the mandrels are removed, the lumens are vacant. The internal components of the catheter assembly 100 can then be disposed within the catheter shaft 101 as necessary. Unoccupied lumens can be filled with lumen fillers to maintain balance for the catheter shaft 101 if necessary.

The compression cage 122 and method of making the same is described in details in U.S. Ser. No. 2002/0165461 now U.S. Pat. No. 6,585,718, which is hereby incorporated by reference in its entirety. The compression cage 122 functions to maintain the axial length of the catheter distal section 102, prevents stretching of the catheter distal section 102, resists prolapse or kinking of the catheter distal section 102, maintains inner lumen integrity for the catheter distal section 102, and provides support for therapeutic tool engagement with the anatomy. The compression cage 122 is configured to resist axial and radial compression loads while maintaining flexibility.

Various configurations of the compression cage 122 can be seen in FIGS. 11A-11E. The compression cage 122 includes a proximal end 122-P, a distal end 122-D, and a central lumen 122-L there between. The compression cage 122 is ideally made from a resilient material, such as Nitinol, spring-temper austenitic stainless steel, or heat-treatable stainless steel so that upon unloading it tends to return to a pre-established shape, such as straight. In some embodiments, the compression cage 122 is configured to be a stent-like structure using the material mentioned above such as NiTi, stainless steel, or other metallic alloy.

Figure 11A:
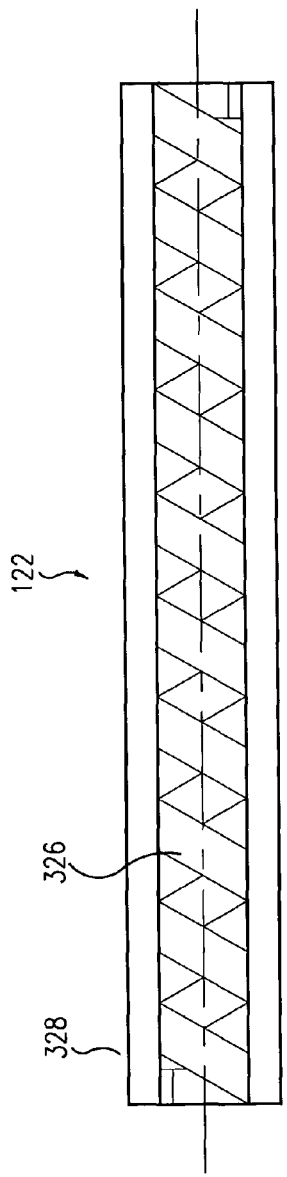

In one embodiment, as illustrated in FIG. 11A, the compression cage 122 includes a flat-wire coil 326 and two substantially longitudinal struts 328. The struts 328 are diametrically opposed to each other and are welded, soldered, brazed, adhered, or otherwise attached to some or all loops of the coil 326.

Figure 11B:
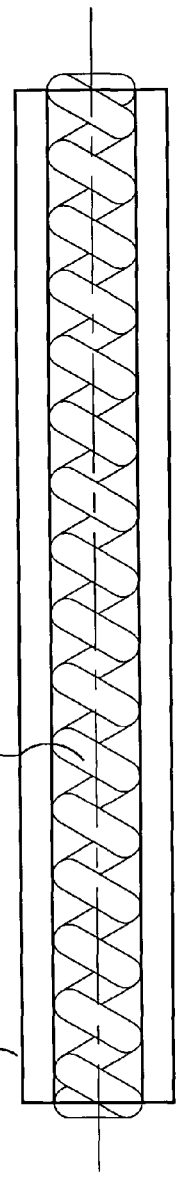

In another embodiment, as illustrated in FIG. 11B, the compression cage 122 includes a round-wire coil 330 and two substantially longitudinally struts 332. The struts 332 are diametrically opposed to each other and are welded, soldered, brazed, adhered, or otherwise attached to some or all loops of the coil 330.

Figure 11C:
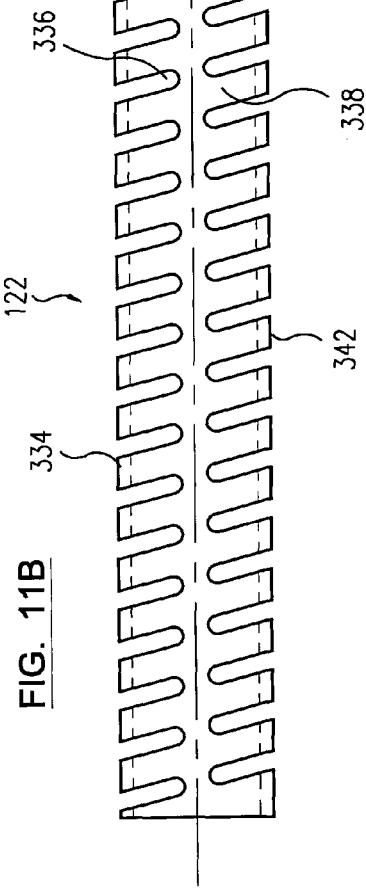

In another embodiment, as illustrated in FIGS. 11C-11D, the compression cage 122 includes a substantially tubular member 334 with an array of deep notches 336 that are diametrically opposed to each other. The material remaining between the opposing notches 336 functions as struts 338. The struts 338 can be aligned perpendicular to the lumenal longitudinal axis or aligned at a spiral angle (FIGS. 11A-11E).

In yet another embodiment, as illustrated in FIG. 11E, the compression cage 122 includes a linear array of rings 340 and two substantially longitudinal struts 342 that interconnect the rings 340. The struts 342 are diametrically opposed to each other and are welded, soldered, brazed, adhered, or otherwise attached to each of the rings 340.

The primary function of the struts 328, 332, 338, and 342 is to provide columnar strength to the compression cage 122. When a tensile load is applied to the steering tendon 130 to induce deflection of the catheter distal section 102, the reaction of the load is carried by the struts 328, 332, 338, and 342 within the compression cage 122 and transferred to the catheter proximal section 104. The compression cage 122 deflects laterally most easily in a direction that is perpendicular to the plane in which a pair of opposing struts 328, 332, 338, or 342 are located.

The compression cage 122 maybe attached to the inner surface of the distal catheter shaft 120 by melt-bonding, adhesive, or some equivalent mechanical binding techniques. Alternatively, the compression cage 122 may be combined with the distal catheter jacket 120 into one integral component. Alternatively, the compression cage 122 may reside loosely within the distal catheter shaft 118 provided its distal end and proximal end are connected so as to transfer axial loads through the opposite struts 328, 332, 338, and 342. In one embodiment, the heat source is only applied over the distal portion 122-D and the proximal portion 122-P of the compression cage 122 such that the polymer only melts into these two portions. Thus the compression cage resides loosely in the section between the distal portion 122-D and the proximal portion 122-P.

In an alternative embodiment, the compression cage 122 is replaced with a helical coil structure 165 shown in FIG. 12. The helical coil structure 165 can be made of a resilient material such as stainless steel, Nylon, or Nitinol. The helical coil structure 165 can be a braided mesh made of round wires or ribbons. During the heat fusion process, the heat source is applied to the distal portion and the proximal portion of the helical coil structure 165. The polymer having a low durometer from the distal jacket 120 melts into these two portions. The helical coil structure 165 resides loosely in the section between the distal portion and the proximal portion similar to the case of the compression cage 122. Alternatively, heat can be applied across the entire section of the helical coil structure and the polymer will melt over the entire helical coil structure 165.

After the catheter shaft 101 is formed, a transition section 106 (FIG. 2) is formed near the proximal end of the catheter distal section 102. Several features define the transition section 106. First, the tendon assembly 103 is shifted from the center of the catheter shaft 101 to being off-center at the transition section 106 thus, creating an off-center moment when the tendon 130 is pulled. Second, the distal catheter shaft 118 is made much more flexible compared to the proximal catheter shaft 104 thus, creating a bias for deflection under the tension from the tendon 130. Third, and in some embodiments, in addition to the change in the tendon assembly 103 location, the needle assembly 109 are moved toward the center of the distal catheter shaft 118. Fourth, the flexible tendon sheath 121 replaces the axial spine 128 at this section to allow for more flexibility for the tendon 130 to function. Fifth, the proximal catheter shaft 112 is transitioned to the distal catheter shaft 118. Sixth, the proximal core shaft 116 is transitioned to the compression cage 122 and distal core shaft 124.

Next, the needle assembly 109 is disposed within the catheter shaft 101 (FIG. 2). It is appreciated that more than one needle assembly (e.g., needle assembly 109) may be disposed within the catheter shaft 101. For example, as illustrated in FIG. 4, needle assemblies 105 and 107 are included along with the needle assembly 109. Each of the needle assemblies, 109, 105, and 107 may include a lubricious or low-friction needle sheath (e.g., made of PTFE or TEFLON) disposed on the outside of the needle assembly to facilitate the movement of the needle assembly within the lumen. Alternatively, each needle assembly may be coated with a lubricious material or be made of a lubricious material to facilitate the movement of the needle assembly within the lumen. Each needle assembly is extendable from the distal end of the catheter shaft 101 to outside of the catheter shaft 101. At the distal end of the catheter shaft 101, the needle sheath may be glued or otherwise adhered to the distal tip anchor 140. The distal end of the catheter shaft 101 includes an exit opening 97 to allow the needle assembly 109 to exit the catheter shaft 101 and reach a target site. In one embodiment, each needle assembly is coupled to an injection port (e.g., connection port 204 shown in FIG. 1). Each needle assembly includes a needle made of a durable material such as metal, stainless steel, Nitinol, polymer, or a combination thereof. The needle can be any conventional needle as is known in the art. The needle typically has a beveled tip or a sharp tip to allow it to enter a target site for treatment.

Next, the tendon 130 is disposed within the catheter shaft 101. The tendon 130 is only inserted into the catheter shaft 101 after all the internal components of the catheter shaft 101 are assembled into the catheter shaft 101. Referring to FIG. 2, the catheter assembly 100 includes a distal tip anchor 140 at the distal end of the distal catheter shaft 118. The distal tip anchor 140 is made with a metallic material such as stainless steel, platinum alloy, brass, or the like, in one embodiment. The distal tip anchor 140 is coupled to the compression cage 122 and the distal catheter shaft 118, for example by, adhesive, welding, soldering, crimping, mechanical interference, etc.

In one embodiment, the distal tip anchor 140 functions as a tendon anchor. The tendon 130 is coupled to the wall of the distal tip anchor 120 by adhesive, welding, soldering, crimping, mechanical interference, or other suitable technique. In one embodiment, after the tendon 130 is coupled to the distal tip anchor 120, the tendon 130 is then inserted into the tendon lumen 126 from the distal end of the distal catheter shaft 118. The tendon 130 is pushed proximally until the tendon 130 reaches the proximal catheter shaft 112 and extends out of the proximal catheter shaft 112.

The tendon 130 is made of metallic wire having a high yield strength and high elastic modulus. Stainless steel or cold worked Nitinol can be used to make the tendon 130 to provide it with such properties. The tendon 130 can have round, rectangular, or other suitable shape cross sections. Alternatively, the tendon 130 can also be made out of a polymeric material such as Kevlar® (Kevlar is a registered trademark of Dupont).

The movement of the tendon 130 and the needles (e.g., needles 123, 125, or 138) is controlled by a catheter handle 200 (see below) attached to the proximal end of the catheter shaft 101. The tendon 130 is coupled to a pull-mechanism (which is included in the catheter handle 200), which has a limited travel distance. When the tendon 130 is pulled, the catheter distal section 102 deflects. The travel distance of the pull-mechanism can be locked at any location and will only move under a manual force.

FIG. 13 illustrates that in one embodiment, a needle stop mechanism is incorporated into the catheter assembly 100. As illustrate in this figure, the needle 138 includes a ring stop 190 and the needle lumen 164 that houses the needle 138 including a complimentary lumen stop 192. The ring stop 190 is attached to the outer wall of the needle 138 by conventional methods such as welding, soldering, and using adhesive. The lumen stop 192 is attached to the inner wall of the lumen 164 (e.g., by heat fuse or adhesive) and is configured to be complimentary to the ring stop 190. Thus, when the ring stop 190 meets (or engages) the lumen stop 192, the needle 138 is prevented from advancing any further than the meeting point. The ring stop 190 and the lumen stop 192 thus define the distal traveling distance for the needle 138. The inner wall of the lumen 164 can also include another lumen stop (not shown) similar to the lumen stop 192 at a section proximal to the lumen stop 192. This another lumen stop together with the ring stop 190 can define the proximal traveling distance for the needle 138. Thus, when the ring stop 190 meets (or engages) another lumen stop in the proximal area, the needle 138 is prevented from traveling any further in the proximal direction.

FIG. 13 also shows that in one embodiment, an electrode system is incorporated into the catheter assembly 100. In one embodiment, the catheter distal shaft 118 includes a tip electrode. The tip electrode can be the same component as the distal tip anchor 140 or be incorporated into the distal tip anchor 140. A conductive lead 144 is coupled to the tip electrode and extends along the distal catheter shaft 118, through the proximal catheter shaft 112 (not shown in this figure) and the proximal handle 200 (not shown in this figure), and connected to a detector system (not shown) outside of the catheter assembly 100. In one embodiment, another electrode 142 is incorporated into the distal catheter shaft 118. The electrode 142 can act as a reference electrode for the electrode system. Alternatively, the electrodes 140 and 142 can function as independent electrodes with their references attached elsewhere, for example, on the patient's body. The electrode 142 is placed proximal to and near the tip electrode. Another conductive lead 144 is coupled to the electrode 142 and extends to outside of the catheter assembly 100.

The electrode system provides many useful applications for the catheter assembly 100. The electrode system can provide mapping information and/or local drug delivery information for the catheter assembly 100. The electrode system also allows for sensing the local cardiac signal and wall contact between the catheter and the wall of the cardiac chamber, which may be useful for the delivery of biologic substance. More details in the configuration of an electrode system are followed below (FIGS. 32-34, 35A-35F, 36A-36B, and 37A-37B).

Figure 14A:
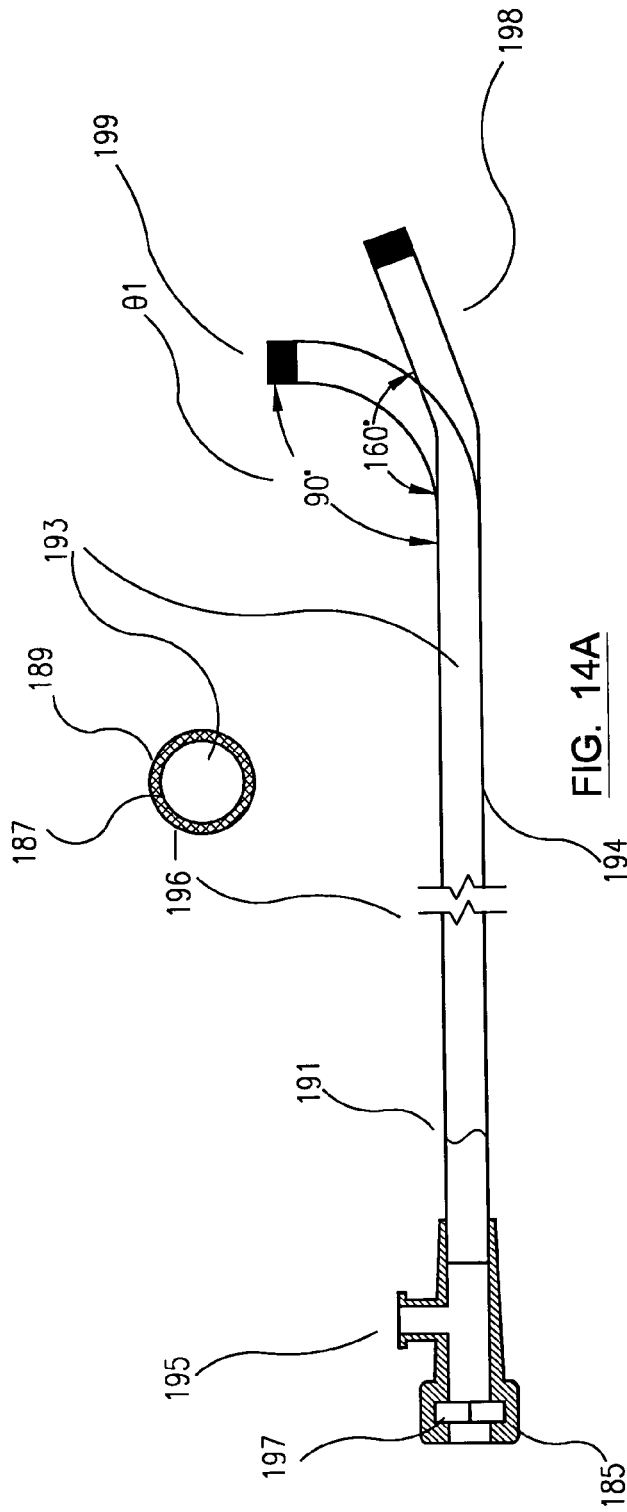
FIGS. 14A-14C illustrate an exemplary catheter assembly that includes a pre-shaped guide sheath to facilitate the maneuvering of the catheter assembly.
Figure 14C:
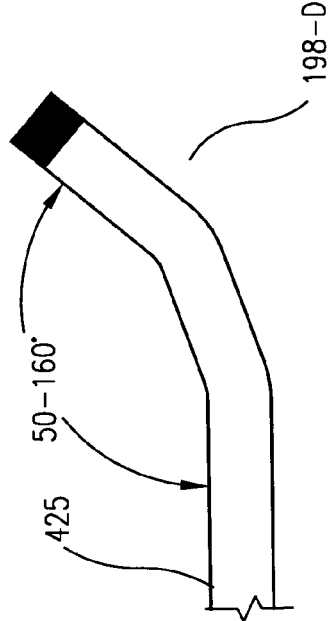
Figure 14B:
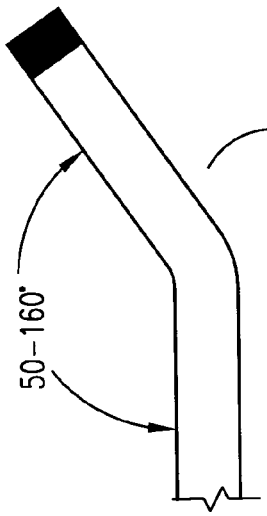

FIGS. 14A-14C illustrate that in some embodiments, a guide sheath having a pre-shaped distal section is disposed over the catheter assembly 100 or other catheter assemblies. FIG. 14A illustrates a guide sheath 194 that can be placed over the catheter assembly 100 to facilitate the introduction of the catheter assembly 100 into a patient. The guide sheath 194 includes a proximal section 191 and a pre-shaped distal section 198 having a distal tip 199. The guide sheath 194 includes an elongated lumen 193 extending through the distal section 198 and the proximal section 191. The elongated lumen 193 is configured to have an inner diameter that is sufficient to allow a catheter assembly such as the catheter assembly 100 to be inserted therethrough. The guide sheath 194 is not limited to be used with the catheter assembly 100 and can be used to facilitate the introduction of many different types of catheter assembly including alternative embodiments of the catheter assembly 100, for example a catheter assembly 400 or 344 described below. In one embodiment, the guide sheath 194 includes a middle section that is more flexible than the proximal section 191 to aid the maneuvering of the guide sheath 194 over tortuous pathways.

The guide sheath 194 is constructed with a lubricious liner 187 in the inner most lumen and a braided wire layer 189 on top of the liner 187, and heat fused together by a polymer jacket as illustrated in the cross-sectional view 196. The stiffness of the guide sheath 194 varies along all the sections of the guide sheath 194. The proximal section 191 is stiffer than the distal section 198. The distal tip 199 is lined by a soft material to create an atraumatic tip.

The pre-shaped distal section 198 can have one angular bend or two angular bends (or a dual-angular bend). The pre-shaped distal section 198 has an angle $\theta_1$ with respect to the proximal section 191. The angle $\theta_1$ may be of any suitable angles, for example, the angle $\theta_1$ may vary from 65-160 degrees. FIG. 14B illustrates that in one embodiment, the pre-shaped distal section 198 has an angular bend 198-S which is a single angular bend section having an angle that varies between about 50-160 degrees. FIG. 14C illustrates that in one embodiment, the pre-shaped distal section 198 has an angular bend 198-D which is a dual-angular bend section having two bent sections, wherein each may have an angle that varies between about 50-160 degrees.

The guide sheath 194 may be coupled to a handle 185 that includes a flush port 195 and a self-seal valve 197. In one embodiment, the guide sheath 194 is coupled to a handle at the proximal end of the guide sheath 194. A deflectable catheter shaft is inserted into the handle to go into the central lumen of the guide sheath 194. The flush port 194 is used to flush the space between the deflectable catheter shaft and the central lumen of the guide sheath 194. The self-seal valve 197 is included (for example within the handle) as a sealing around the deflectable catheter shaft to prevent back flow of the fluid (e.g., blood) that travels through the catheter. The self-seal valve 197 can also be used as a lock to lock the orientation of the deflectable catheter relative to the guide sheath 194. Locking can also be achieved by compressing an o-ring captured inside of the proximal adaptor of the guide sheath 194, coaxial to the central lumen, to tightly lock around the deflectable catheter shaft.

In one embodiment, during a therapeutic procedure, the guide sheath 194 is inserted first into the left ventricle through the aorta and the aortic valve of a patient by tracking over a guide wire (not shown). Then the guide wire is withdrawn. The guide sheath 194 creates a pathway through which a catheter assembly 100 can be inserted. A catheter assembly such as the steerable catheter assembly 100 (or one of the other catheter assemblies described herein) is then inserted through the guide sheath 194 into the ventricle. Once it is in the chamber of the heart, the guide sheath 195 can continue to provide support to the steerable catheter assembly 100. Its distal section 198 can provide additional direction to the steerable catheter assembly 100.

Figure 15A:
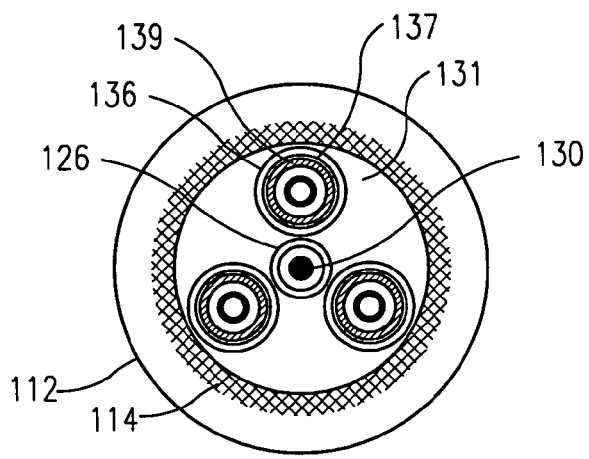
FIG. 15A illustrates a cross-sectional view of a catheter assembly that includes a needle disposed within a needle tube.
Figure 15B:
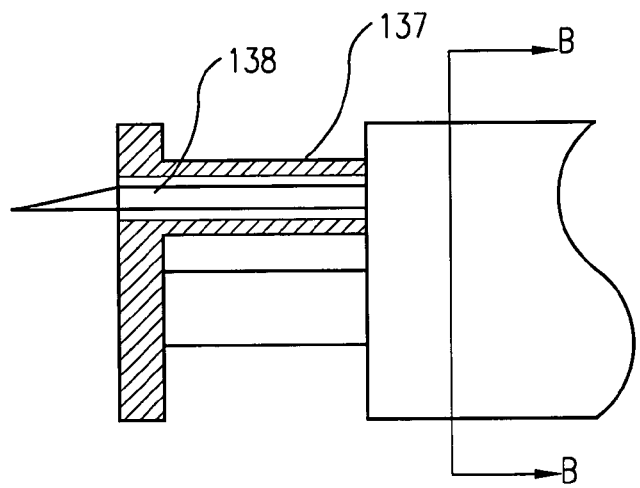
FIGS. 15B-15C illustrate simplified views of the catheter assembly shown in FIG. 15 with the needle tube being moveable relative to the catheter assembly.

FIGS. 15A-15D illustrate that in some embodiments, instead of having only the needles being the only components that are extendable out of the catheter shaft 101, the needles can be protected by needle tubes, which can also be configured to be extendable. Taking the needle 138 of FIG. 2 as an example, FIGS. 15A-15B illustrate that the extendable needle 138 is disposed within a lumen 139 of an extendable needle tube 137. The extendable needle tube 137 is configured to have adequate strength to support the needle 138. The needle tube 137 may be constructed with braided wire layer placed on the outside of the lumen 139 and embedded in a polymer jacket. The needle tube 137 has an outer wall that has low friction to allow the needle tube 137 to travel easily within the needle lumen in the catheter shaft 101. The extendable needle tube 137 is disposed within a lumen created in the catheter shaft 101 a previously described.

Figure 15C:
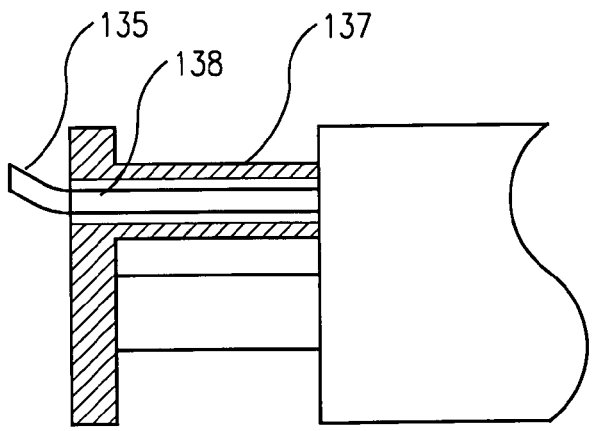

FIG. 15C illustrates that in one embodiment, instead of having the needle 138 extending out straight, the needle 138 can be configured to extend out at a divergent angle. This increases the injection zone diameter and increases the injection track length. The needle 138 can be made of superelastic NiTi material and pre-shaped to have the tip section 135 bends outward as the needle 138 is extended out of the needle tube 137.

Figure 15D:
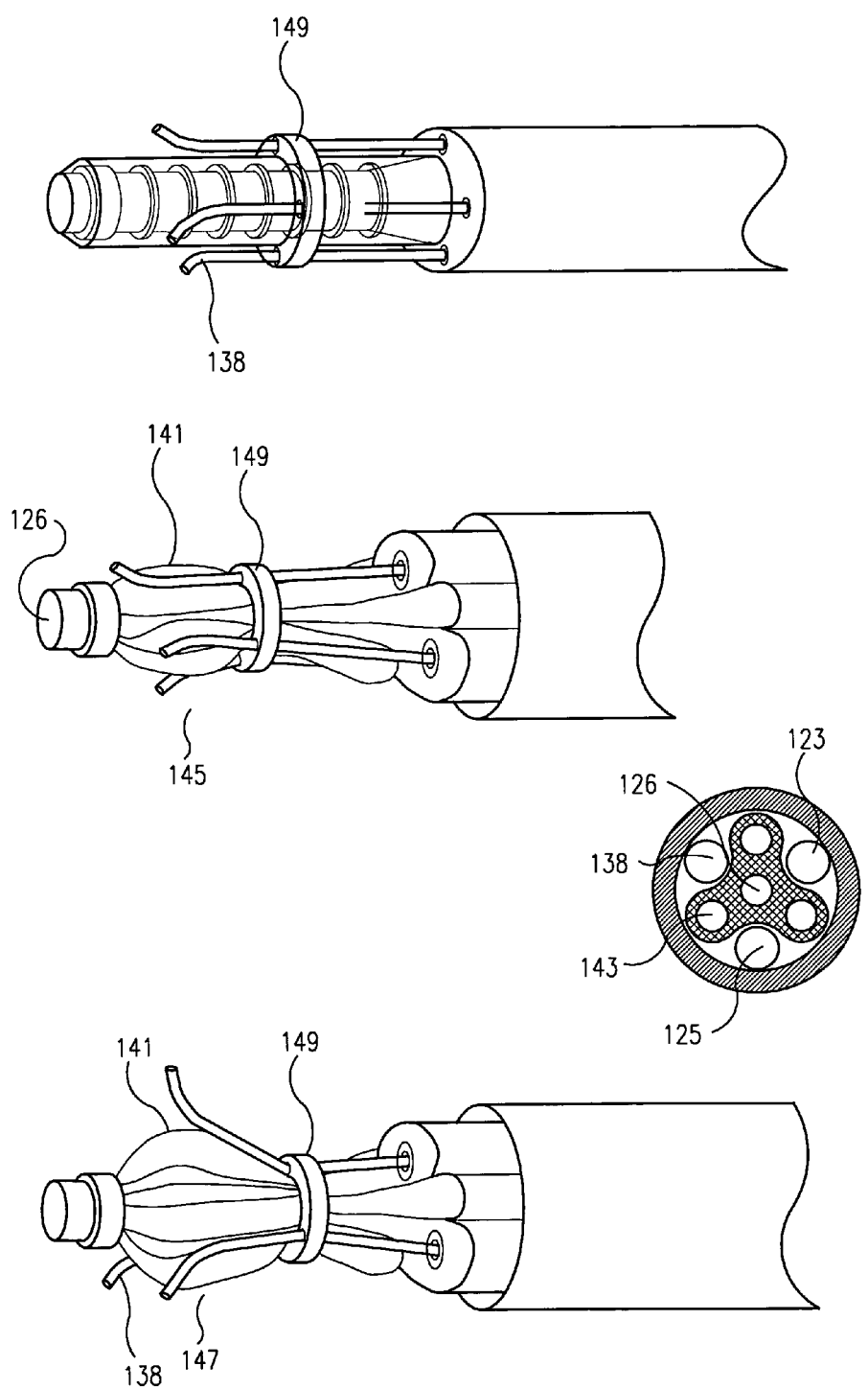
FIG. 15D illustrates a catheter assembly having multiple needles that can be directed to target sites using a balloon system.

FIG. 15D illustrates that in one embodiment, all of the needles (e.g., 3) included in the catheter assembly 100 may have divergent angled tip sections as they are extended out of their respective needle tubes. This embodiment allows for better injection zone diameter and better injection track length. Additionally, each of the needles (e.g., the needle 138) is angulated toward the sidewall near the exit opening of the catheter shaft 101. Alternatively, each of the respective extendable needle tubes that houses the individual needle can also be angulated toward the sidewall near the exit opening such that the needle will be directed out at an angle with respect to the catheter shaft 101 axis. The needle may extend independently or together with a joint 149 at the distal tip. In FIG. 15D, all of the three needles are attached to the joint 149 thus, they can all be extended together. With each needle having the angulated needle tip section, the injection zone and injection track length for these needles are improved.

In another embodiment, an inflatable balloon 141 is incorporated on the outer wall of the tendon lumen 126. The balloon 141 is placed underneath the needle sheaths that house the needles. By inflating the balloon 141, the needles (e.g., the needle 138, 123, and 125) are pushed sideways and, therefore, extending out at an angle to the central axis. As illustrated in FIG. 15D, when the balloon 141 is in the deflated state 145, the needles are not projected outward, and when the balloon 141 is in the inflated state 147, the needles are projected outward. The balloon 141 may include at least one balloon lumen 143 that allow for the inflation of the balloon 141. Alternatively the balloon 141 may have sections with individual inflation lumens 143 such that each section may be independently inflated. Thus, individual needles can be independently controlled.

In one embodiment, to increase injection points on each needle, instead of having one injection hole at the end, more holes or openings can be created on the side of each needle. Therefore, the injected agent will be more diffused instead of concentrated in one spot.

FIG. 16 illustrates an exemplary embodiment of a deflectable catheter assembly 400 where a needle is wrapped around a tendon. The catheter assembly 400 provides a balanced distribution of the internal components.

When the catheter assembly, which includes a catheter shaft and internal components, is used in the vasculature, such as going through the aortic arch and into the left ventricle, tortuosity is encountered. For a catheter assembly resident in a tortuous section of the vasculature, such as the aortic arch, the catheter shaft's torque response can easily be affected by any unbalanced force/moment created due to asymmetrically located internal components. For example, if an internal component such as a needle is located off-center, the side of the catheter shaft where the needle resides (referred to as the needle side) is stiffer than the non-needle side. The catheter shaft will "prefer" to lie over the bent vessel section with the stiffer side sitting on the outside of the bend curve. Having the stiffer side on the outside, versus inside, of the bend curve results in the lowest energy state and is, therefore a stable position. If the catheter operator attempts to rotate the catheter with its stiffer side away from the stable position, for example as to direct the catheter distal section from one ventricular wall to the other, the catheter will "whip."

Whipping is caused by the increased resistance of the catheter shaft inside a curved conduit (e.g., the Aorta, or other tortuous anatomy) to turning away from its preferred orientation and by the decrease resistance of the catheter shaft to turning toward its preferred orientation. This preferred orientation can be generated by unbalanced stiffness (flexural modulus) over the cross-section of the catheter shaft and/or by any natural or induced curvature of the catheter shaft. For example, in a catheter assembly that has a needle running through a central lumen within the catheter shaft, the tendon is placed off-center. As can be imagined, the cross-section of the catheter shaft now has an unbalanced cross-section created by the tendon and its lumen construction. If the tendon assembly is stiffer (higher flexural modulus) than the other shaft materials at similar radial positions, the tendon assembly will have a tendency to stabilize itself toward the outside of the curve. If the tendon assembly is less stiff (lower flexural modulus) than the outer shaft materials at similar radial positions, the tendon assembly will have a tendency to stabilize itself toward the inside of the curve. The preferred orientation of the shaft is the lowest stored energy state of the catheter shaft and is, therefore, a stable orientation. An orientation of 180-degrees from the preferred orientation is the highest stored energy state of the catheter shaft and is, therefore, an unstable orientation. Of course, multiple stiffer/less stiff radial shaft sections can result in multiple preferred orientations and therefore, multiple stable and unstable orientations at various angles or rotation. The greater the difference between adjacent high and low energy storage states during catheter shaft rotation, the greater the whipping or degree of rotational instability near the high energy storage peaks and the greater the resistance to turning away from the low energy storage valleys.

This problem becomes more pronounced when the tendon is pulled to deflect the distal section. Turning of the catheter now has to work against not just the preferred orientation due to unbalanced cross-sectional stiffness, but also against the compression load occurring preferentially on one side of the catheter shaft (the side with the tendon). This unbalanced compression load can also be thought of as bending moment applied the shaft. In a curved conduit, the preferred orientation (lowest catheter shaft stored energy state) is with the more compressed side of the catheter shaft oriented toward the inside of the curve. As the catheter shaft is turned away from this preferred orientation, the relatively fixed length of the tendon causes the shaft to be further compressed, as the path length of the tendon lumen tends to increase toward the outside of the curve. This can dramatically increase the energy storage of the catheter shaft, creating a large arc of rotational instability (whipping) around where the tendon side of the catheter shaft is oriented toward the outside of the curve. As a result, it is very difficult to rotationally manipulate a catheter with unbalanced stiffness or compression over the shaft cross-section. These forces are typically generated by the asymmetrically located tendon and/or needle components, for example, as in the embodiments discussed with respect to FIG. 2.

As illustrated in FIG. 16, in one embodiment, a tendon assembly 403 is located approximately in the center of the catheter shaft and a needle assembly 401 is wrapped around the tendon assembly. The construction of the catheter assembly 400 is similar to that of the catheter assembly 100 described above in many aspects. One difference between the catheter assembly 400 and the catheter assembly 100 is that in the catheter assembly 400 the needle assembly 401 is wrapped around the tendon assembly 403 along a section of the catheter proximal section 412. In addition, the tendon assembly 403 and the needle assembly 401 are free-floating within the catheter shaft of the catheter assembly 400. Further, the tendon assembly 403 and the needle assembly 401 do not reside in individual lumens. Instead, the needle assembly 401 and tendon assembly 403 are disposed within a central lumen of the catheter shaft.

The catheter assembly 400 includes a catheter proximal section 412 and a catheter distal section 414. The catheter distal section 414 is deflectable and is thus made more flexible than catheter proximal section 412. The catheter assembly 400 includes a catheter shaft 416, which is divided into two sections referred to as a proximal catheter shaft 416-P and a distal catheter shaft 416-D.

In some embodiments, the proximal catheter shaft 416-P may further be divided into a middle catheter shaft (not labeled) and the proximal catheter shaft (416-P). The middle catheter shaft is relatively more flexible compared to the proximal catheter shaft 416-P. The distal catheter shaft 416-D is the most flexible portion of the catheter shaft 416 to allow it to deflect when the tendon is pulled.

As illustrated in FIG. 16, the most outer layer in proximal the catheter section 412 is the proximal catheter shaft 416-P which functions as a torque shaft that can deliver torque from a proximal handle manipulation to the catheter distal section 414. In one embodiment, the proximal catheter shaft 416-P is made of a polymer tube reinforced with a braided layer 417, which can be made of stainless steel round wire or ribbon, nylon wire, or NiTi wire, and one or more polymer jacket layers, typically made of Nylon 12, Pebax, or Polyurethane materials.

Immediately inside of braided layers 417 of the proximal catheter shaft 416-P is a proximal core shaft 418. The proximal core shaft 418 provides a central lumen 450. The proximal core shaft 418 houses the internal components of the catheter assembly 400, couples the internal components to the proximal catheter shaft 416-P so that the entire catheter shaft can respond to torque as one body, and enhances stiffness to improve torque transmission. The proximal core shaft 418 can be made as one piece with the proximal catheter shaft 416-P. Alternatively, for ease of manufacturing, the proximal core shaft 416-P is constructed as a separate layer or constructed by building one layer on top of another layer. The proximal core shaft 418 can be constructed using polymer such as Nylon, Pebax, Polyurethane, Polyimide, and Peek. Because the proximal core shaft 418 functions as a coupling between the proximal catheter shaft 416-P and the internal components, choosing a material that is bondable to its neighbors is advantageous.

To assemble the proximal core shaft 418 underneath the proximal catheter shaft 416-P with a bond, one can first extrude the proximal core shaft 418 as a tube, braid over the tube to form the braided layer 417, and heat fuse a polymer layer over the braided layer 417. In one embodiment, a heat fusion process, which is commonly used in catheter manufacturing, is used. In this embodiment, the tube is reformed under a heat source while being supported by a mandrel and an outer shrink tube. The mandrel defines the final size for the central lumen 450 and the outer shrink tube controls polymer flow and helps defining the final size (outer diameter) for the proximal catheter shaft 416-P. The heat fusion process melts the polymer from polymer layer to encapsulate the braided layer 417 and bonds the proximal core shaft 418 to the inner wall of the proximal catheter shaft 416-P. To maintain integrity of the central lumen 450, the proximal core shaft 418 should have sufficient combined wall thickness and material stiffness. In one embodiment, with stiff material such as Polyimide, the inner wall of the proximal catheter shaft 416-P can be thinner such as 0.003" to 0.006" per side. With less stiff material such as Pebax, the inner wall should be thicker such as 0.004" to 0.012" per side. Alternatively, this inner wall layer can also be constructed with braid or coil reinforced polymer tube.

FIG. 16 illustrates that in one embodiment, the catheter proximal section 412 includes two anchoring members 428 and 430 located inside of the central lumen 450. The anchoring members 428 and 430 position and secure the tendon assembly 403 and the needle assembly 401 to the two ends of the proximal catheter shaft 416-P. In addition, the anchoring members 428 and 430 function to place and hold the needle assembly 401 and the tendon assembly 403 in relative location to each other without adding too much of stiffness. As illustrated, the anchoring members 428 and 430 are constructed such that they position the tendon assembly 403 approximately at the center and the needle assembly 401 off-center of the proximal catheter shaft 416-P. The anchoring members 428 and 430 include openings or slots that allow the tendon assembly 403 and the needle assembly 401 to be disposed therethrough. The tendon assembly 403 and the needle assembly 401 have some freedom to move in the proximal catheter shaft 416-P that is between the anchoring members 428 and 430. The tendon assembly 403 and the needle assembly 401 can dynamically distribute themselves to accommodate the change in catheter length due to presence of anatomic curvature, instead of shortening or stretching their physical lengths. Such freedom is beneficial for the catheter assembly 400 when the catheter has to travel within tortuous anatomy. In addition, such freedom provides a better controlled rotation response for the catheter assembly 400.

The material used to construct the anchoring members 428 and 430 is a low hardness durometer material that is compatible in bondability with the proximal core shaft 418. In one embodiment, the material used to make the anchoring members 428 and 430 is the same material as the one used to make the proximal core shaft 418 (e.g., polyimide or Pebax) except that a lower durometer version is used to provide the anchoring members 428 and 430 with more flexibility. In one embodiment, the anchoring member 430 can be made longer than the anchoring member 428 since that section of the proximal catheter shaft 416-P lies on a relatively straight section of the vasculature during use.

The catheter distal section 414 includes a distal catheter shaft 416-D and a compression cage 446. The distal catheter shaft 416-D acts as an outer packaging layer for the internal components of the catheter assembly 400 that are housed in the catheter distal section 414. The distal catheter shaft 416-D is made of material similar to the proximal catheter shaft 416-P except with lower durometer. For example, when the proximal catheter shaft 416-P is made with a high durometer such as Nylon 12 or Pebax72D, the distal catheter shaft 416-D can be made of Pebax40D, a blend of Pebax40D. The compression cage 446 is disposed immediately within the distal catheter shaft 416-D. The compression cage 446 is similar to the compression cage 122 of the catheter assembly 100 and similar to those compression cages described with reference to FIGS. 11A-11E. The compression cage 446 can also be replaced with the helical coil structure 165 shown in FIG. 12 above.

In addition, the distal catheter shaft 416-D includes a distal tip anchor 444 and a transition section 402. The distal tip anchor 444 seals the catheter shaft 416 and also functions to anchor the tendon 436. The distal tip anchor 444 includes an exit opening 470 for the needle 438 to be extended therethrough to reach a target site. The transition section 402 defines the deflection transition point for the catheter assembly 400. The catheter distal section 416-D, starting at the transition section 402, will deflect under the tension from the tendon 436.

In the transition section 402, the tendon 436 is shifted from the center of the catheter shaft 416 to being off-center at the transition section 402 thus, creating a bending moment when the tendon 436 is pulled. As mentioned, the distal catheter shaft 416-D is made much more flexible compared to the proximal catheter shaft 416-P thus, creating a bias for deflection under the tension from the tendon 436. In some embodiments, in addition to the change in the tendon 436 location, the needle 438 is moved toward the center of the distal catheter shaft 416-D at the transition section 402.

The transition section 402 includes a transitioning member 442, which is made of material similar to the anchoring members 428 and 430 and is coupled to the compression cage 446. The transitioning member 442 provides similar functions to those provided by the anchoring members 428 and 430. The transitioning member 442 secures the positions of the tendon assembly 403 and the needle assembly 401 within the transition section 402. As illustrated, the transitioning member 442 is constructed such that it transitions and positions the tendon assembly 403 off-center and the needle assembly 401 approximately in the center of the distal catheter shaft 416-D.

The proximal catheter shaft 416-P is coupled to the distal catheter shaft 416-D. The proximal catheter shaft 416-P is bonded to the distal catheter shaft 416-D to form the continuous catheter shaft 416. Adhesive, cyanoacrylate adhesive, epoxy, or equivalent materials can be used to bond the distal catheter shaft 416-D to the proximal catheter shaft 416-P. Optimally, the internal components of the catheter assembly 400 are placed in position first and a heat fusion process is then used to bond the distal catheter shaft 416-D to the proximal catheter shaft 416-P.

FIG. 16A illustrates that in one embodiment, a needle assembly 401 is disposed within the central lumen 450 and is wrapped around the tendon assembly 403 along the proximal catheter shaft 416-P. More needle assemblies 403 can also be included in the catheter assembly 400 without deviation from the scope of the embodiment. Similar to the catheter assembly 100, other therapeutic tools besides the needle assembly 401 can also be included in the catheter assembly 400. When more than one needle assembly 401 is used, they can all be wrapped around the tendon assembly 403. Alternatively, when more than one needle assembly 401 is used, they can all be disposed within one needle sheath which is then disposed within the central lumen 450 and wrapped around the tendon assembly 403. Alternatively, when more than one needle assembly 401 is used, each can be disposed within one individual needle sheath and all sheaths are then disposed within the central lumen 450 and wrapped around the tendon assembly 403.

When the catheter assembly 400 is expected to reside in tortuous anatomy, part of the needle assembly 401 is on the outside of the bend curve and part of the needle assembly 401 is on the inside of the curve. Therefore, the asymmetric stiffness is relatively balanced over the curved sections. For this to work effectively, it is important to have sufficient number of wraps over a section length that is expected to lie across a bend region in the vasculature. In one embodiment, the number of wraps needed to balance the needle assembly stiffness for the exemplary embodiment shown in FIG. 16A may be at least 1 complete wrap for every 5 to 20 cm proximal catheter shaft 416-P length. The shaft section where the wraps are placed is also important. The wraps should be placed on the shaft section where a major curvature, such as the aortic arch, is expected to encounter during the use of the catheter in the vasculature.

Wrapping of the needle assembly 401 around the tendon assembly 403 also addresses a length change issue occurring in an off-center needle. When the catheter is placed over a bend region in the vasculature, the catheter shaft section near the inside of the bend curve compresses while the section near the outside of the bend curve stretches. The (non-wrapping) needle assembly located off-center may change its length dependent on its location relative to the curvature. This creates a problem for controlling precise needle extension. By wrapping the needle assembly 401 around the tendon assembly 403, the length change is relatively balanced between the inside curve versus the outside curve locations.

In an alternative embodiment, instead of wrapping the needle assembly 401 around the tendon assembly 403, the opposite may be constructed having the tendon assembly 403 wrapping around an approximately centrally located needle assembly 401 as shown in FIG. 16B. The needle assembly 401 will be the component that includes an axial spine. Since the needle assembly 401 is located in the center, the path length of the needle 438 will not change due to its neutral location. The wrapped assemblies (the needle assembly 401 and the tendon assembly 403) help balance the moments generated by pulling the tendon 436 and thus, balance catheter shaft compression.

In an alternative embodiment, the tendon assembly 403 and the needle assembly 401 are twisted about each other. The embodiment is especially helpful in the case where one assembly is not significantly stiffer than the other and puts the assembly at the center of the catheter in the areas where residence in torturous anatomy is expected.

The following sections discuss in details exemplary constructions of the needle assembly 401, the tendon assembly 403, and the catheter shaft 416.

The needle assembly 401 includes a needle 438 and a low-friction or lubricious needle sheath 440 (FIG. 16A). The needle 438 can be a conventional needle known in the art. The needle 438 can be made of a NiTi tube with a straight lumen diameter. The needle 438 can also be made of stainless steel or other metallic alloy, or stiff polymer such as a braid reinforced Polyimide. The distal end of the needle is beveled to a sharp point for ease of piercing or puncturing into a target tissue. For a polymer needle, the tip is still preferred to be beveled metallic structure for ease of piercing or puncturing. The metallic tip and the polymeric body can be joined together by adhesive or other suitable materials. In one embodiment, the needle 438 tip includes a radio-opaque material for visibility of the needle 438 tip during delivery procedures. The radio-opaque material can be incorporated into the needle 438 tip by using method such as plating or coating with gold, Platinum/Iranium alloy, or other suitable radio-opaque material. The needle sheath 440 is typically made of a low-friction material such as a polymer having lubricious lumen surface (e.g., PTFE or TEFLON, HDPE, or braid and coil reinforced polymer).

The tendon assembly 403 comprises of the tendon 436 disposed within a tendon sheath 423. In one embodiment, along the proximal catheter shaft 416-P, the tendon sheath 423 is an axial spine 420. Along the distal catheter shaft 416-D, the tendon sheath 423 is a flexible tendon sheath 421. The axial spine 420 is stiff and not compressible whereas the flexible tendon sheath 421 is flexible and soft. One reason for the difference in sheath properties is that the tendon 436 needs to transmit torque along the catheter proximal section 412 thus, the tendon sheath 423 needs to be stiff and not compressible. On the other hand, the tendon 436 needs to be able to deflect the catheter distal section 414 thus, the tendon sheath 423 needs to be flexible, which is indicated by the reference flexible tendon sheath 421.

The flexible tendon sheath 421 is typically made of a low-friction material such as a polymer having lubricious lumen surface (e.g., PTFE or TEFLON, HDPE, co-extruded polymer tube with lubricious inner layer polymer, or braid and coil reinforced polymer). The axial spine 420 is made of materials that allow it to resists catheter compression when the tendon 436 is pulled to deflect the catheter distal section 414 (e.g., stainless steel or Nitinol).

In an alternative embodiment, the tendon sheath 423 includes only the flexible tendon sheath 421 that runs the entire length of the catheter shaft 416. Thus, the flexible tendon sheath 421 replaces the axial spine 420 at the proximal catheter shaft 416-P. A stacked coil structure 425 (FIG. 17) is placed over the flexible tendon sheath 421 along the section that is within the proximal catheter shaft 416-P. In one embodiment, the stacked coil tendon sheath 425 is a metal made of stainless steel or other metallic alloys. The stacked coil tendon sheath 425 provides similar functions as the axial spine 420 to provide resistance to catheter compression when the tendon 436 is pulled to deflect the catheter distal section 414.

In addition, the tendon assembly 403 includes two sets of slip bands 424 and 426 mounted on both ends of the axial spine 420 (FIG. 16A). The ends of the axial spine 420 with the slip bands 424 and 426 are indicated as a section 404 and a section 410, respectively. The slip bands 424 and 426 couple the axial spine 420 to the anchoring members 428 and 430 respectively. Together with the anchoring members 428 and 430, the slip bands 424 and 426 act to anchor the tendon assembly 403 in place and help hold the length of the catheter proximal section 412 constant, when the tendon 436 is being pulled. The slip bands 424 and 426 can be made of metallic tubes, bands, or rings. The slip bands includes openings so that materials from the anchoring members 428 and 430 can be dispersed therethrough to create bonding for the slip bands 424 and 426 to the anchoring members 428 and 430.

In another embodiment, slots can be cut into the wall of the axial spine 420, without the slip bands 424 and 426, so that materials from the anchoring member 428 and 430 can be dispersed therethrough to create an interference lock for anchoring the axial spine 420 to the anchoring members 428 and 430.

The following sections describe in details exemplary methods of constructing the catheter assembly 400.

Figure 18:
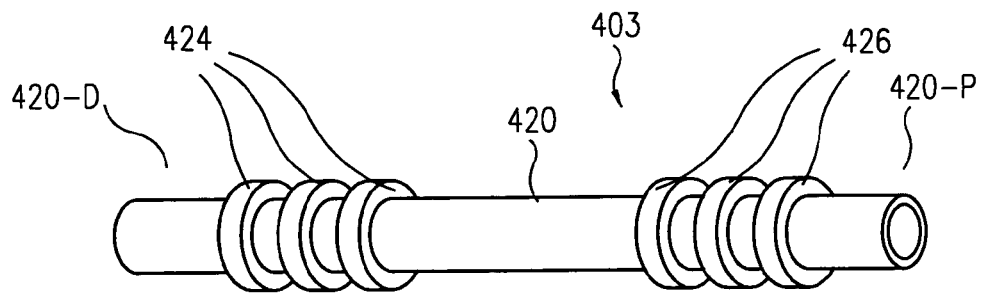
FIGS. 18-19 illustrate the preparation of a tendon assembly.
Figure 19:
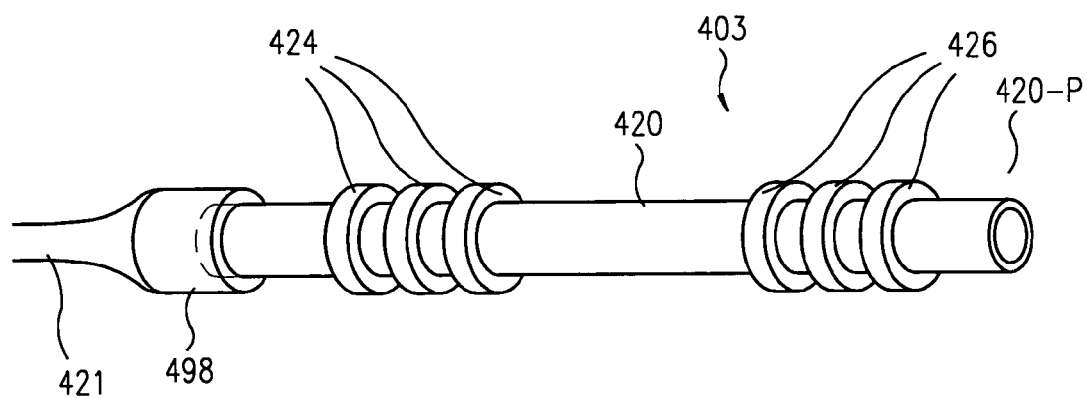

Beginning with FIG. 18, the tendon assembly 403 is prepared. The slip bands 424 are bonded to ends 420-D and the slip bands 426 are bonded to ends 420-P of the axial spine 420. In one embodiment, adhesive is used to bond the slip bands 424 and 426 to the axial spine 420. In FIG. 19, the flexible tendon sheath 421 is coupled to the distal end of the axial spine 420 with an overlapping section 498. In one embodiment, adhesive is dispensed between the axial spine 420 and the tendon sheath 421 at the overlapping section 498. In alternative embodiments, openings (not shown) may be created into the flexible tendon sheath 421 at the overlapping section 498 and adhesive is dispensed into the openings to create a bond between the axial spine 420 and the flexible tendon sheath 421. A mandrel (not shown) is inserted into the inner lumen of the flexible tendon sheath 421 to keep the lumen open in subsequent heat processes.

Figure 20:
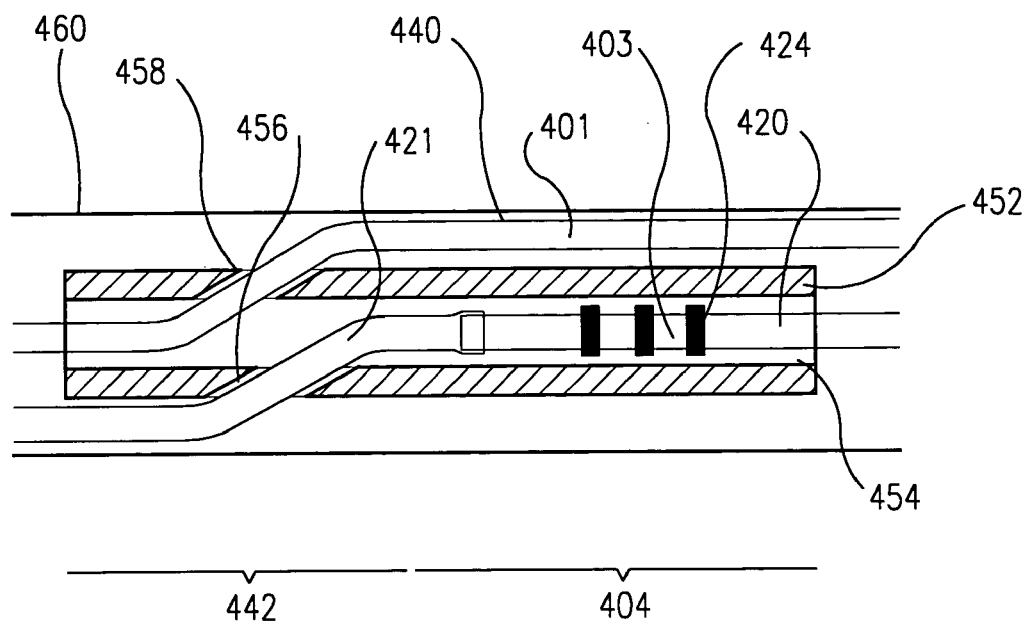
FIG. 20 illustrates the preparation of a transitioning member and an anchoring member of a catheter assembly.

Next, in FIG. 20, the transitioning member 442 and the anchoring member 428 are prepared. The transitioning member 442 and the anchoring member 428 are prepared with the tendon sheath 423 (which includes the flexible tendon sheath 421 and the axial spine 420) and the needle sheath 440 embedded therewith. In one embodiment, an extruded polymer tube 452 is used to form the transitioning member 442 and the anchoring member 428. The polymer tube 452 has a central lumen 454. Two openings are created into the polymer tube 452 on opposite sides longitudinally spaced lightly apart. As shown in FIG. 20, a first opening 456 and a second opening 458 are created and located opposite of each other. In FIG. 20, the axial spine 420 having the slip bands 424 and lap-joined to flexible tendon sheath 421 for the tendon assembly 403 (as prepared in FIG. 19) is placed in the central lumen 454 of the polymer tube 452 for a distance about equal to the length of the section 404 (FIG. 16A). At the section where the axial spine 420 terminates into the flexible tendon sheath 421, the flexible tendon sheath 421 is moved so that it exits to the outside of the polymer tube 452 through the first opening 456. The needle sheath 440 also having a mandrel supporting the inner lumen (not shown), for the needle assembly 401 is placed on the outside of the polymer tube 452 until it passes the section having the slip bands 424 (or section 404). After the section 404, the needle sheath 440 is placed into the central lumen 454 via the second opening 458. A shrink tube 460 is placed over the tube 452 after the tendon sheath and the needle sheath 440 are placed in their proper locations. Heat is then applied over the shrink tube 460. As the polymer from the tube 452 melts, the assembly placed outside of the tube sinks into the wall of the tube 452 but the assembly placed in the center lumen of the tube 452 stays approximately center. The lumen support mandrels (not shown) keep the inner diameter of the flexible needle sheath 421 and the needle sheath 440 open during the heat fusion process. This forms the anchoring member 428 and the transitioning member 442.

Next, the tendon sheath 423 for the tendon assembly 403 and the needle sheath 440 for the needle assembly 401 are wrapped around each other. As illustrated in FIG. 16, the tendon sheath 423 and the needle sheath 440 only wrap around each other at the section that is within the proximal catheter shaft 416-P. In one embodiment, the needle sheath 440 is wrapped around the axial spine 420 of the tendon assembly 403.

Next, the anchoring member 430 is prepared so that it embeds the needle sheath 440 of the needle assembly 401 and the axial spine 420 of the tendon assembly 403. The anchoring member 430 is formed similarly to the anchoring member 428 except that no opening similar to the openings 456 and 458 are needed. The axial spine 420 having slip bands 426 is placed inside a polymer tube similar to the tube 452 (in a central lumen similar to the lumen 454). The needle sheath 440 is placed on the outside of the polymer tube. A shrink tube is placed over the polymer tube after the axial spine 420 and the needle sheath 440 are placed in their proper locations. Heat is then applied over the shrink tube. As the polymer from the tube melts, the assembly placed outside of the tube sinks into the wall of the tube but the assembly placed in the center lumen of the tube stays approximately center. This forms the anchoring member 430 having the axial spine 420 and needle sheath 440 embedded therewith. At this point, the internal components for the catheter shaft 416 are assembled.

Figure 21:
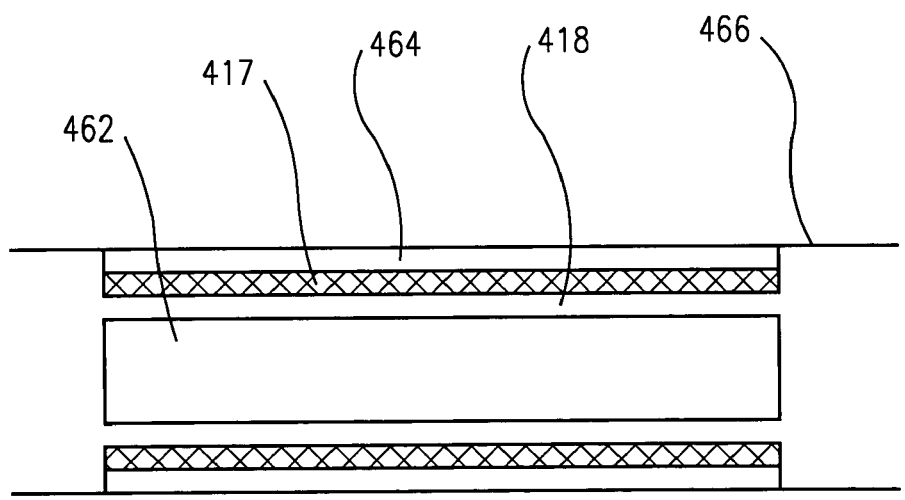
FIG. 21 illustrates the preparation of a proximal core shaft of a catheter assembly.

Next, the proximal core shaft 418 is prepared as shown in FIG. 21. An extruded tube for the proximal core shaft 418 is provided. A mandrel 462 is inserted into the lumen of the extruded tube for the proximal core shaft 418. A braided layer 417 is placed on the top of the proximal core shaft 418 extrusion. A polymer tube 464 is placed over the braided layer 417. A shrink tube 466 is placed over the polymer tube 464. The shrink tube defines the outer diameter of the proximal catheter shaft 416-P. Heat is then applied over the shrink tube 466 to fuse the polymer 464 into the braided layer 417. After the heat fusion process, the shrink tube 466 and the support mandrel 462 are removed. At this point, the proximal catheter shaft 416-P is prepared and can also be seen in FIG. 16A.

Next, the internal component assembly as prepared above is inserted into the proximal shaft 416-P to give the structure shown in FIG. 16A. In one embodiment, the internal component assembly and the proximal catheter shaft 416-P are bonded together on both ends over the slip band areas 404 and 410 using adhesive or a heat fusion process. When adhesive is used, openings (not shown) can be created through the proximal shaft 416-P and adhesive can then be dispensed through the openings to fill in the space between the internal component assembly and the proximal catheter shaft 416-P.

Figures 22, 23:
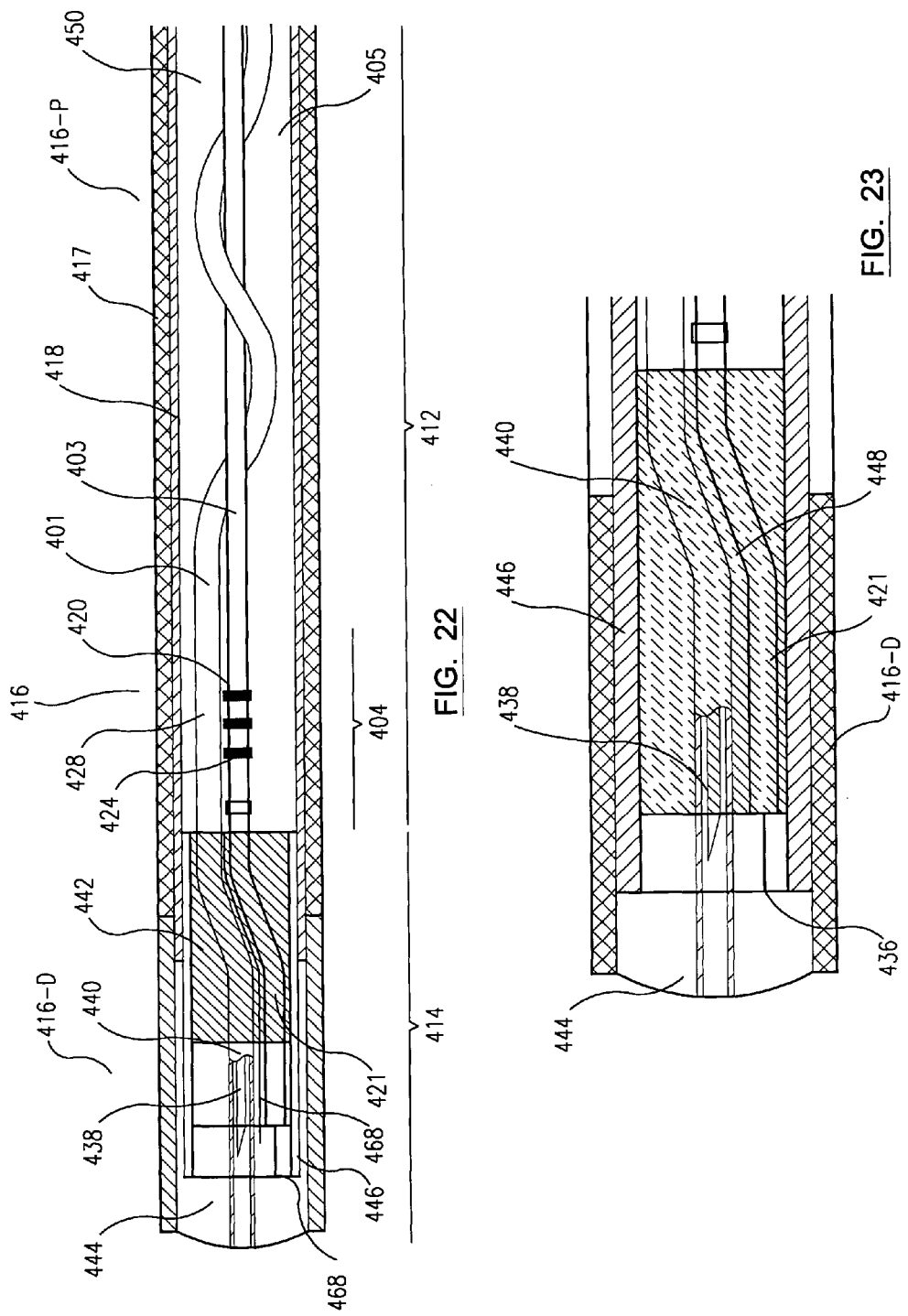
FIG. 22 illustrates another exemplary catheter assembly.
FIG. 23 illustrates the catheter distal section of a catheter assembly.

Next, the distal catheter shaft 416-D is prepared. As shown in FIG. 16A, the distal catheter shaft 416-D includes a compression cage 446 disposed immediately within the distal catheter shaft 416-D. In one embodiment, a filler material 448 is used to fill the space inside of the compression cage 446 (FIG. 23). The filler material 448 is used to hold or anchor the flexible tendon sheath 421 and the needle sheath 440 in placed in the distal catheter shaft 416-D. For example, the filler material 448 helps to hold the flexible tendon sheath 421 (and hence the tendon 436) off-center of the distal catheter shaft 416-D. The filler material 448 can be formed in the same step as that of the transitioning member 442. In one embodiment, the proximal end of the compression cage 446 is coupled to the transitioning member 442 but it is not in physical attachment to the filler section. In one embodiment, the filler material 448 is physically fused (attached) onto the needle sheath 440 and the flexible tendon sheath 421. In another embodiment, the filler material 448 is not physically fused (attached) onto the needle sheath 440 and the flexible tendon sheath 421 in the middle section between the ends of the catheter distal section 414. The slight separation provides additional flexibility and freedom of movement for the catheter distal section 414 and prevents physical pulling of the needle sheath 440 during deflection. The distal end of the filler material 448, in both embodiments ends right proximal to tip anchor 444. Having the filler material 448 also prevents kinking in the distal catheter shaft 416-D.

In one embodiment, a wall 468 (FIG. 22) is placed between the needle sheath 440 and the flexible tendon sheath 421. The wall 468 may be used instead of the filler to hold the tendon sheath 421 off-center of the distal catheter shaft 416-D. The wall 468 can be made of flexible NiTi ribbon, polymer ribbon such as Peek or polyimide. Both ends of the wall 468 are fixed to the inner components of the distal catheter shaft 416-D. On the proximal end of catheter distal section 414, the wall 468 is trapped within the transitioning member 442 in between the flexible tendon sheath 421 and needle sheath 440. On the distal end of the section 414, the ribbon is trapped within a groove (not shown) on the distal tip anchor 444.

After the flexible tendon sheath 421 and the needle sheath 440 are placed in their proper locations, a polymer layer is placed over the compression cage 446. A shrink tube is placed over the polymer layer. Heat is then applied to the catheter distal section to fuse the layers together to complete the distal catheter shaft 416-D. In one embodiment, heat is only applied to the distal end and the proximal end of the polymer layer and the compression cage 446. Thus, only the proximal end and the distal end of the compression cage 446 are fused to the polymer giving the distal catheter shaft 416-D more flexibility in the middle section.

The tendon 436 is inserted within the catheter shaft 416. The tendon 436 is only inserted into the catheter shaft 416 after all the internal components of the catheter shaft 416 are assembled into the catheter shaft 416. The distal tip anchor 444 is coupled to the compression cage 446 and the distal catheter shaft 416-D, for example by, adhesive, welding, soldering, crimping, mechanical interference, etc. In one embodiment, the distal tip anchor 444 functions as a tendon anchor. The tendon 436 is coupled to the wall of the distal tip anchor 444 by adhesive, welding, soldering, crimping, mechanical interference, or other suitable technique. The tendon 436 is then inserted into the tendon sheath 421 and is pushed proximally through the axial spine 420 until the tendon 436 reaches the proximal catheter shaft 416-P and extends out of the proximal catheter shaft 416-P.

The needle 438 is disposed within the needle sheath 440. The needle 438 extends from the distal end of the catheter shaft 416 to outside of the proximal catheter shaft 416-P. The distal end of the needle sheath 440 can be bonded to the distal tip anchor 444 using, for example, adhesive.

In some embodiments, certain therapeutic procedures for detection of the physioelectrical signal along with biologic delivery are desired. In these embodiments, the distal tip anchor 444 can be converted to a tip electrode similar to that described in catheter assembly 100. Additional band electrode can be added to a location a few millimeters proximal to the tip electrode similar to the catheter assembly 100 previously described. Having both electrodes will allow for sensing of near field bipolar signals, which greatly reduces the noise to signal ratio. The conductor wires from the electrodes will run within the catheter shaft 416. Wrapping of these wires around the central component (either the tendon sheath or the needle sheath) is beneficial but not always necessary. Dependent on the size of the wires, their mass may be so small such that they need not be wrapped about the tendon assembly 403, or alternatively, the needle assembly 401, to prevent a rotation problem.

In procedures where a therapeutic tool is used in the heart chamber, having the ability to guide the catheter delivery will greatly improve dose accuracy. MRI is one option for guiding a catheter assembly similar to the catheter assembly 400. The catheter assembly 400 can be made compatible with MRI scanner by replacing its ferrous (e.g., stainless steel) material with non-ferrous but functioning material. In one embodiment, the tendon 436 is replaced with NiTi in cold work condition. In another embodiment, the braided layer 417 is replaced by Nylon ribbons and the slip bands 424 and 426 are replaced by slots cutting into the axial spine 420 wall or material such as platinum.

The catheter assembly 400 described provides multiple benefits for balancing moments and needle path length changes generated by asymmetrically located components and needle path length changes. This results in superior rotation response and precise needle extension control for the catheter.

In some applications, variable deflection length of a deflectable catheter assembly such as the deflectable catheter assembly 100 or the deflectable catheter assembly 400 is extremely useful. Fixed deflectable length may make it more difficult to navigate the catheter assembly within the patient such as navigating in the ventricle of the patient. For example, the long deflected tip of the catheter assembly may get entangled easily with the ventricular cords. Furthermore, as the catheter assembly enters the ventricle through the aortic valve, it may be very difficult to rotate the long deflected tip of the catheter assembly towards the adjacent septal wall for injections. It is therefore useful during such circumstances to have a shorter deflected tip and with a longer deflected tip to provide easier access and support when targeting distant areas such as the lateral wall. It is thus advantageous to provide the deflectable catheter assembly such as the catheter assembly 100 or the catheter assembly 400 with a deflectable tip that has various deflection lengths.

Figure 24:
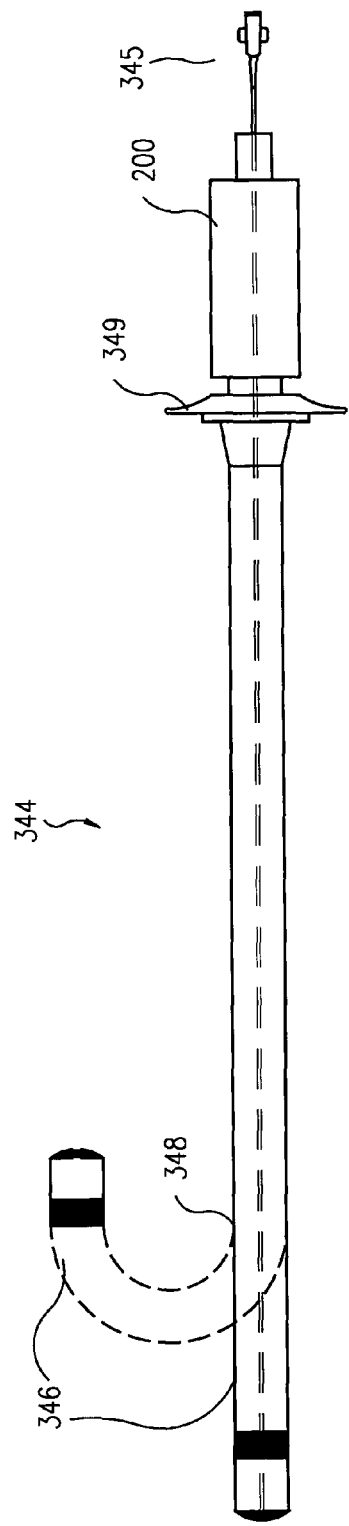
FIGS. 24-25 illustrate a deflectable catheter assembly with multiple deflection points along the catheter distal section.

FIG. 24 illustrates a deflectable catheter assembly 344 which may have similar constructions to the catheter assemblies 100 or 400 previously described. In general, the catheter assembly 344 is similar to the catheter assemblies 100 or 400 in that the catheter assembly 344 includes a catheter distal section 346 that is deflectable beginning at the deflection transition point 348. Similar to the catheter assemblies 100 or 400, the catheter assembly 344 also includes a catheter proximal section 347, which is further coupled to a handle 200 that may include an injection port 345. The internal components (e.g., a tendon assembly and needle assembly or needle assemblies) are constructed similarly to the catheter assembly 100 or 400. One thing that is provided in the catheter assembly 344 is the variable or adjustable deflection length.

In deflectable catheter assembly without variable deflection length, pulling the tendon (e.g., the tendon 130 or the tendon 436) pulls the end of the catheter assembly from the distal harness of the tendon, to deflect the catheter's distal soft section from the shaft transition point. Since the deflecting tendon is welded, anchored, or harnessed at a fixed length from the tip (e.g., from the distal anchor 444 or 140) and the flexible portion of the catheter assembly is also of a fixed length, the catheter can only be deflected from a single point, to create a deflected section of fixed length. Each catheter assembly is therefore created with a default, unalterable deflection length.

Figure 25:
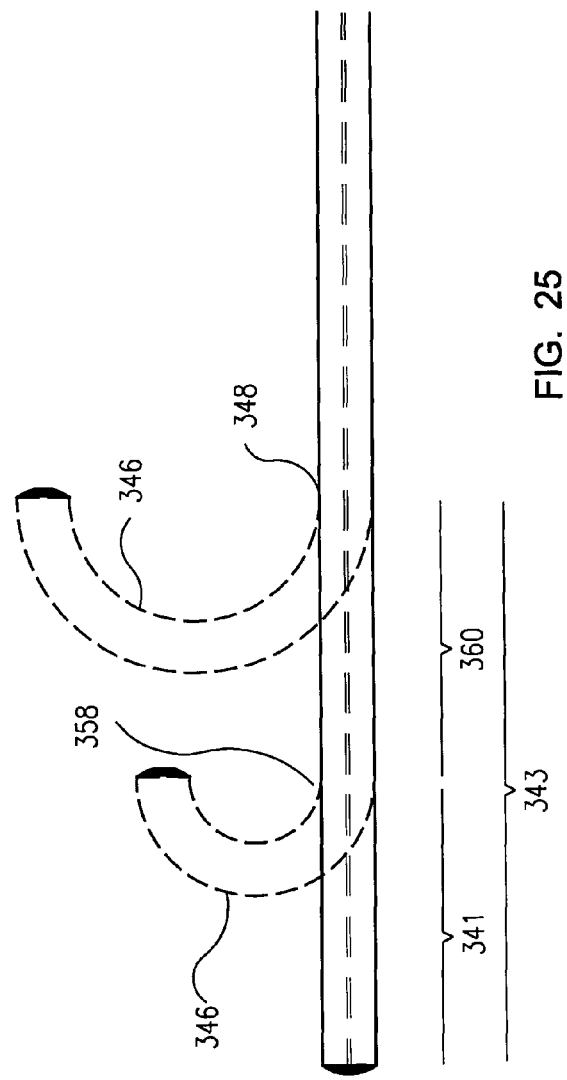

In one embodiment, the catheter assembly 344 with variable deflection lengths is achieved by varying the flexibility length of the catheter distal section 346. As illustrated in FIG. 25, the catheter distal section 346 has at least deflection lengths, 341 and 343. The variable deflection lengths can be done by moving the deflection transition point or shortening the flexible length along the catheter distal section 346. In one embodiment, the catheter assembly 344 includes a maximum deflection length beginning at the deflection transition point 348, which is pre-set for the catheter assembly 344. The deflection transition point 348 also defines a permanent transition point fixed in the catheter assembly 344. In one embodiment, the deflection length is varied by moving the deflection transition point from 348 to a deflection transition point 358 as illustrated in FIG. 25. In one embodiment, a section 360 along the catheter distal section 346, which is a section between the deflection transition point 348 and the deflection transition point 358, is made stiffer. Thus, the catheter distal section 346 will begin to deflect at the deflection transition point 358 (instead of the deflection transition point 348) since the section 360 is now stiffer.

Figure 26A:
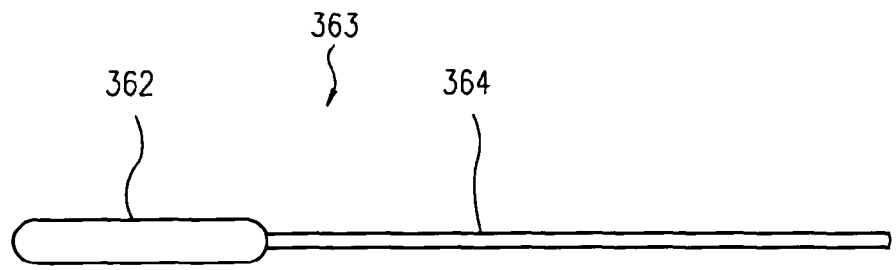
FIGS. 26A-26C illustrate a stiffening member that can be incorporated into a catheter assembly to provide multiple deflection points to the catheter distal section.
Figure 26B:
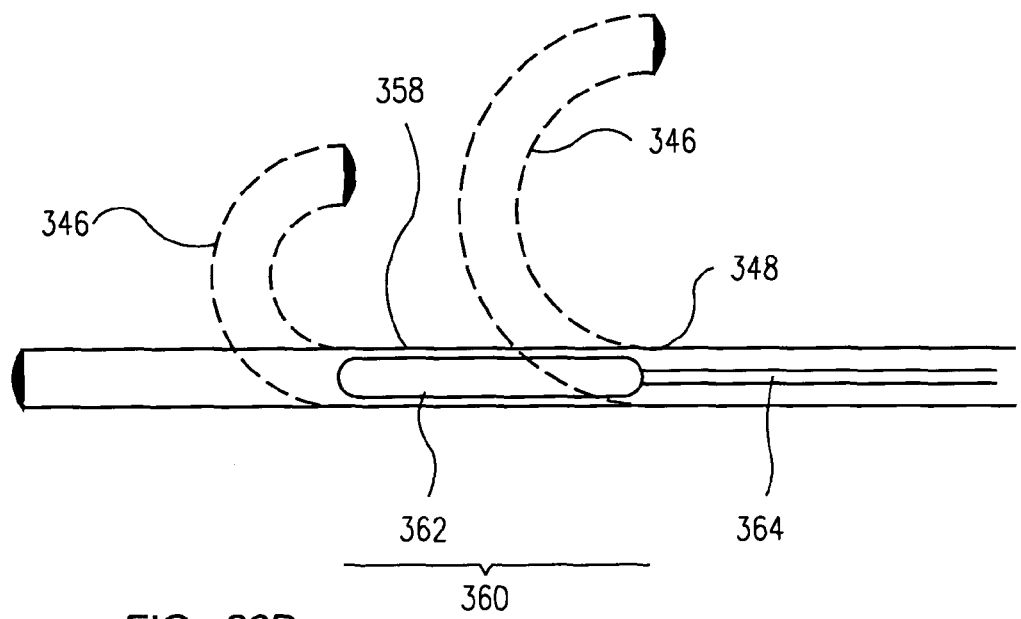

FIGS. 26A-B illustrate an exemplary stiffening component 363 that can be incorporated into the catheter assembly 344. The stiffening component 363 comprises a push wire 364 coupling to a stiffening member 362. The length of the flexible catheter distal section 346 available for deflection could be manipulated by sliding stiffening component 363 along an inner lumen of the catheter distal section causing a section (e.g., the section 360) of the catheter distal section 346 to become stiffer and unable to deflect. This creates a new deflection transition point, for example, the defection transition point 358.

In one embodiment, the stiffening component 363 is disposed within a lumen running in parallel to the lumen that houses the tendon assembly. The push wire 364 extends through the catheter shaft and extended by a control mechanism that may be included within the handle 200 to control the movement of the stiffening component 363. The stiffening member 362 is stiffer than the flexible catheter distal section 346 so that tensioning the deflection tendon would lead to a deflection of the catheter only in the region distal to the stiffening member 362. Varying the position of the stiffening member 362 relative to the distal end of the catheter assembly 344 indirectly alters the length of the deflectable catheter distal section 346. As illustrated in FIG. 26B, the stiffening component 363 is disposed within a lumen that runs parallel to a tendon assembly (not shown) and as the stiffening component 363 moves the stiffening member 362 into the section 360 of the catheter distal section 346, the deflection transition point 348 is no longer the point where the deflection for the catheter distal section 346 begins. Instead, the deflection transition point 358 becomes the point where the deflection for the catheter distal section 346 begins. The stiffening component 363 may be moved to various locations along the catheter distal section 346 distal to the deflection transition point 348 to provide the catheter 346 with variable deflection lengths.

As shown in FIGS. 26A-26B, the stiffening component 363 has a stiff and bigger distal section, the stiffening member 362. The stiffening member 362 may have a desired length that is sufficient to create a stiff section along the catheter distal section 346, e.g., a length of about 1-7 cm long. The stiffening member 362 may be made with materials such as stainless steel or combination of materials such as stainless steel for the bullet section and NiTi or composite polymer material for the pushwire 364 (reinforced polyimide, for example). The push wire 364 is sufficiently flexible so that it does not alter the stiffness or moment balance of the steerable catheter assembly 344 shaft. The push wire 364 may also be coated with lubricious coating material (e.g. Teflon, silicone, etc) to reduce friction between the lumen and the push wire 364. The push wire 364 is sufficiently long to extend to the proximal end of the catheter assembly 344 and may be controlled by the proximal handle 200 for controlled movement. In one embodiment, the lumen that houses the stiffening component 363 is about the same as the other side lumens on the non-deflectable section (the catheter proximal section 347) so that it does not alter the balance for the moment across the shaft cross-section. Distally, the lumen may become bigger to accommodate bigger stiffening member 362 for the need of achieving effective stiffness.

Figure 26C:
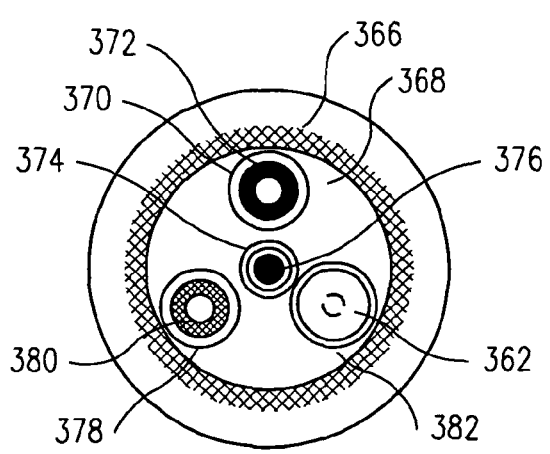

FIG. 26C illustrates cross section of the catheter proximal section 347 that illustrates an exemplary arrangement of the stiffening component 363 relative to other lumens of the catheter assembly 344. Similar to the catheter assembly 100 or 400, the catheter assembly 344 includes several lumens, 370, 378, 374, and 382. The lumen 370 can accommodate a needle assembly 372 (e.g., similar to the needle assembly 109) and the lumen 378 can accommodate another needle assembly 380 (e.g., similar to the needle assembly 105) or simply a lumen filler. The lumen 374 can accommodate a tendon assembly 376 (similar to the tendon assembly 103). The lumen 382 thus accommodates the stiffening component 363.

In alternative embodiments, an outer sheath with a stiff distal section is disposed over the catheter assembly 344 to provide the catheter assembly 344 with variable deflection lengths. In this embodiment, the outer sheath replaces the stiffening component 363.

As illustrated in FIG. 27A, an outer sheath 384 is provided. The outer sheath 384 includes a flexible section 386 and a stiffening section 388. The outer sheath 384 is disposed outside of the catheter assembly 344. The outer sheath 384 thus runs over the outer diameter of the catheter assembly 344. The location of the stiffening section 388 along the catheter distal section 346 varies the deflection transition point of the catheter assembly 344. As illustrated in FIG. 27B, the outer sheath 384 is advanced passing the original shaft transition point 348 and then the tendon of the catheter assembly 344 is pulled, the catheter deflects at a location distal to the stiffening section 388. By advancing this section into the flexible deflectable region 346 of the steerable catheter assembly 344, the stiffness in this region increases. This results in a change of deflection point to a location distal to the outer sheath 384. In one embodiment, the flexible section 384 is made just stiff enough to allow controlled movement of the outer sheath 386 from the proximal end of the catheter assembly 344.

The outer sheath 384 is made to fit with small or minimal spacing over the steerable catheter 344 so that it is free to move longitudinally. The outer sheath 384 may be constructed with polymer of different durometers reinforced with a braided stainless steel layer. Different stiffness may be achieved by varying the braid pattern as well as the durometer of the polymer. The stiffening section 388 may have a desired length that is sufficient to create a stiff section along the catheter distal section 346, e.g., a length of about 1-7 cm long. The stiffening section 388 may be constructed similarly to the flexible section 386 except with much more stiffness. The stiffening section 388 and the flexible section 386 may be constructed out of materials typically used to make a catheter shaft. The stiffening section 388 can be constructed with a high durometer material reinforced with tightly braided stainless steel. The flexible section 386 may be constructed with a lower durometer material similar to those used to make the catheter shaft 101 (catheter assembly 100) or 416 (catheter assembly 400).

Figure 28A:
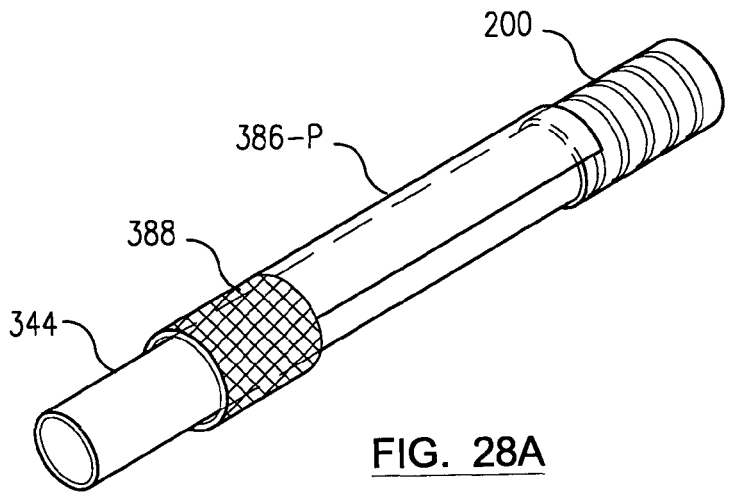
FIGS. 28A-28C and 29A-29B illustrate alternative stiffening components that can be incorporated into a catheter assembly to provide multiple deflection points to the catheter distal section.
Figure 28B:
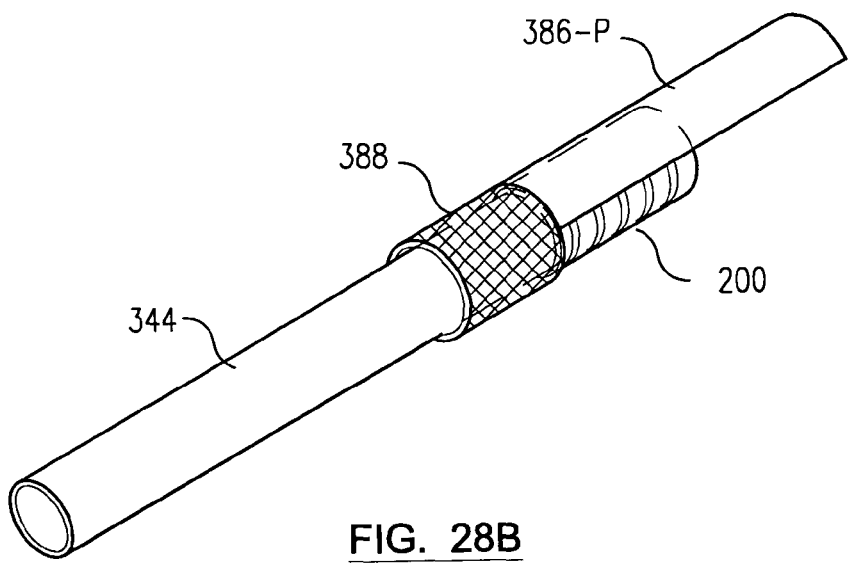
Figure 28C:
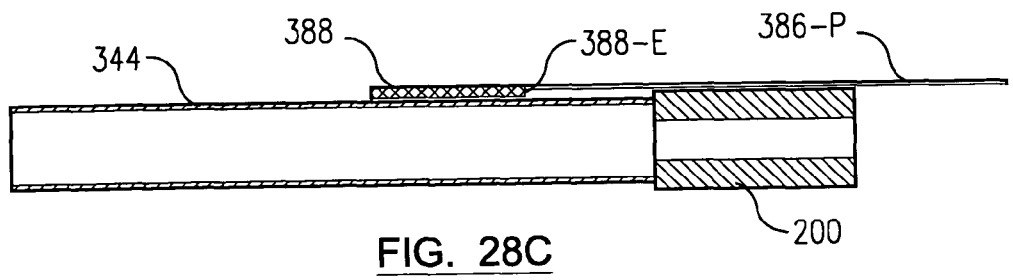

In another embodiment, the flexible section 386 is not a complete tube but is a partial tube 386-P (e.g., a tube with a crescent shaped cross-section) as shown in FIGS. 28A-28C. As shown in FIG. 28A, the catheter assembly 344 is coupled to the handle 200. Disposed outside of the distal section of the catheter assembly 344 is the stiffening member 388. The stiffening member 388 is a tube. Attached to the stiffening member 388 is the partial tube 386-P. Both the stiffening member 388 and the partial tube 386-P are moveable along the catheter shaft of the catheter assembly 344. However, the stiffening member 388 is configured so that it will not be able to slide over the handle 200. In one embodiment, the stiffening member 388 includes an interference feature 388-E that engages with the distal end of the handle 200 so that the stiffening member 388 is stopped from sliding off the handle 200 (FIG. 28C). On the other hand, the partial tube 386-P can slide over the handle 200 as shown in FIG. 28B. In this embodiment, the stiffening member 388 can be pulled out of the vasculature when not in used.

Figure 29A:
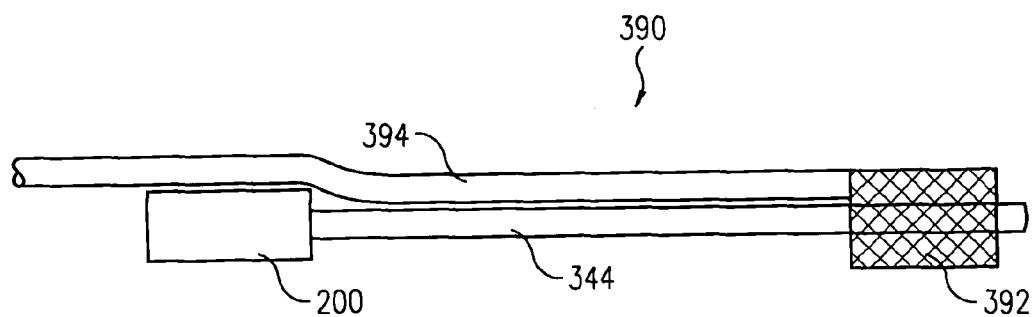
Figure 29B:
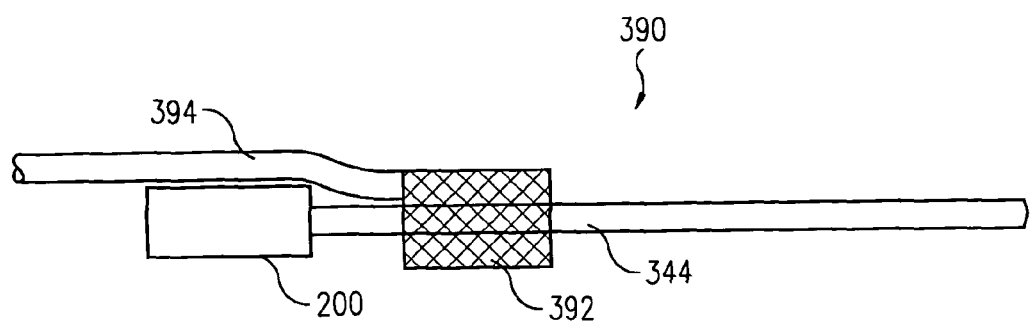

In yet another embodiment, as shown in FIGS. 29A-29B, a stiffening component 390 replaces the outer sheath 384. The stiffening component 390 includes a stiffening sheath 392 and a push shaft 394. The push shaft 394 can be made out of a wire that can be attached to the stiffening sheath 392 and can moveably slide the stiffening sheath 392 along the catheter shaft of the catheter assembly 344. The advancement or retraction of the stiffening sheath 392 is controlled by the push shaft 394. The push shaft 394 is placed outside of the handle 200. The configuration shown in FIGS. 29A-29B allows the stiffening sheath 392 to be pulled outside of the vasculature when not used.

FIGS. 30A-30D illustrate another catheter assembly 501 that have variable deflection shapes or curvatures. The catheter assembly 501 is similar to the catheter assembly 100 or 400 previously described. In general, the catheter assembly 501 is similar to the catheter assemblies 100 or 400 in that the catheter assembly 501 includes a catheter distal section 536 that is deflectable beginning at the deflection transition point

538. Similar to the catheter assemblies 100 or 400, the catheter assembly 501 also includes a catheter proximal section 534, which is further coupled to a handle 200 that may include an injection port 510 and a deflection control 506. The internal components (e.g., the tendon assembly and needle assembly) are constructed similarly to that of the catheter assembly 100 or 400. One thing that is provided in the catheter assembly 501 is the variable or adjustable deflection shapes or curvatures.

The catheter assembly 501 includes a dual-tendon system, which includes a first tendon (or lateral tendon) assembly 540 and a second tendon (or fixed tendon) assembly 542 placed in parallel and in close proximity to one another. Each of the tendon assembly 540 and 542 is disposed within a lumen within the catheter shaft 544. The lateral tendon assembly 540 includes a first tendon 546 that includes a tendon hook 548 coupled to the distal section of the first tendon 546. The tendon hook 548 extends outside of the lumen that the lateral tendon assembly 540 resides in. The fixed tendon assembly 542 includes a second tendon 550 having a plurality of tendon anchors 552 placed along a section of the second tendon 550. The plurality of tendon anchors 552 extends outside of the lumen that the fixed tendon assembly 542 resides in.

The fixed tendon assembly 542 is disposed within a lumen of the catheter shaft 544. In the catheter proximal section 534, the lumen that houses the fixed tendon assembly 542 is located off-center of the catheter shaft 544 throughout the entire length of the catheter shaft 544. The second tendon 550 is fixed at the distal end to the distal tip of the catheter assembly 501.

The lateral tendon assembly 540 is disposed within another lumen of the catheter shaft 544 and runs parallel to the fixed tendon assembly 542. The lumen that houses the lateral tendon assembly 540 is located in the or approximately in the center of the catheter shaft 544 along the catheter proximal section 534. The lumen that houses the lateral tendon assembly 540 is located off-center in the catheter shaft 544 along the catheter distal section 536. The lateral tendon assembly 540 is moveable or slideable along the fixed tendon assembly 542.

Figure 30A:
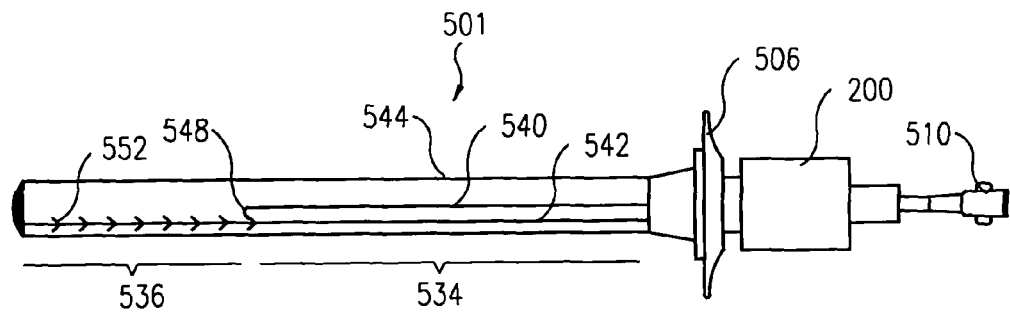
FIGS. 30A-30D illustrates a multi-tendon system that can be incorporated into a catheter assembly to provide multiple deflection ending points to the catheter distal section.
Figure 30B:
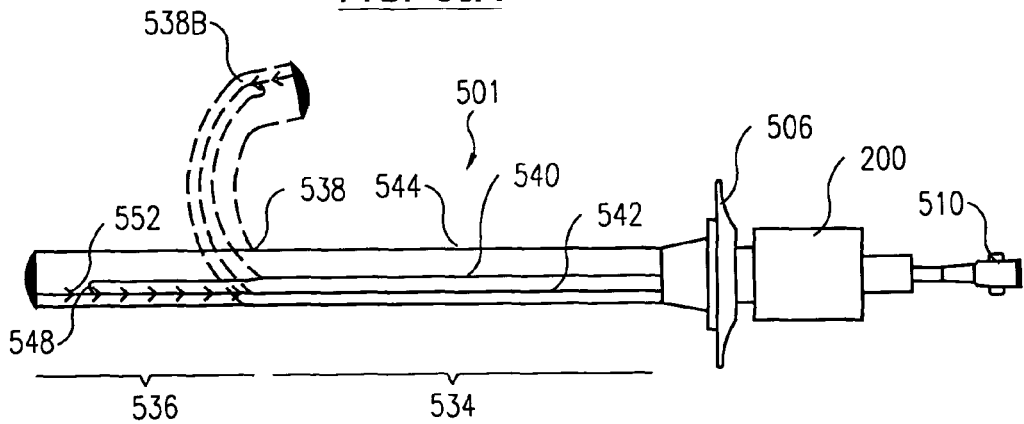
Figure 30C:
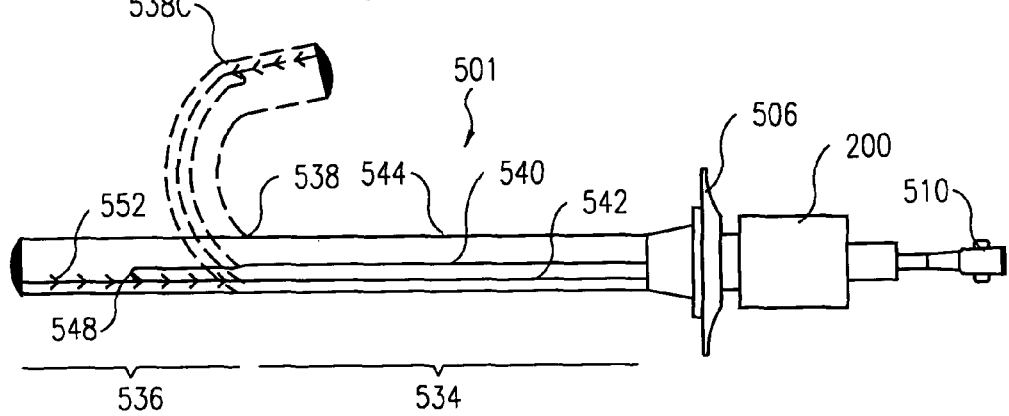
Figure 30D:
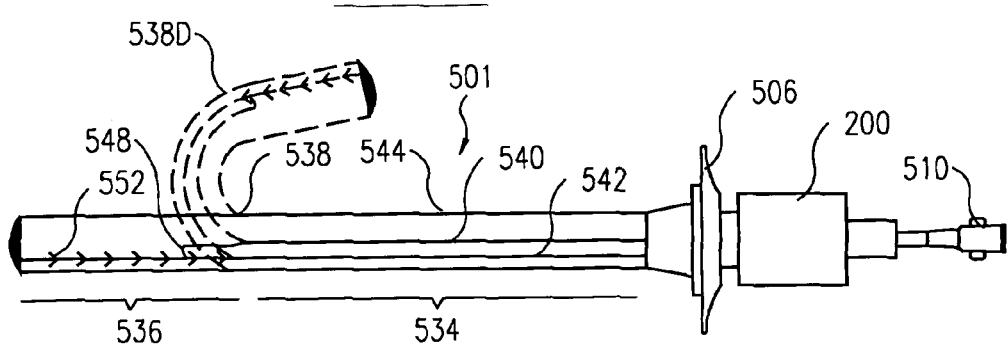

The deflection point 538 of the catheter shaft 544 is the transition point between the catheter proximal section 534 and the catheter distal section 536. The end of the deflection is the point where the lateral tendon assembly 540 ends. When the operator pulls on the lateral tendon assembly 540, the catheter distal section 536 begins to deflect at the deflection point 538 for example, as shown in FIG. 38B. In addition, moving the lateral tendon assembly 540 positions the tendon hook 548 over one of the anchors 552. The hook 548 on the first tendon 546 engages one of the anchors 552 located on the second tendon 550. At the point where the engagement occurs, the lateral tendon assembly 540 ends and the deflection section ends. For instance, as shown in FIG. 30B, when the tendon hook 548 engages the second anchor 552 (from the distal end), the deflection of the catheter distal section 536 begins at the deflection point 538 but ends at the point 538B. The section distal to the point 538B remains straight and undeflected since the lateral tendon assembly 540 is not pulling on this section. In another example, as shown in FIG. 30C, when the tendon hook 548 engages the fourth anchor 552 (from the distal end), the deflection of the catheter distal section 536 begins at the deflection point 538 but ends at the point 538C. The section distal to the point 538C remains straight and undeflected since the lateral tendon assembly 540 is not pulling on this section. In yet another example, as shown in FIG. 30D, when the tendon hook 548 engages the fifth anchor 552 (from the distal end), the deflection of the catheter distal section 536 begins at the deflection point 538 but ends at the point 538D. The section distal to the point 538D remains straight and undeflected since the lateral tendon assembly 540 is not pulling on this section. As can be seen, the various engagement points between the tendon hook 548 and the plurality of the anchors 552 allow one to vary the shapes and curvatures of the deflection of the catheter shaft.

Thus, the catheter shaft 544 will still have a flexible distal section and a stiff proximal section 534. The transition point between the distal and the proximal section defines the beginning of the deflection curve. The deflection curve ends at the point where the tendon hook 548 engages the anchors 552. The catheter shaft section distal to this engagement point will remain straight, extending out tangent to the end of the deflection curve.

In alternative embodiments, the lateral tendon assembly 540 may wrap around the fixed tendon assembly 542 to balance the compression load it generates. In addition, the fixed tendon assembly 542, being the one component taking up the compression force, should be made stiff to resist compression, doing the job of an axial spine as previously described in another embodiment.

In an alternative embodiment, additional lumens are included in the catheter shaft 544 to balance the catheter shaft. At least two additional lumens (not shown) may be included and one of which can be dedicated for a therapeutic tool (e.g., a needle) to be disposed therethrough. The remaining lumen(s) may be filled with lumen filler material that will help in balancing the catheter shaft 544.

In one embodiment, the catheter distal section 536 is not entirely fused to allow enough clearance for the hook 548 to slid along the tendon 550 and engage one of the anchors 552 to provide variable deflection shapes and/or curvatures. In one embodiment, as illustrated in FIGS. 30A-30D, the anchors 552 are low-lying spikes that would serve to anchor the hook 548 when it is pulled back to allow deflection of the catheter assembly 501. The low-lying spike feature of the anchors 552 allow the hook 548 to easily slide over the anchors 552 to move distally along the tendon 550. Once the hook 548 has been moved to the desired anchor 552, pulling on the lateral tendon 540 would cause the hook 548 to engage the anchor 552. At this point, pulling on the lateral tendon 540 will also cause the deflection of the catheter distal section 536 ending at the point where the anchor 552 engages the hook 548. The hook 548 is released from the anchor 552 by manipulation to the lateral tendon assembly 540 proximally (e.g., through the proximal handle 200). The hook 548 is released from the anchor 552 so that the deflection ending point of the catheter distal section 536 can be varied. The hook 548 may be a "C-shape" ring that has a section cut out to create a C-like member. Rotating the lateral tendon 540 allows for the rotating of the opening section of the C-shape ring to be in alignment with the anchor 552 thus facilitating the retraction of the hook 548 off the anchor 552.

FIGS. 31-34, 35A-35H, 36A-36B, and 37A-37B illustrate exemplary embodiments of electrode systems that can be incorporated into a catheter assembly such as the catheter assembly 100, 400, 344, or 501 previously described or herein described. In these figures, an electrode system is incorporated into a catheter assembly 500 which can be any of the catheter assembly described in the disclosure. The catheter assembly 500 is similar to the catheter assemblies 100, 344, 400, or 501 previously described. In general, the catheter assembly 500 is similar to the catheter assemblies 100, 344, 400, or 501 in that the catheter assembly 500 includes a catheter distal section 554 that is deflectable beginning at the deflection transition point 558. Similar to the catheter assemblies 100, 344, 400, or 501, the catheter assembly 500 also includes a catheter proximal section 556, which is further coupled to a handle 200 that may include an injection port 510 and a deflection control 506. The internal components (e.g., the tendon assembly and needle assembly) are constructed similarly to those of the catheter assemblies previously described, e.g., the catheter assemblies 100 or 400. The catheter assembly 500 includes a bipolar electrode system, which includes a tip electrode 504 and at least one additional electrode band 505.

The electrode system can be used to search and acquire desired local cardiac signals, such as the signal of the His bundle or the AV node, in the chambers of the heart and to aid the catheter assembly 500 in delivering therapeutic biologics to the corresponding locations. An example of a therapeutic application for the catheter assembly 500 is to deliver a biologic agent (gene, protein, etc) to a defective cardiac node or bundle to develop a bio-pacer. Another example is to use the electrode system to locate an infarct zone in the myocardium of the left ventricle and deliver a therapeutic agent to the same location.

The catheter system is designed to deliver the therapy precisely to the location at which a target cardiac signal is detected. In general, these signals have low amplitudes. Therefore, it is necessary to reduce the noise to signal ratio and be able to sense the signal locally versus globally. This catheter system uses bipolar electrodes for mapping out the desired cardiac signals. The bipolar electrodes are constructed by having two metallic electrodes mounting closely to each other on the catheter. Signal sensed from one electrode is used as a ground reference for the other. However, keep in mind that the bipolar design can be easily converted to unipolar design, if far field signals are needed. The bipolar electrodes may be used as two unipolar electrodes by the way in which they are connected to the recording machine.

Figure 31:
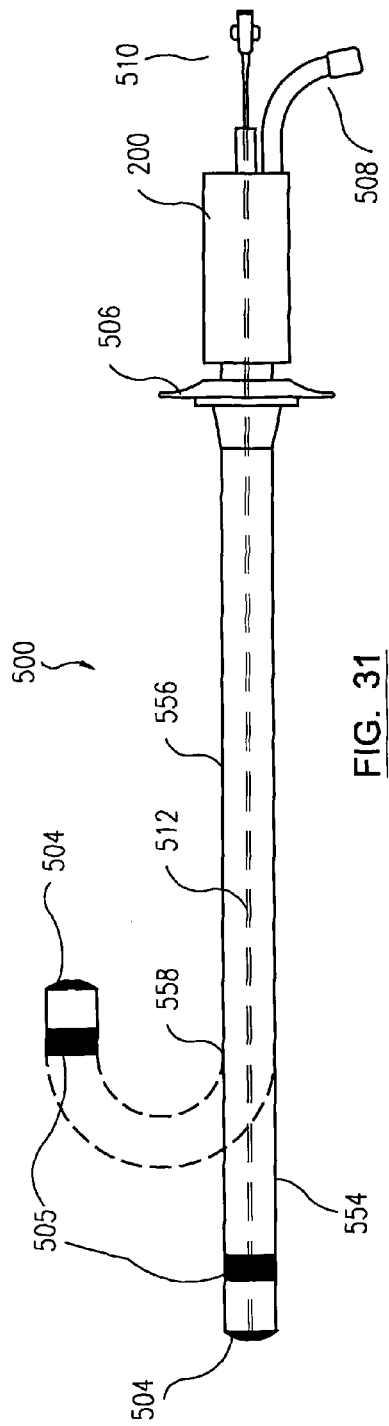
FIG. 31 illustrates a catheter assembly having an electrode system incorporated therein.

In one embodiment, the tip electrode 504 and the band electrode 505 can be spaced out 2 cm apart (in another embodiment, within 0.5 cm to 2 cm) from each other and one of them is located at the tip of the catheter assembly 500 as illustrated in FIG. 31. The electrodes are connected independently to a conductive and insulated wire 514 (FIGS. 32-33) and 524 (FIG. 35A-35H). Each of the electrode wires 514 and 524 runs within the wall of the catheter to the proximal end, from which it is attached to an electrical cable connector 508 that is plugged into a cardiac recording machine (not shown).

Figures 32, 33:
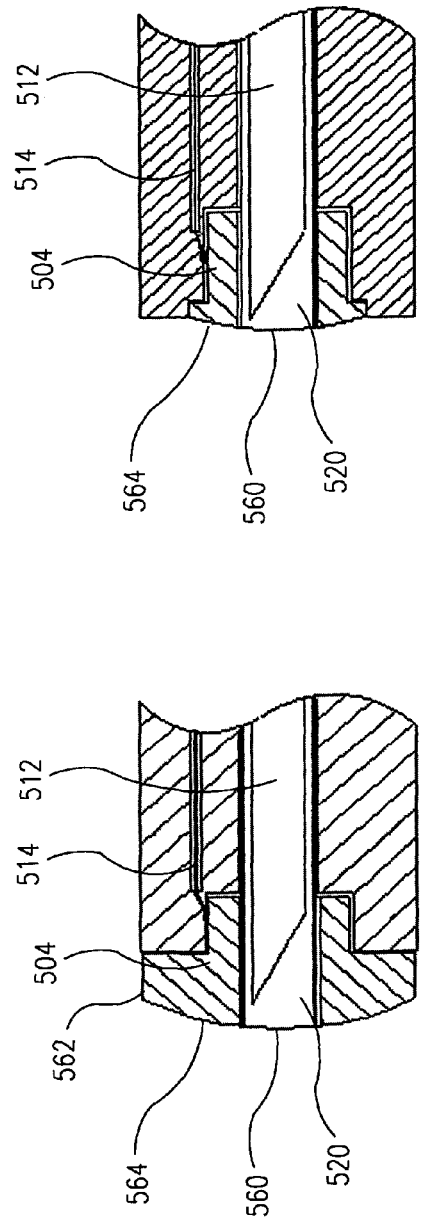

FIGS. 32-34 show different embodiments for the electrode system design. In all designs, the tip electrode 504 may be glued or heat fused into the inner lumen of the catheter shaft. This attachment may be strengthened by designing in roughened surface texture, such as a sea-saw or barbed surface feature, on the stem of the electrode 504. The roughened texture will increase the adhesion or bond between the electrode 504 and the catheter shaft. The electrode may be made of any biocompatible and conductive metallic alloy such as platinum or gold. It may also be made with material with a non-ferromagnetic composition so that the catheter can be used inside of a MRI scanner.

In FIG. 32, the tip electrode 504 is positioned around a center needle lumen 520. The electrode 504 can be in any of the following physical shape: round or non-round, curved or flat tip surface, or a thin ring design. The tip electrode 504 includes an opening 560, which is located over the center needle lumen 520. A needle 512 exits from the opening 560. This tip electrode 504 may contact the heart wall on both the side 562 and the tip 564 of the electrode 504 with similar signal amplitude measured. The embodiment shown in FIG. 32 may be the easiest to use in terms of cardiac mapping. In one embodiment, the orientation of the catheter assembly 500 may be visualized using fluoroscope technology and thus allows for accurate determination of catheter orientation that may be necessary for needle 512 injection into the target site.

In some applications, detecting the target signal does not give any indication of catheter orientation. In some incidences the catheter may be laying parallel to the heart wall when the signal is detected so that the extending needle 512 will not engage the heart wall. FIG. 33 shows another tip electrode 504 configured to address the orientation detection issue. The tip electrode 504 is only exposed at the tip surface 564 as shown in FIG. 33. When the exposed tip 564 touches the target zone, the signal amplitude will be the greatest. The catheter assembly 500 is oriented almost perpendicular to the wall. Therefore, the embodiment of the tip electrode 504 shown in FIG. 33 allows for better identification of catheter tip orientation. Once the desired signal is detected, the catheter tip is likely oriented in a way that facilitates needle 512 engagement to the heart wall.

In some other applications, target locations are within a tight spacing such that there is not enough room for the catheter to stand perpendicular to the wall. One example is the septal wall behind the right ventricle valve leaflet. The spacing is so tight that the catheter has to lay side ways. Extending the needle 512 from the tip of the catheter assembly 500 will not get to the target, which is the Septal wall. In FIG. 34, the needle 512 exits the tip electrode 504 on the side of the catheter shaft of the catheter assembly 500. In this embodiment, the tip electrode 504 is only exposed on the side 566, which is the side that the needle 512 exits the catheter assembly 500.

In one embodiment, to prevent the needle 512 from penetrating through the catheter wall when the needle 512 moves through the curve 568, a deflector ribbon 502 is mounted on the outer diameter of the lumen that houses the needle 512 especially along the curve 568.

The deflector ribbon 502 can be made of metallic material such as stainless steel, Nitinol, or other metallic alloy. The ribbon 502 is placed on the inner surface of the needle lumen 520 over the length covering the length of the bend curve. The proximal end of the ribbon 502 is fixed and can be embedded within the polymer of the lumen 520. The needle 512 is most likely placed in such a way that its tip is always located distal to the proximal end of the ribbon 502. Therefore, advancing the needle 512 will not catch the proximal end of the ribbon 502. The distal end of the ribbon 502 can be fixed to the lumen 520 for example, by using glue. Over the length of the ribbon 502 where the needle tip may travel through, the ribbon is exposed over the luminal surface. The ribbon 502 is also made slightly wider than the outer diameter of the needle 512 such that the needle 512 tip is always riding on the ribbon 502 surface. As the needle tip is advanced distally through the bend region, the sharp beveled tip has the tendency to slide on the luminal wall in a direction tangent to the curvature of the bend region. Without the ribbon 502, the needle 512 will most likely puncture into the polymer constructing the needle lumen wall. With the ribbon 502, the needle tip is prevented from puncturing into the curved wall but, rather, follow the curved wall to exit the catheter on the side of the tip. In one embodiment, the side 566 where the needle 512 exits the catheter assembly 500 is the side of the catheter shaft that contacts the wall or the target site. Exposing the tip electrode 504 only at this side allows for enhanced sensitivity and accurate determination the orientation of the catheter assembly 500 and that will facilitate the needle 512 in penetrating the target site. Additionally, the embodiment shown in FIG. 34 also allows the catheter assembly 500 to stably lean against a moving heart wall during injection.

In one embodiment, as illustrated in FIGS. 35A-35B, the band electrode 505 is located proximate to the tip electrode 504, for example, within 2 cm (or within 0.5-2 cm) proximal to the tip electrode 504. Signals sensed in the band electrode 505 are used as a reference for the tip electrode 504 signals. Dependent on the amplitude of the target signal source and the noise signals around the target source, the distance between the two electrodes may vary for optimal performance. The lower the source signal amplitude and the higher the signal to noise ratio needed, the shorter the required distance between the two electrodes.

The band electrode 505 can be constructed in several ways. It can be a metal band connected to a conductive wire 524 running within the wall of the catheter shaft. The band electrode 505 is either glued or heat fused on the inner wall of catheter shaft of the catheter assembly 500. For this to be conductive, at least part of the band electrode 505 has to be exposed to the blood pool. The band electrode 505 may be placed or adhered to the outer wall of the catheter shaft (FIG. 35A). Alternatively, the band electrode 505 may be incorporated into the catheter shaft (FIG. 35B). Therefore, if the polymer material on the catheter shaft covers the band electrode 505 from the fusing process, an opening 522 (FIG. 35B) is made through the covering layer to expose the band electrode 505. Alternatively, a conductive coil or wrapping of the conductive wire may be used to form the band electrode 505. The coil or the wrapped wire will be more flexible than a metallic band.

In an alternative embodiment, the electrode system is incorporated into the tip anchor (e.g., the tip anchor 140 of the catheter assembly 100 or the tip anchor 444 of the catheter assembly 400). FIGS. 35C-35F illustrate such an exemplary embodiment.

FIG. 35C shows attachments of a tendon 526, a conductive wire 513 and a needle 512 to a tip anchor-electrode member 580. The tip anchor-electrode member 580 is referred as such because it functions both as a place for the tendon and needle assemblies of a catheter shaft to anchor to as well as an electrode system for the catheter shaft. The tip anchor-electrode member 580 has a groove 581 and a groove 582. The conductive wire 513 is soldered into the groove 581 and the tendon 526 is soldered into the groove 582. The grooves 581 and 582 need not be 180-degrees apart, although it is shown this way in FIG. 35C. A needle sheath 583 is glued to the central lumen 584 of the tip anchor-electrode member 580. The needle sheath 583 electrically insulates the needle 512 from the tip anchor-electrode member 580.

In one embodiment, in order to increase bond strength of the solder joints for the tendon 526 and the conductive wire 513 to the tip anchor-electrode member 580, a mechanical locking structure is implemented in the groove 581 or 582. In one embodiment, the distal section of the groove 582 is wider than the proximal section of the groove 582. For the tendon 526 attachment, the tendon 526 tip is flattened to produce a wider section 526-W that fits in the wider groove section and the non-flattened, narrower, section 526-N of the tendon 526 fits into the narrower section of the groove 582. Solder is melted to fill the gaps of the groove 582 to secure the tendon 526 in the groove 582. This is illustrated in FIG. 35D. For the conductive wire 513, insulation 513-I is stripped from the distal end of the conductive wire 513. The tip section 513-T of the conductive wire 513 is curled up within the wide section of the groove 581. Solder is melted to fill the gap within the groove 581 holding the conductive wire 513 inside of the groove. This is illustrated in FIG. 35E.

Figure 35F:
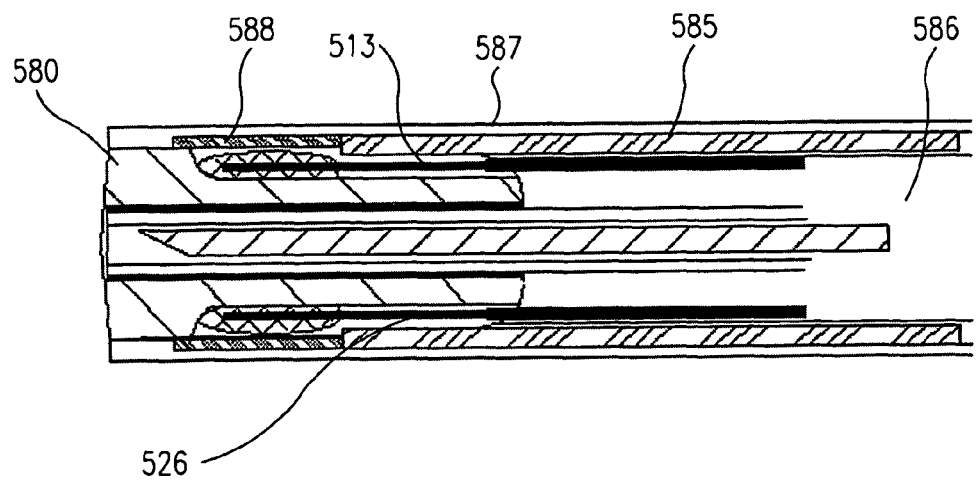

FIG. 35F shows assembly details of the tip anchor-electrode member 580 in a catheter assembly such as the catheter assembly 100, 400, or 500. The tip anchor-electrode member 580 rests on the distal end of a compression cage 585 and is positioned distal to, but not necessary in physical contact for more freedom for deflection, with a filler material 586 of the distal catheter shaft. The stem, which is the smaller diameter section, of the tip anchor-electrode member 580 is coupled to the compression cage 585 by using techniques such as gluing or soldering. The distal jacket 587 and the tendon 526 will help holding the tip anchor-electrode member 580 within the catheter. A capture band 588, made of metallic material such as stainless steel or platinum alloy, is soldered or glued over the tip anchor-electrode member 580 covering the soldered tendon 526 and conductive wire 513. The polymer distal outer jacket 587 is fused over the section overlapping with the tip anchor-electrode member 580 and the distal end of the compression cage 585.

Figure 35G:
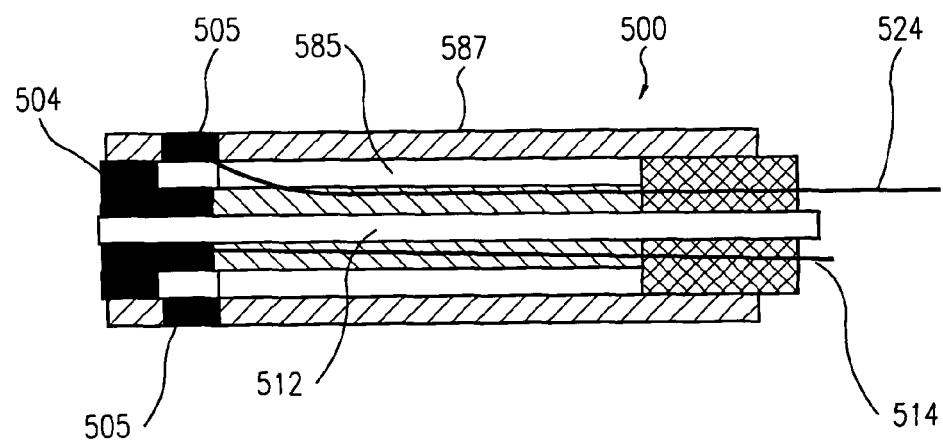
Figure 35H:
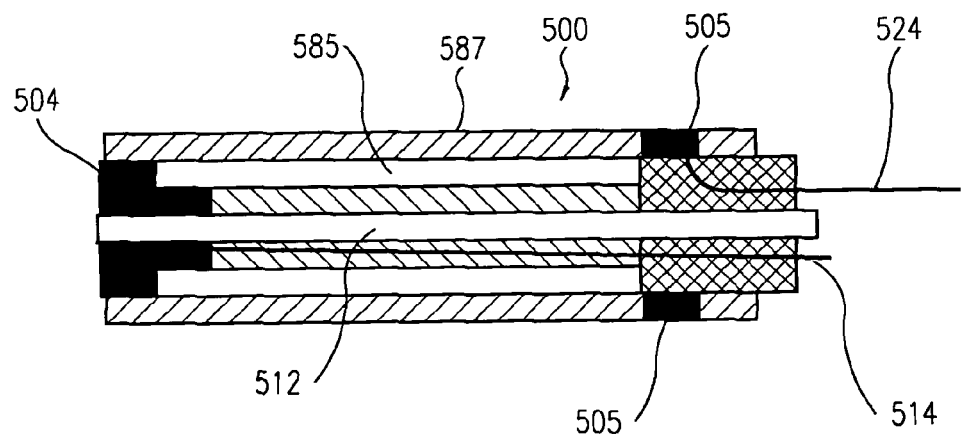

In some embodiments, the catheter assembly 500 includes a compression cage 585 as previously described. In such embodiments, it may be convenient to place the band electrode 505 distal (or immediately distal) to the compression cage 585 as shown in FIG. 35G or alternatively proximal (or immediately proximal) to the compression cage 585 as shown in FIG. 35H. This makes it easier to assemble the band electrode 505 and the associated conductive wire 524 into the catheter assembly 500.

Figure 36A:
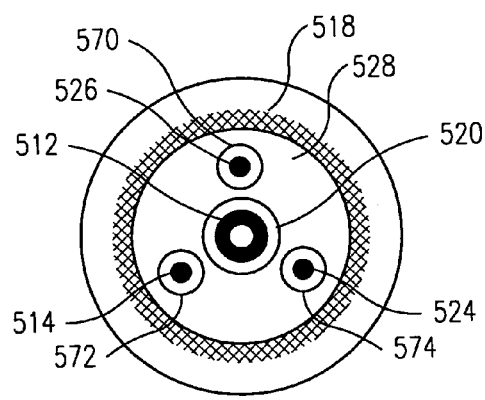

FIGS. 36A-36B and 37A-37B illustrate exemplary embodiments of the location of the conductive wires 514 and 524 relative to the tendon assembly and the needle assembly of the catheter assembly 500. In FIG. 36A, the needle 512 is located in the central lumen 520, a tendon 526 is located in an off-central lumen 570, the conductive wire 514 is located in an off-central lumen 572, and the conductive wire 524 is located in another off-central lumen 574. The empty space within the catheter shaft of the catheter assembly 500 may be filled with a polymer filler 528 and supported with a braider layer 518 similar to the catheter assemblies previously described, e.g., catheter assemblies 100 or 400.

Figure 36B:
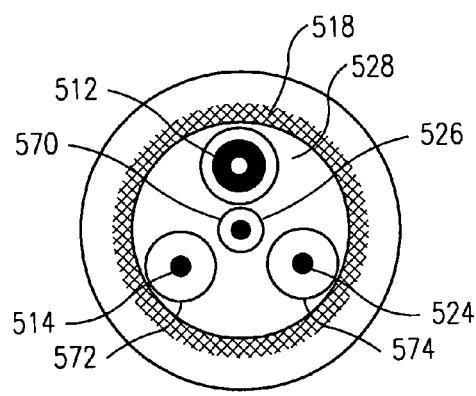

In FIG. 36B, the needle 512 is located in an off-central lumen 520. The needle 512 may be located off-center in the catheter proximal section 556 where the tendon 526 is located in the center similar to previously described, e.g., catheter assemblies 100 or 400.

Figure 37A:
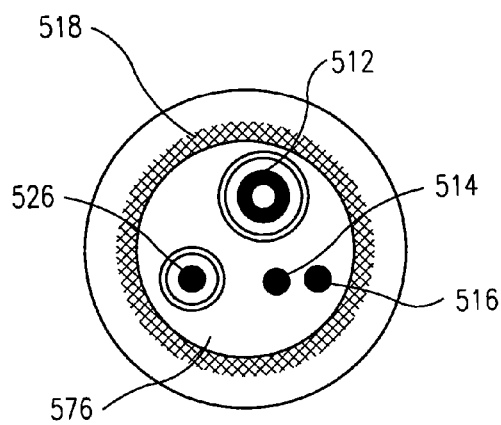
Figure 37B:
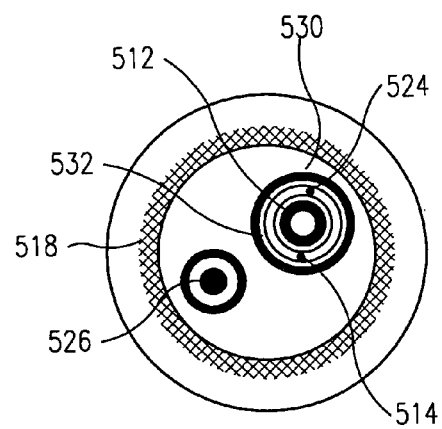

In FIG. 37A, the catheter shaft includes a hollow lumen 576. All of the internal components of the catheter assembly 500, e.g., the needle assembly, the tendon assembly, and the conductive wires are all "floating" inside the hollow lumen 576. The term floating means that the internal components are not embedded in any polymer. Since the tendon assembly and the needle assembly have the freedom to float within the hollow lumen 576, the stiffness from each internal component on the catheter assembly 500 would shift as the catheter assembly 500 is rotated. Therefore, the catheter assembly 500 will not have a preferred orientation and will respond well to rotation. The hollow lumen 576 will be in the proximal section of the catheter, similar to catheter assembly 400. The internal components "float" within this hollow lumen 576 in the proximal section of the catheter shaft but fixed in radial (shaft cross-sectional) position on both ends of the catheter proximal shaft within the anchoring members such as the anchoring members 428 and 430 of the catheter 400. Their locations are fixed over the cross-section of the catheter shaft within the anchoring members in such a way that the stiffness is balanced at the center of the catheter shaft. In this case, the catheter's preferred orientation is minimized and the rotation response can be smooth, especially when the stiffness for all the internal components is not too different from each other.

However, wrapping the internal components, as described for catheter 400, ensures a complete balance of the stiffness from all the internal components.

For any of the embodiments described above, the movements of the tendon and the needle(s) are controlled by a catheter handle 200 (see below) attached to the proximal end of the catheter assembly. The tendon is coupled to a pull-mechanism, which has a limited travel distance. When the tendon is pulled, the catheter distal section deflects. The travel distance of the pull-mechanism can be locked at any location and will only move under a manual force.

The catheter handle 200 comprises a first control mechanism that controls the tendon portion of the catheter assembly and a second control mechanism that controls the needle portion of the catheter assembly. The first control mechanism thus controls the deflection of the catheter assembly and the second control mechanism controls the needle extension control.

Figure 38A:
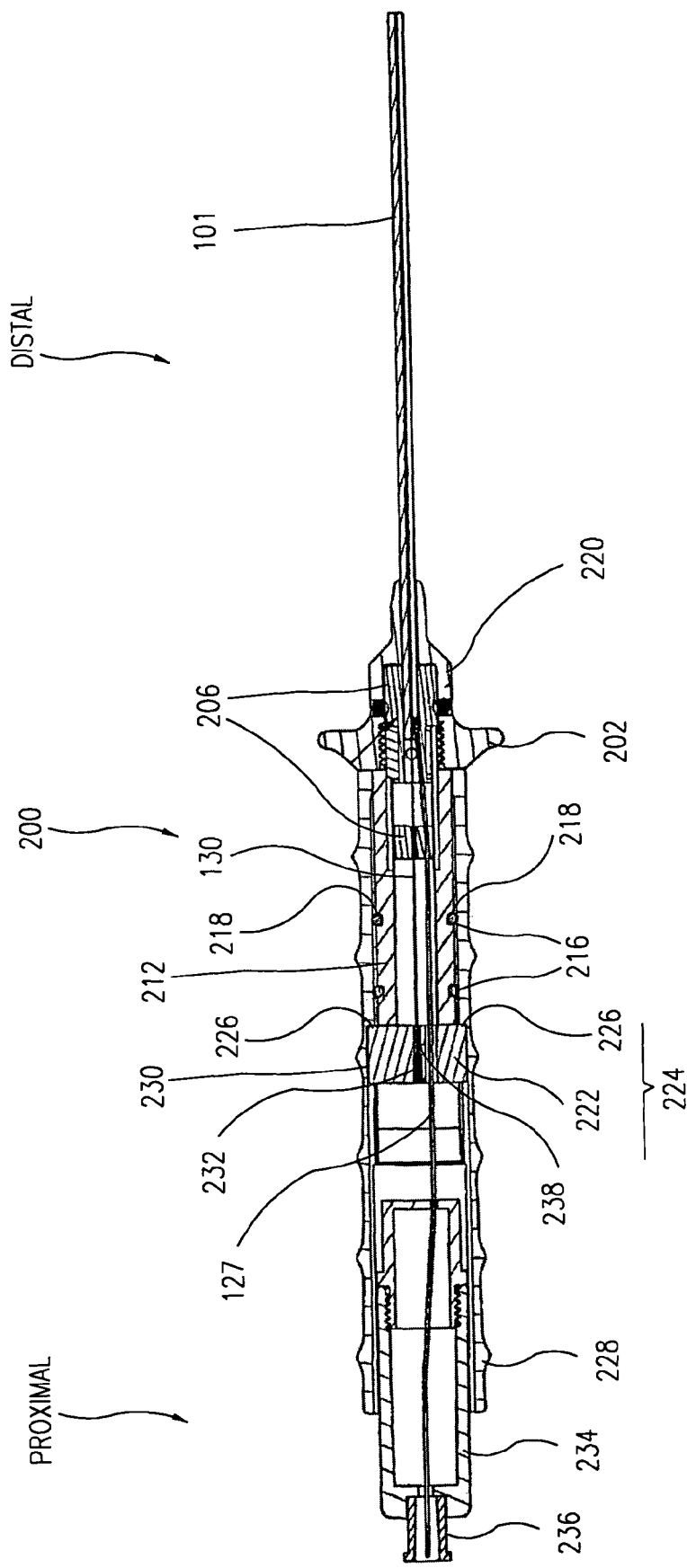
FIG. 38A illustrates a side-view of a catheter handle that can be incorporated to a catheter assembly.
Figure 38B:
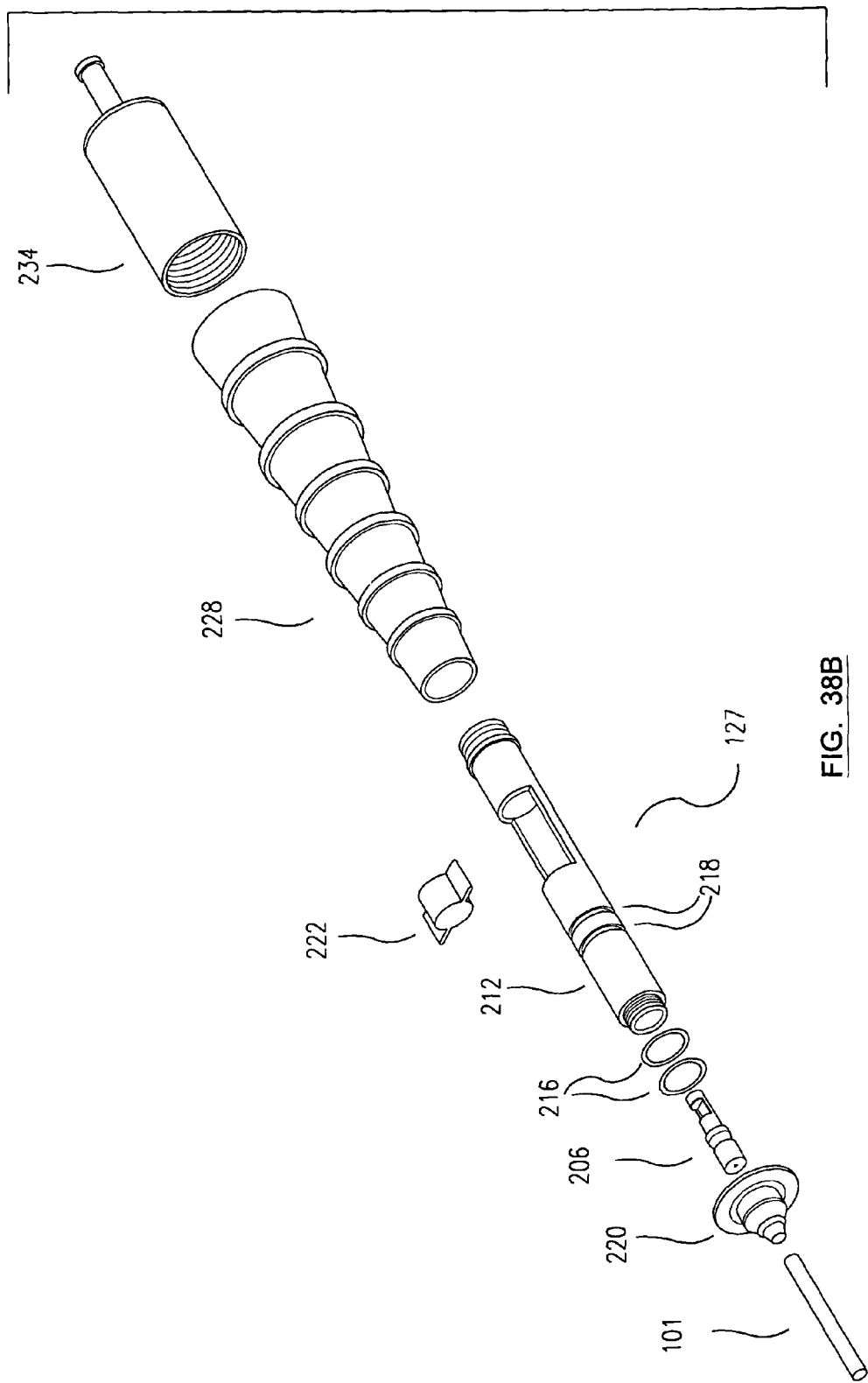
FIG. 38B illustrates an exploded view of a catheter handle.

FIGS. 38A-38B illustrate a detailed drawing for the first control mechanism of the catheter handle 200. FIG. 38A illustrates the cross-sectional side view of the handle 200 while FIG. 38B illustrates an exploded three-dimensional view of the handle 200. The first control mechanism comprises a catheter holder 206, an inner housing 212, a distal adapter 220, a deflection control 202, a tendon holder 222, a proximal adapter 234, and an outer housing 228. The catheter holder 206 couples a catheter shaft, such as the catheter shaft 101 of the catheter assembly 100, to the catheter handle 200. It is to be appreciated that the catheter shaft 101 is only an example of a catheter shaft of a catheter assembly (e.g., the catheter assembly 100, 400, 500, and 344) that can use the catheter handle 200 to controls the deflection of the catheter assembly and the movement of the needle assembly. Any suitable catheter shaft can replace the catheter shaft 101. The catheter shaft 101 and the catheter holder 206 are bonded together and thus the catheter shaft 101 is fixed to the distal end of the catheter handle 200.

The catheter holder 206 sits coaxially inside and on the distal end of the inner housing 212. The catheter holder 206 also includes a rotation lock mechanism (not shown) on the outside of the catheter holder 206 that is capable of locking the catheter holder 206 to the inner housing 212. The catheter holder 206 nests inside of the inner housing 212. The rotation lock mechanism enables the catheter holder 206 to be locked without freedom to rotate within the distal end of the inner housing 212.

The inner housing 212 is moveably mounted within the outer housing 228. The inner housing 212 includes at least 1 or, more ideally, 2 elastomer o-rings 216 that are mounted on the grooves 218 located on the outer surface of the inner housing 212. The o-rings can be pure elastomer o-ring or a ball seal in which a spring is captured in an elastomer o-ring housing. The elastomer o-rings 216 create friction between the inner housing 212 and the outer housing 228 to facilitate the control of the inner housing 212 as it moves relative to the outer housing 228. With the friction present, the inner housing 212 can be moved in a controlled manner relative to the outer housing 228 without uncontrollably sliding backward.

The catheter holder 206 is also partially disposed into the distal adapter 220. The distal adapter 220 does two things: 1) couples to the inner housing 212 trapping the catheter holder 206 together as one integral body, and 2) acting as a thumb rest for deflection manipulation. A feature such as the deflection control 202 is incorporated into the distal adapter 220 to allow the inner housing 212 to be moved proximally or distally relative to the outer housing 228 to control the deflection of the catheter assembly.

The tendon holder 222 rests on a half-circle section 224 of the inner housing 212. The tendon holder 222 has side wings 226 that nest within the matching grooves 230 created on the inner wall of the outer housing 228. The grooves 230 and the side wings 226 define the maximum travel distance for the tendon holder 222. Additionally, the grooves 230 and the side wings 226 allow the tendon holder 222 to be moveably captured within the inner housing 212 and the outer housing 228. A tendon such as the tendon 130 from the catheter assembly 100 is soldered under tension to a small tube 232 that sits against the proximal side of the tendon holder 222. The tendon holder 222 includes a central lumen 238 through which the tendon 130 is inserted therethrough.

Figure 43:
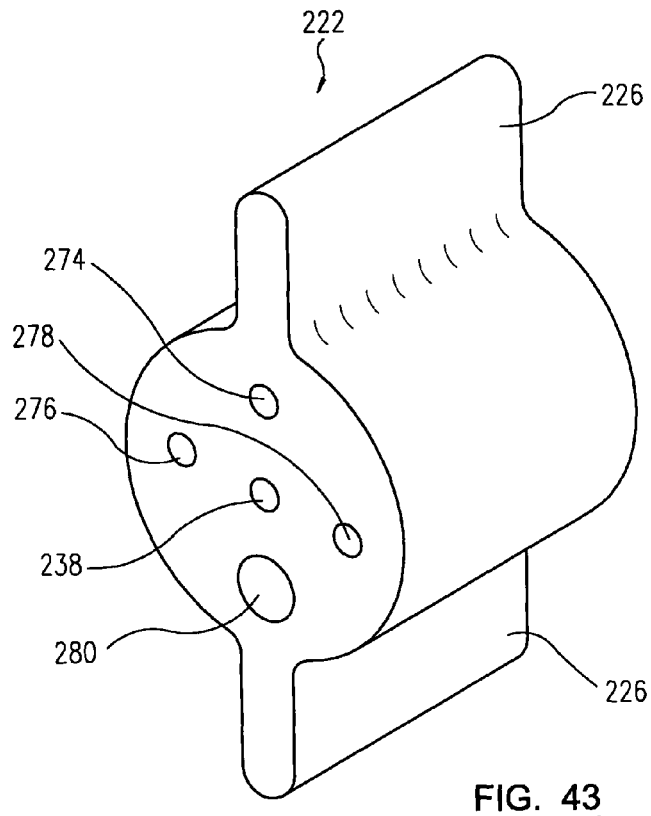
FIGS. 43-44 illustrate a tendon control mechanism of a catheter handle.

FIG. 43 illustrates a three dimensional view of the tendon holder 222. The tendon holder 222 includes a central lumen 238 located in the middle of the tendon holder 222. The tendon holder 222 also includes at least one off-central lumen, e.g., off-central lumen 274, 276, 278, and 280. Each off-central lumen can accommodate at least one needle assembly. Alternatively, only one off-central lumen, which may be larger than the central lumen 238, may be included that can accommodate all components that need to go into the catheter shaft of the catheter assembly.

Figure 44:
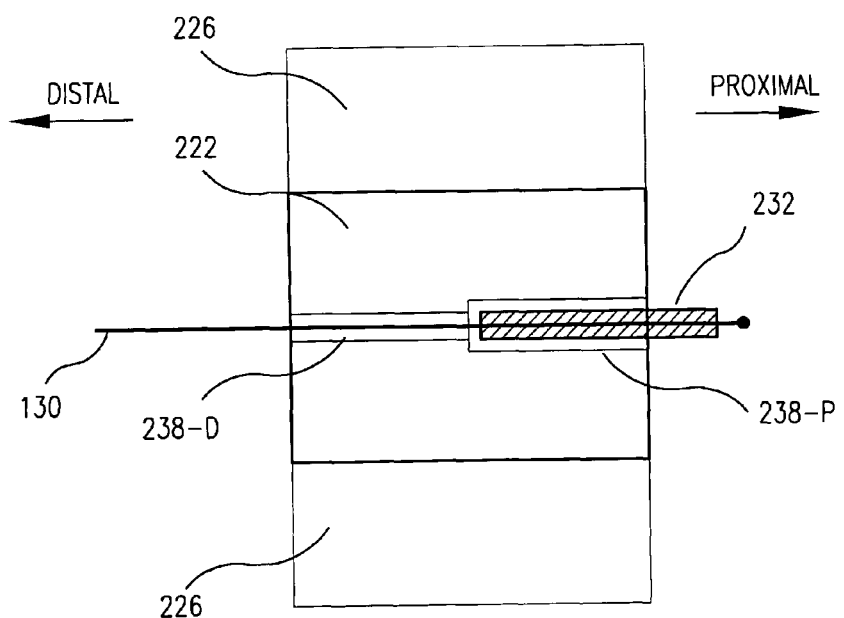

FIG. 44 illustrates how the tendon 130 is coupled to the tendon holder 222. The central lumen 238 is divided into two sections, a proximal central lumen 238-P and a distal central lumen 238-D. The tendon 130 is first disposed within a small tube 232, which is then disposed within the proximal central lumen 238-P. The tendon 130 and the small tube 232 are prevented from moving into the distal central lumen 238-D since the distal central lumen 238-D is smaller than the proximal central lumen 238-P and/or smaller than the tube 232. In one embodiment, the small tube 232 is tightly fitted or glued into the lumen 238P. The tendon 130 is soldered to the tube 232. Therefore, the tendon 130 is fixed longitudinally on the tendon holder 222. The tendon 130 is coupled to the tendon holder 222 such that the proximal end of the tendon 130 cannot pass distally through the small tube 232. The distal central lumen 238-D allows the tendon 130 to extend therethrough to reach the rest of the catheter assembly with the proximal section of the tendon 130 being captured via the soldering at the proximal central lumen 238-P. When the tendon holder 222 is moved proximally (via the moving of the outer housing 228), the tendon 130 is also pulled proximally to deflect the catheter assembly as previously described.

The proximal adapter 234 screws onto the proximal end of the inner housing 212. The proximal adapter 234 provides connection to the second control mechanism that controls the needle extension and supports the needle sheath(s) of the catheter assembly.

As can be seen, the proximal adapter 234, the inner housing 212, the catheter holder 206, and the distal adapter 220 are coupled together as one integral core body in which the tendon 130, tendon holder 222, and the needles are housed and located.

To actuate catheter deflection, the operator holds onto the outer housing 228 and pushes the outer housing 228 back while pushing on the distal adapter 220 at the deflection control 202. The operator can use the deflection control 202 to move the outer housing 228 relative to the inner housing 212. Moving the outer housing 228 relative to the inner housing 212 causes the tendon holder 222 to pull onto the tendon 130, which results in the deflection of the catheter shaft 101.

Figure 40:
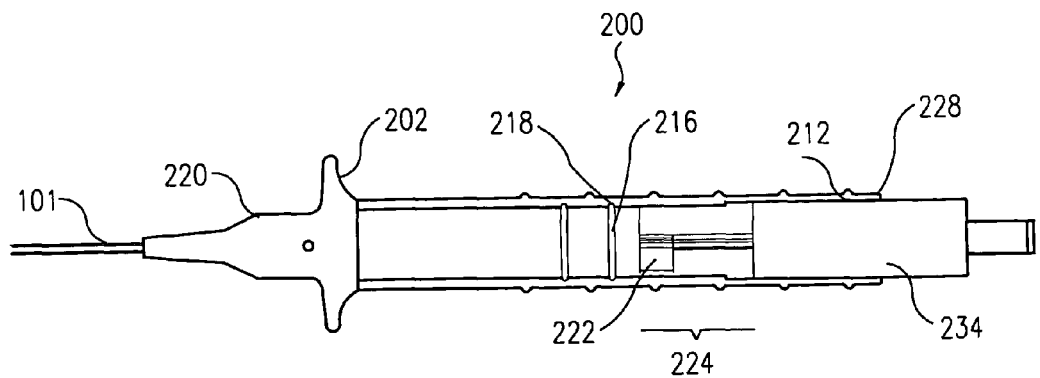
FIG. 40 illustrates another view of the catheter handle illustrated in FIG. 38A.
Figure 41:
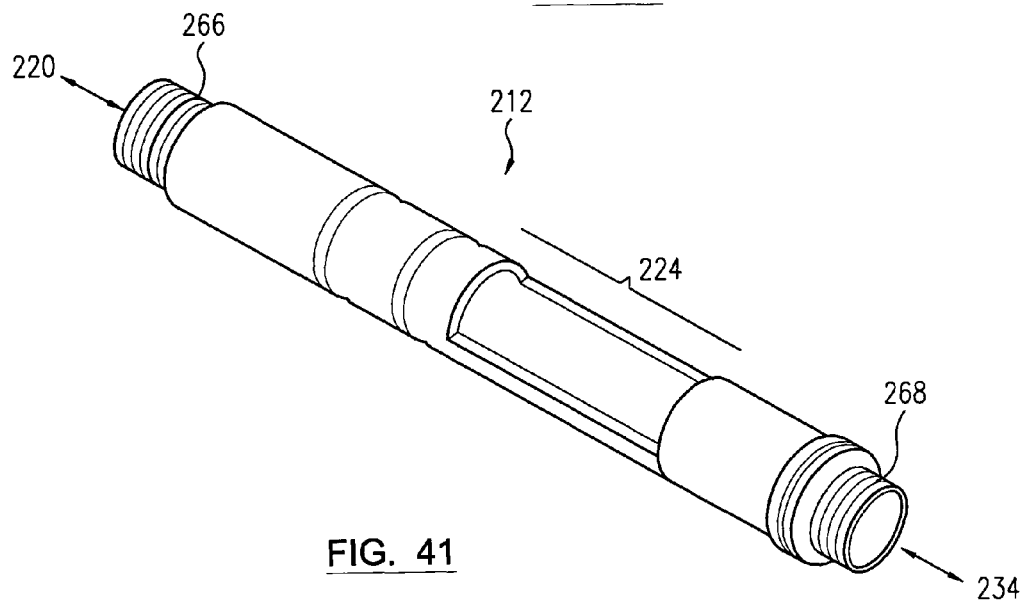
FIG. 41 illustrates a three-dimensional view of an inner housing included in a catheter handle.
Figure 42:
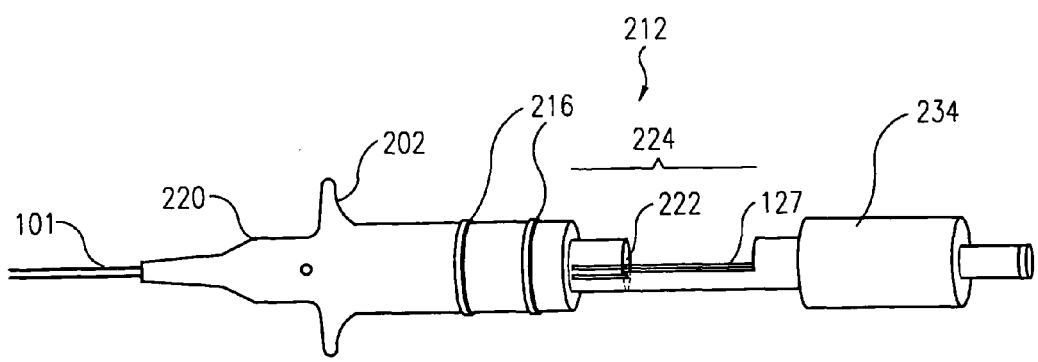
FIG. 42 illustrates a three-dimensional view of an inner housing included in a catheter handle.

FIG. 40 illustrates a cross-sectional view of the catheter handle 200. FIG. 41 illustrates a three-dimensional view of the inner housing 212. The inner housing 212 also includes a proximal section 268 and a distal section 266. The distal section 266 can be a threaded section to allow the distal section 266 to couple the inner housing 212 to the distal adapter 220. With the distal section 266 being a threaded section, the inner housing 212 can be screwed into the distal adapter 220 that has a complimentary threaded section. The proximal section 268 couples the inner housing 212 to the proximal adapter 234. In one embodiment, the proximal section 268 is also a threaded section to allow the proximal section 268 to couple the inner housing 212 to the proximal adapter 234 that has a complimentary threaded section. FIG. 42 illustrates a three-dimensional view of the inner housing 212 coupled to the distal adapter 220 and the proximal adapter 234.

Figure 39A:
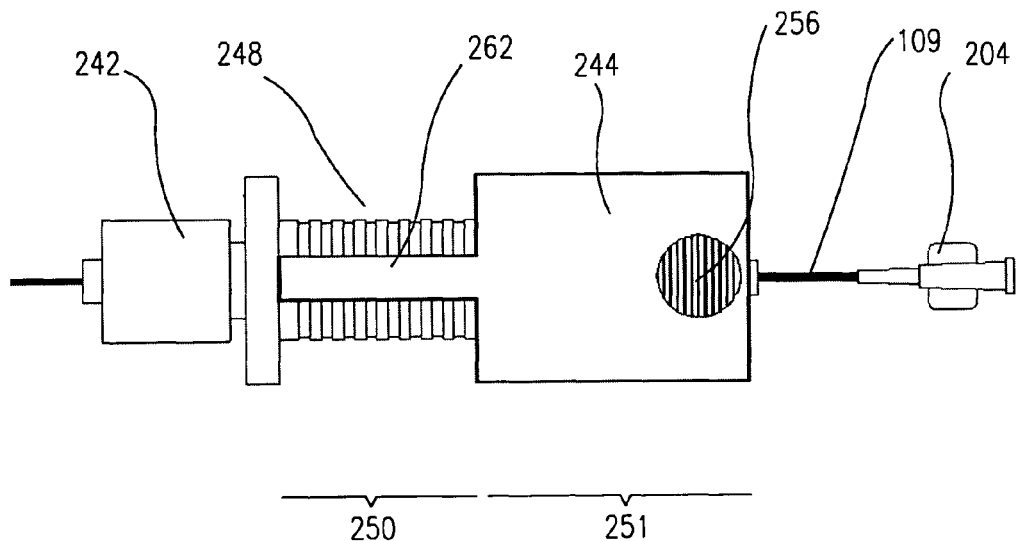
Figure 39B:
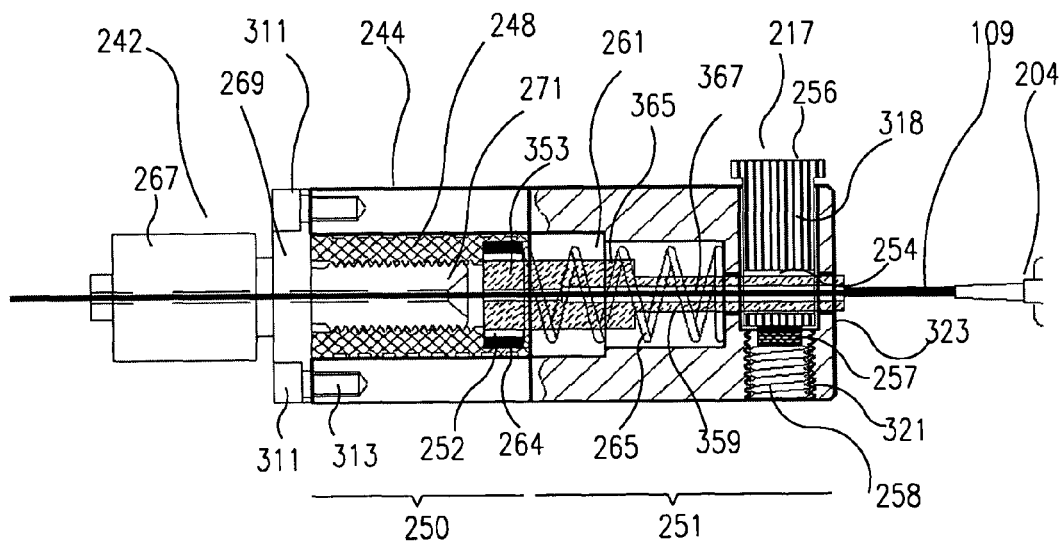

FIGS. 39A-39B show the second control mechanism 240 that controls the needle extension and adjustable extension stop for a needle assembly such as the needle assembly 109 previously described. It is to be appreciated that other needle assembly or other therapeutic tool can replace the needle assembly 109 shown in FIGS. 39A-39B. The second control mechanism 240 is coupled to the proximal adapter 234 of the catheter handle 200. In an alternative embodiment, the second control mechanism 240 is integrated within the proximal adapter of the catheter handle 200. The second control mechanism 240 comprises a distal connector 242, a housing 244, a set of connector couplers 246, a needle stop 248, a back stop 262, an extend stop 264, a needle holder 250, and a needle lock 252 (see also FIG. 39G).

FIG. 39A shows an outside view of the second control mechanism 240 and FIG. 39B shows a side view of FIG. 39A with all the internal components. The second control mechanism 240 comprises a distal connector assembly 242, a housing 244, a needle stop adjustment dial 248, and a needle locking mechanism 217 for the needle assembly 109. The needle assembly 109 runs through a center lumen of the second control mechanism and is attached to an injection port 204 on the proximal end.

As shown in FIG. 39A, the distal connector assembly 242 is coupled to the proximal adapter 234 of handle 200. The housing 244 and the distal connector assembly 242 are coupled together encasing all the internal components (see also FIG. 39C). The housing has a cut away section 250 in the distal end and a circular encasing section 251 in the proximal end. The cut away section 250 of the housing 244 has two poles 262 bridging the distal adapter assembly 242 and the circular encasing section 251 of the housing 244 (see also FIGS. 39C and 39E). The needle stop adjustment dial 248 is therefore exposed between the two poles 262 for finger access (see also FIG. 39D). By turning the needle stop adjustment dial 248, the allowed needle extension length varies. The locking mechanism 217 resides in the housing laterally. This locking mechanism 217 puts a frictional force on the needle assembly 109 such that the needle assembly 109 will not move without actuation by the operator.

FIG. 39B shows some internal components of the second control mechanism 240. The distal adapter assembly 242 consists of three functional parts: a rotational lock 267, a coupling base plate 269, and a threaded stem 271. The rotational lock 267 couples to the proximal adapter 234 of handle 200 for example, via a matching locking mechanism (not shown). The coupling base plate 269 has two fastening holes 311 for securing onto the matching threaded holes 313 on the poles 262 of the housing 244 (FIG. 39A). This coupling can as well be done by other methods such as gluing and plastic welding. The threaded stem 271 is made as part of and sits right in the center of the coupling base plate 269. This threaded stem 271 provides matching threads for the needle stop adjustment dial 248 (FIG. 39A) to travel longitudinally while rotating on the threads.

The needle stop adjustment dial 248 resides in the space between the poles 262 of the housing 244 and the threaded stem 271 of the distal adapter assembly 242. As mentioned previously, by turning the needle stop adjustment dial 248, its position changes along the longitudinal axis of the second mechanism 240. The proximal recessed surface 252 of the needle stop adjustment dial 248 acts as the needle stop. As the needle stop adjustment dial 248 changes its position, the needle stop location also changes.

Several internal components are housed within the space proximal to the needle stop adjustment dial 248 and within the central cavity 261 in the circular encasing section 251 of the housing 244. These internal components are a washer 264, a spring 265, and a needle assembly holder 365 (see also FIG. 39F). The function of the spring 265 is to provide a compression force on the needle stop adjustment dial 248 so that, once the needle stop location is set, the dial does not accidentally turn by itself without the actuation from the operator. The spring 265 is always under compression. The washer 264 is sandwiched between the proximal recessed surface 252 of the needle stop adjustment dial 248 and the spring 265. It acts as a lubricious isolation to allow for easy turning of the needle stop adjustment dial 248 under the compression force from the spring 265. The needle assembly holder 365 is coupled to the needle assembly 109 through its central lumen 367 using adhesive. When the needle is fully extended to its set extension length, the distal surface 353 of the needle assembly holder 365 is in contact with the proximal recessed surface 252 of the needle stop adjustment dial 248.

The needle lock assembly 217 runs through the housing in a lateral direction. The needle lock assembly 217 consists of a lock bushing 318 (see also FIG. 39H) that includes a side hole 254, a lock spring 257, and a lock spring retainer 258. The needle assembly holder 365 has a proximal shaft 359 that runs through the side hole 254 of the lock bushing 318 and a proximal through hole 323 on the proximal wall of the housing 244. The lock spring retainer 258 is a threaded shaft threading into the matching threaded hole 321 on the housing 244 to hold the lock spring 257 in compression. By adjusting the position of the lock spring retainer 258 within the threaded hole 321, the compression force generated on the lock spring 257 varies. The lock spring 257 exerts an upward push force on the lock bushing 318, causing the side hole 254 of the lock bushing to move off alignment with the proximal through hole 323 of the housing 244. When this misalignment occurs, the proximal shaft 359 of the needle assembly holder 365 is locked within the side hole 254 of the lock bushing 318 and the proximal through hole 323 of the housing 244. The higher the compression force exerted by the lock spring 257 onto the lock bushing 318, the higher the locking force will be for the needle assembly holder. This locking mechanism locks the needle in either extended or retracted position preventing accidental needle movement. To release the lock, one can push on the top surface 256 of the lock bushing 318 downwards to align the side hole 254 with the proximal through hole 323 of the housing 244. This allows the needle assembly 109 to move freely.

In one embodiment, the needle assembly 109 includes the needle 138 supported by 1 or 2 layers of support tubes (not shown) such as stainless steel hypodermic tube(s) to enhance its rigidity and maintain straightness within the handle 200 and the second control mechanism 240. On the proximal end outside of the second control mechanism 240, the support tube (not shown) for the needle can be an elastic polymer tube acting as a strain relief for the unprotected needle. The injection port 204 has a standard luer connection compatible with standard syringe luer connectors.

In some applications, precise rotation response is a challenging performance criterion to achieve. Therapy such as local drug delivery to the infarct zone in the left ventricle of the heart requires predictable spatial dosing. Therefore, it is critical to be able to deliver the therapy tool, such as a needle, to multiple target sites within consistent spacing (e.g. 1 cm apart) from each other. The pull wire, under tension, brings one side of the catheter shaft into compression mode. This potentially creates shaft whipping resulting in uncontrolled catheter rotational movement.

The exemplary embodiments discussed below are referred to FIGS. 45-52, which describe a catheter assembly with multiple deflection direction. The embodiments allow the catheter assembly to deflect in multiple or all directions 360-degrees around the catheter shaft. This eliminates the need to turn the catheter shaft. The embodiments of FIGS. 45-52 provide in a catheter assembly that is easy to use and is capable of reaching all target locations within a 3D cavity with precise therapy dosing.

Figure 45:
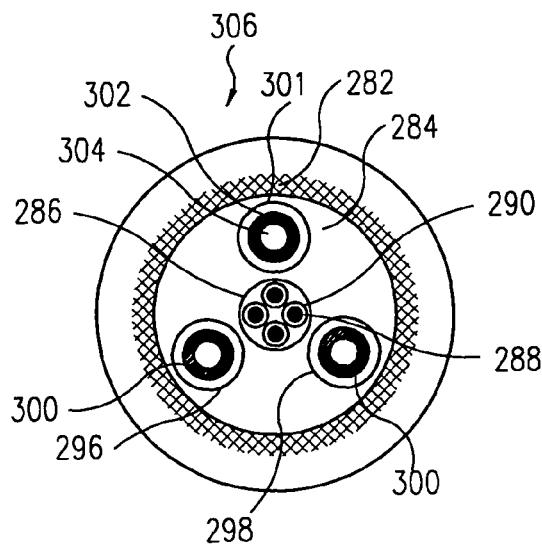
FIGS. 45-47 illustrate cross-sectional views of portions of a catheter assembly having multiple tendons.
Figure 49:
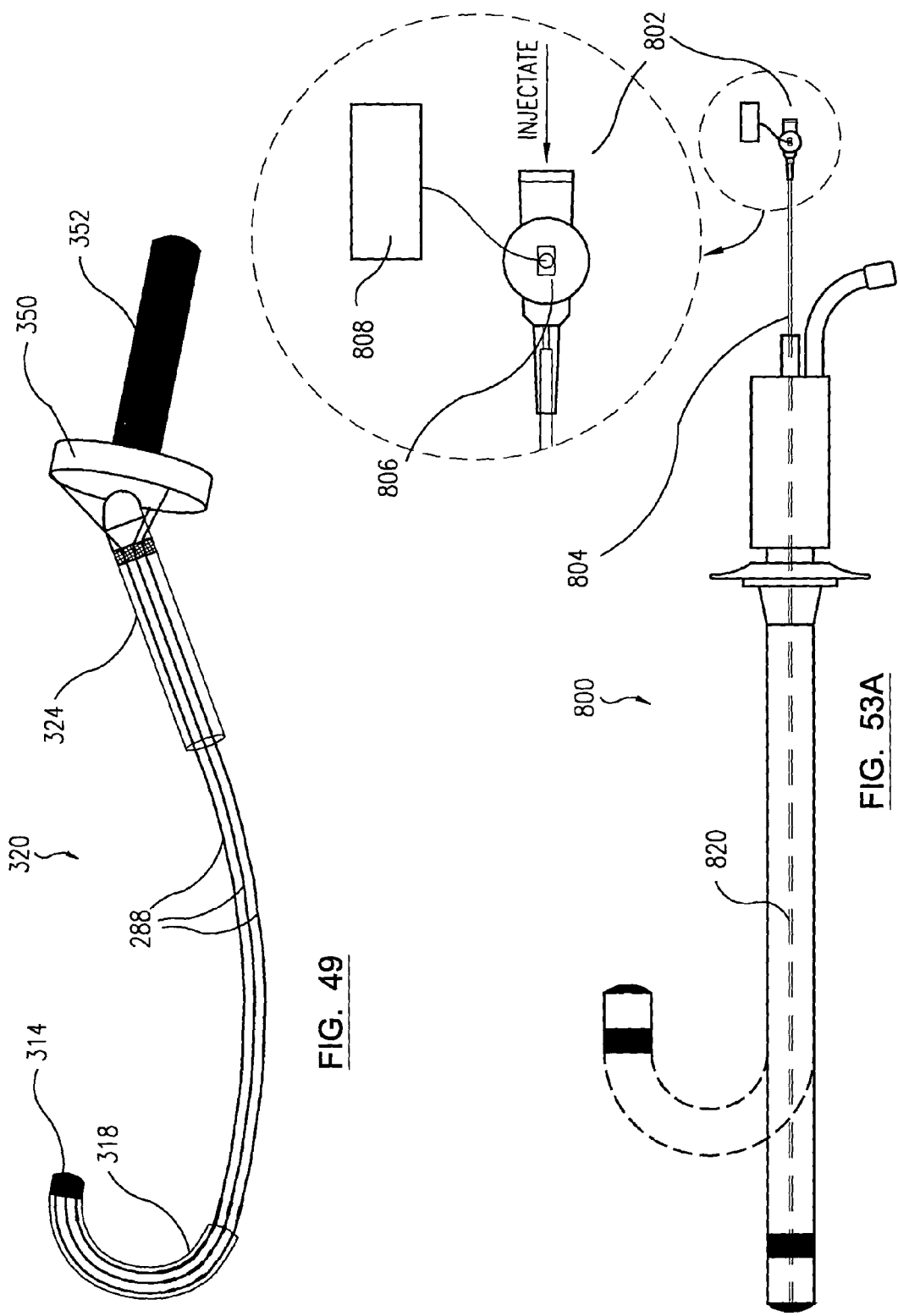
FIG. 49 illustrates an exemplary steering mechanism that can control multiple tendons.

In FIG. 45, a cross-section view of a catheter assembly 306 is illustrated. The catheter assembly 306 includes 4 tendons 288 and a needle 304. Although it is illustrated in FIG. 45 that the catheter assembly 306 includes 4 tendons 288, more or less tendon 288 may be used instead. For example, the catheter assembly 306 may include only 3 tendons 288 as shown in FIG. 49. The more tendons 288 are being used, the less force is required per tendon 288 to effect the same deflection, given all other factors being equal. The location of the tendons 288 relative to the plane of the shaft cross-section varies depending on the section of the shaft they are in. On the non-deflectable section, the catheter proximal section, the tendons 288 are located in the center of the catheter shaft. In one embodiment, the tendons 288 are disposed within a central lumen 286. Each of the tendons 288 may be disposed within a tendon sheath 290. In this embodiment, the tendon sheaths 290 are disposed within the central lumen 286. The needle 304 may be located in a lumen 301 away from the center. Alternatively, the needle 304 may be located in a central lumen 286 and free to move along side the tendon sheaths 290. The needle 304 may be disposed within a needle sheath 302. The construction of the tendons 288, the tendon sheath 290, the needle 304, and the needle sheath 302 are similar to previously described (for example, as in the catheter assembly 100).

In one embodiment, 2 additional lumens, 296 and 298, and lumen fillers 300 are included to help balance the moment or flexural properties of the catheter shaft of the catheter assembly 306 when the catheter shaft is in a curved conduit or vessel. The imbalance in the flexural properties can be caused by the lumen 301, the needle 304, and the needle sheath 302 depending on their relative orientation. The imbalanced flexural properties create a moment (a rotation) that tends to give the catheter shaft a preferred orientation relative to the curve's orientation, which is an effect that can cause whipping. The lumens 296 and 298 may be used for other purposes such as housing of a conductive wire if a tip electrode is placed at the catheter tip or for housing a second or third needle. The lumen 296 and 298 may also be filled with a lumen filler 300 if no additional components are to be included in the catheter assembly. A lumen support filler 284 made of a polymer extrusion may be present in the catheter shaft. The catheter shaft with the multiple lumens may be constructed using techniques previously described. The catheter shaft includes stiffening members 282 formed by a braid layer embedded inside of a polymer jacket.

Figure 46:
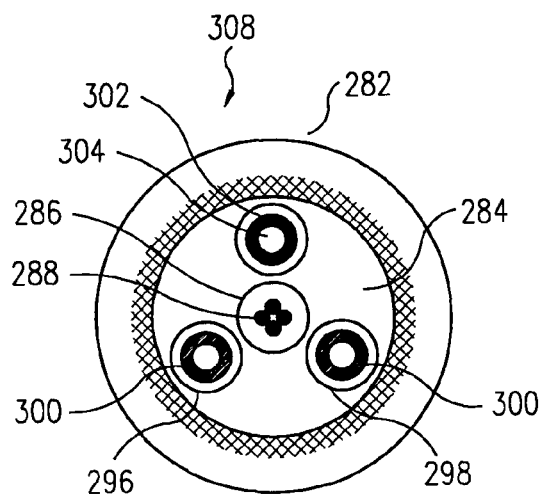

In FIG. 46, the catheter shaft is constructed as shown with 4 lumens: a lumen 286 for the tendons 288, a lumen 302 for the needle 304, and two other lumens, 296 and 298 filled with the lumen filler 300 to help balance the moment or flexural properties of the catheter shaft of the catheter assembly 306 when the catheter shaft is in a curved conduit or vessel. The embodiment shown in FIG. 46 removes the tubular members that house each of the tendons 288. The tendons 288 thus share a common lumen 286 that may be a lubricious inner surface to reduce friction for the tendons' movement. The tendons 288 may be further coated with a lubricious coating such as Teflon or Parylene coating material. This embodiment idea helps to reduce the profile of the catheter shaft.

It is likely that various therapies will require the injection of several different materials, solutions or mixtures that would be more effective if not mixed prior to injection. For instance, some approaches to injecting matrix material into an infracted zone to mechanically stiffen it and prevent dilatation could use substances of low viscosity which when mixed, react to form a much stiffer material. Another example would be the injection of cells. It is likely that growth factors or other materials that would facilitate the successful implantation of cells should not be mixed directly with the cells outside the body. Also using multiple needles allows a single device to provide different treatment materials to conveniently treat different areas of tissue. For instance, the treatment materials for an infarcted or scar tissue zone would very likely be different than those of a zone of stunned tissue. Additionally, these two lumens may be used to house additional members as needed. As can be seen in FIG. 45, depending upon the actual dimensions of the components, more than 3 lumens to accommodate needles or other members may be provided. Each of the pull wires is further housed inside of a tube with a lubricious inner surface, allowing for low friction movement.

Figure 47:
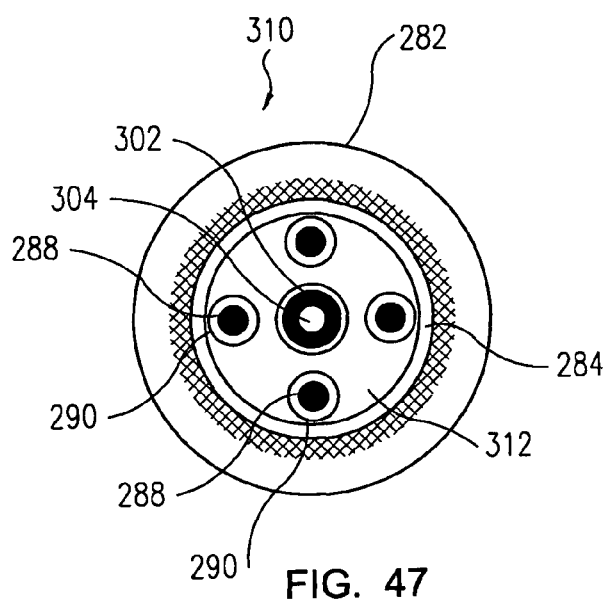

Both embodiments shown in FIGS. 45-46 may desire a flexurally balanced lumen and filler member to create a symmetrical cross section for optimal performance. FIG. 47 shows another embodiment in which all the components, the needle, the tendons 288, and their respective lumens forming member, are housed loosely inside of a central lumen 312. The needle 304 is house in a lumen 302 that is housed within the central lumen 312. This eliminates the need for a balancing lumen(s) and the filler member(s), but will induce proximal shaft deflection to a much greater degree than the cross-sections of FIGS. 45 and 46 due to the increased distance of the tendons 288 from the center of the catheter shaft (greater bending moment generated, all other factors being equal). This may increase catheter shaft whipping, if catheter shaft rotation is desired, and may result in increased catheter shaft tip motion during deflection (due to proximal shaft bending). The effects of this greater bending moment may be minimized by spiraling the tendons 288/tendon sheaths around lumen 302. This spiraling may induce a rotation that may cause the distal tip of the catheter shaft to twist during deflection. This rotation may be minimized by having equal spiraling lengths along the length of the proximal shaft in each direction (clockwise/counter clockwise), all other factors being equal.

Another embodiment is to have the tendons 288 located in the central lumen as per FIGS. 45 and 46. On the proximal shaft, the tendon sheath 290 can also be an axial spine, similar to catheter assembly 100 and 400. The needle may wrap around the tendons similar to catheter 400.

In another embodiment, the tendons 288 may wrap around each other within the axial spine lumen in the proximal section of the catheter shaft. By wrapping the tendons 288 together, any outstanding moment generated by the tendon(s) in tension is balanced.

Figure 48:
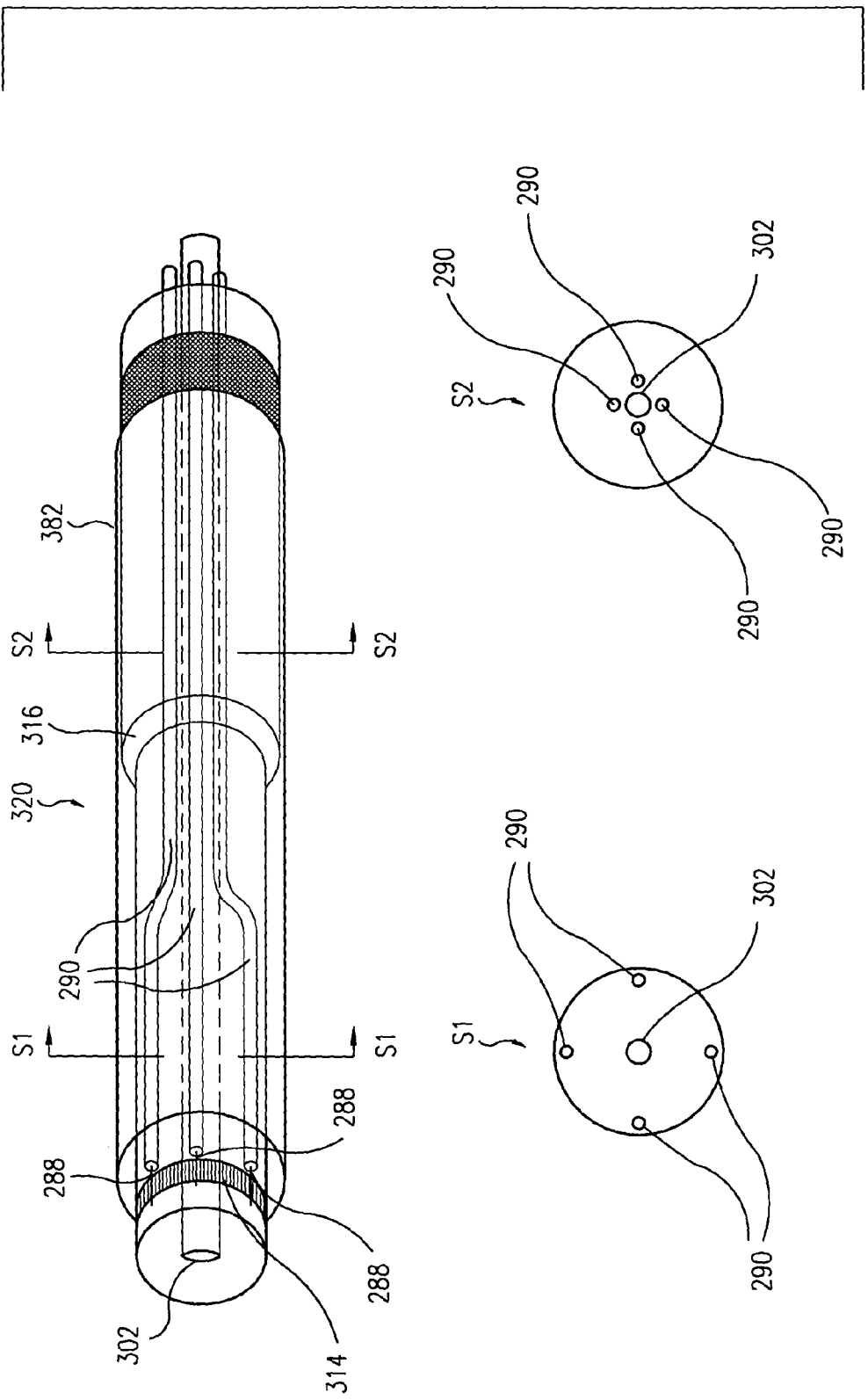
FIG. 48 illustrates a catheter assembly having multiple tendons.

In FIG. 48, (including 51 and 52), on the deflectable section of the catheter shaft, the tendons 288 are placed off center to create a pull force toward the direction of deflection. The tendons 288 are placed at about 90-degrees from each other. In one embodiment, the tendons 288 continue to be housed inside of a lumen until they reach the distal anchor point 314. At the anchor point 314, the tendons 288 are attached to a band, by means of welding, soldering, mechanical trapping, or adhesive bonding, still separated apart radially at 90-degrees away. It is optimum for the tendons 288 to be placed at equal angles from each other. In the embodiments where there are 4 tendons 288 included in the catheter assembly 306, each tendon 288 is placed at about 90-degrees away from each other. In the embodiments where there are 3 tendons 288 included in the catheter assembly 306, each tendon 288 is placed at about 120-degrees away from each other. In another embodiment, each tendon 288 is placed in parallel to another tendon 288 and at about 180-degrees away from each other. The needle lumen continues in the central lumen 302 (or is brought to the center if the non-deflectable shaft is constructed by the method shown in FIGS. 45-46 where the tendons 288 are placed at the center and the needle is placed off-center of the catheter shaft at the catheter proximal section. As can be visualized, when one of the tendons 288 is pulled, the deflectable section will deflect towards the direction of the one tendon 288 location. If two tendons 288 are pulled, the deflection will occur in the direction between the locations of the two tendons 288. In one embodiment, when the two tendons 288 are pulled, the two tendons 288 should be brought together side-by-side so that the tension force on both tendons 288 will not cancel each other and pulling on the two tendons 288 will result in a direction between the locations of the two tendons 288.

As one can imagine, this concept of multiple directional steering can be achieved with 3 pull wires as well. Dependent on the design of the proximal catheter handle, the number of deflection directions radially may equal to the number of tendons 288, or double the number of the tendons 288, or without limit along a circular path around the shaft. For optimal result, a minimum of 3 tendons 288 is required and more tendons 288 may be used. As previously mentioned, the more tendons 288, the less force is required per tendon 288 to effect the same deflection.

Below are descriptions for a catheter handle that can be used for the catheter assembly 306 that have multiple tendons 288.

In one embodiment, each tendon 288 is coupled to a pull knob (not shown) on a handle (e.g., a catheter handle 200). Each tendon 288 can be pulled independently and only one tendon 288 is allowed to pull at any instance. As a result, the catheter can now deflect in the number of directions equal to the number of tendons 288. Alternatively, each tendon 288 may be pulled independently and 2 adjacent tendons 288 may be pulled at the same time. In such an embodiment, the catheter shaft of the catheter assembly 306 will deflect in a direction between that of the adjacent tendons 288 and the deflection direction will be related to the ratio of the amount of tendon translation applied. In this way, any deflection direction (360 degree deflection directions) may be attained. For example, in one embodiment, two tendons 288 are included and in this embodiment, there can be at least two directional deflections. In another embodiment, three tendons 288 are included and in such embodiment, there can be at least three directional deflections.

Alternatively, a way to attain more deflection directions is to couple the tendons 288 to a steering plated 350 at equal angles and distances from the steering plate 350 center as shown in a simplified drawing in FIG. 49. Each of the tendons 288 passes through a catheter handle 324 that couples to the steer plate 350 which may include a steering handle 352. The steer plate 350 is being tilted (e.g., via the steering handle 352) away from the tendon 288 attachment location or away from two adjacent tendons 288 attachments. This automatically adjusts the applied tendon 288 translations such that any angle of deflection may be obtained. Each tilt angle and adjacent tilt angle of the steering plate 350 corresponds to a different and adjacent shaft deflection angle. The greater the tilt, the greater the catheter shaft will deflect.

Figure 50:
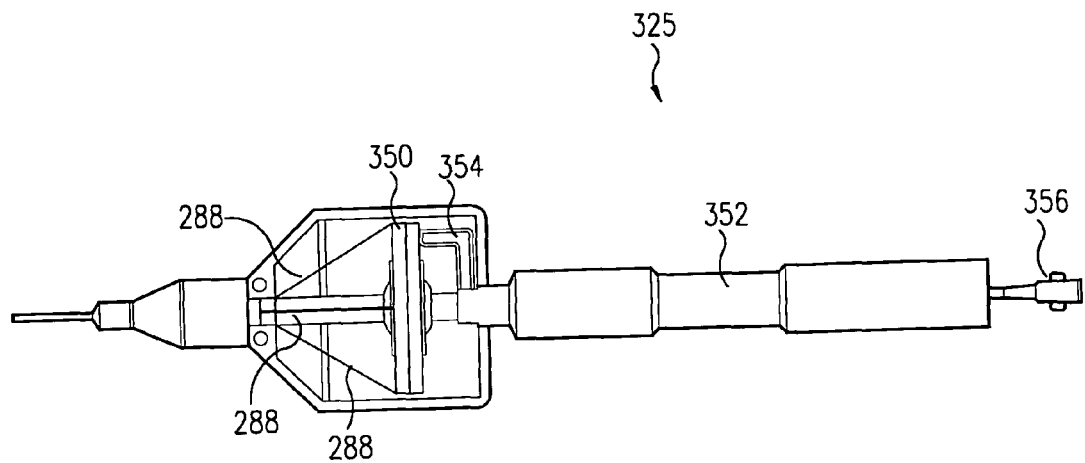
FIGS. 50-52 illustrate an exemplary control mechanism that can control multiple tendons in a catheter assembly.
Figure 51:
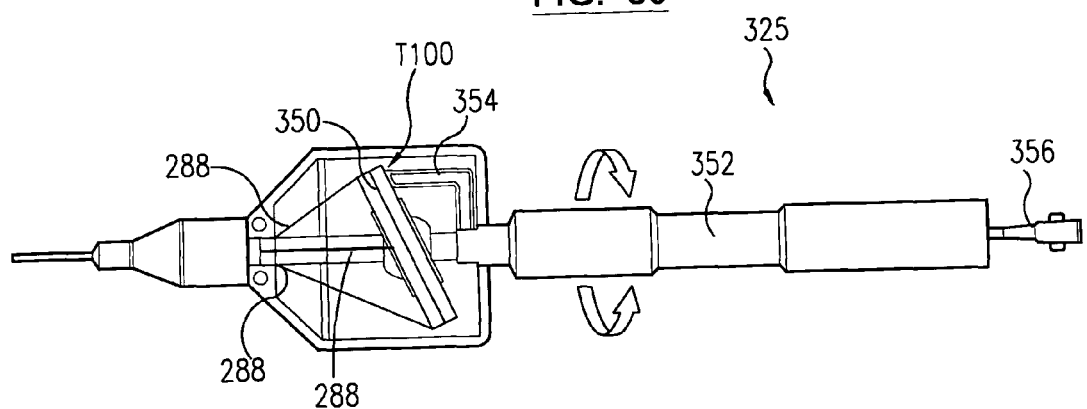
Figure 52:
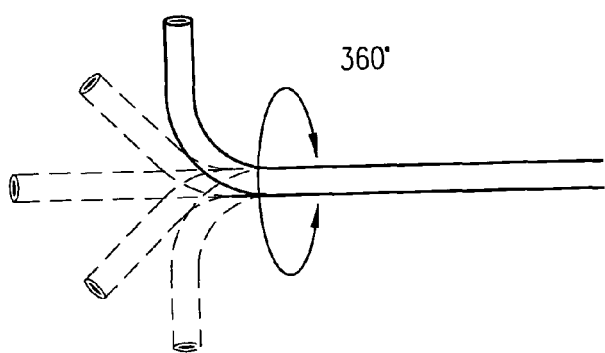

FIG. 50 shows a catheter handle 325 that can provide the catheter assembly having multiple tendons 288 with multiple deflection direction. The catheter handle 325 comprises a push arm 354, a steering plate 350, and a steering handle 352. The push arm 354 functions to tilt the steering plate 350 at any location along a circular path of the steering plate 350. In one embodiment, the push arm 354 is an L-shape push arm. In FIG. 51, the push arm 354 is pushed forward which causes it to tilt the steering plate 350 at a point $T_{100}$ along the circular path of the steering plate 350. A tendon 288 that is attached to the steering plate 350 at this point $T_{100}$ is then pushed forward. A tendon 288 that is opposite the point $T_{100}$ is pulled backward. The push arm 354 moves forward to tilt the steering plate 350, creating tension on the tendon 288 attached in the opposite direction. As a result, the catheter deflects. The distal end of the catheter shaft can be deflected accordingly. The push arm 354 can be rotated in any direction to tilt the steering plate 350 at any point. By rotating the push arm 354 around, the deflection direction changes. The user can now search for the desirable deflection direction by rotating the steering arm 352, which rotates the push arm 354. Pulling the push arm 354 back will allow the steering plate 350 to return to its normal perpendicular (to the shaft) position and the deflectable section straightens. FIG. 52 shows a deflectable distal section with unlimited deflection direction. The deflectable section can just sweep around 360-degrees by the control of the handle 325.

A multi-directional steering needle injection catheter has been described in the above exemplary embodiments. The concept can be varied to give rise to other functions that may have other therapeutic benefits. Examples of these variations are given below.

The embodiments described with respect to FIGS. 45-52 can be varied to add more flexibility to the deflection direction. In one embodiment, each or some of the tendons 288 may be configured to be adhered to a different location along the catheter distal section. When a tendon 288 is adhered (at its distal tip) to a location more distal along the catheter shaft, the deflection radius will be smaller when that particular tendon 288 is pulled thus, giving a shorter curve. This may benefit use of a catheter assembly in a tight cavity space. When a tendon 288 is adhered (at its distal tip) to a location more proximal along the catheter shaft, the deflection radius will be larger when that particular tendon 288 is pulled, thus, giving a larger curve. The larger radius will also allow for reaching a far wall, such as the lateral wall in an infarcted and enlarged heart, in a heart cavity. In addition, the deflection will be allowed to have an approximately 180-degrees deflection.

In one embodiment, a fluid pressure sensor system is incorporated into a catheter assembly to allow for a detection of needle penetration depth. This concept has been disclosed in a co-pending application by Dagmar Beyerlein, entitled "Systems and Methods for Detecting Tissue Contact and Needle Penetration Depth," having application Ser. No. 10/166,854, which was filed Jun. 10, 2002 and a co-pending application by Dagmar Beyerlein, entitled "Systems and Methods for Detecting Tissue Contact and Needle Penetration Depth Using Static Fluid Pressure Measurements," which is a continuation-in-part of application Ser. No. 10/166,854, which was filed Sep. 5, 2003. Both of these applications are herein incorporated by reference in their entirety.

In one embodiment, the catheter assembly, which could be any of the catheter assemblies (e.g., 100, 400, or 500) previously described, has a fluid pressure transducer integrated in line with the needle fluid column near the proximal needle injection port. The needle is filled with an injection fluid. By monitoring the static pressure of the fluid column and/or injection pressure with a small test injection volume, the needle penetration depth can be detected.

FIG. 53A illustrates an exemplary embodiment where a fluid pressure transducer 802 is incorporated into a catheter assembly 800. As should be understood, the catheter assembly 800 can be similar to any one of the catheter assemblies 100, 400, or 500 previously described. The fluid pressure transducer 802 is integrated into the proximal injection port 804 in line with the fluid injection path of the catheter assembly 800. In one embodiment, the fluid pressure transducer 802 is mounted on the injection port 804. In alternative embodiment, the fluid pressure transducer 802 is mounted with a thin highly compliant membrane 806 separating the incoming fluid from the transducer circuitry (not shown).

Figure 53B:
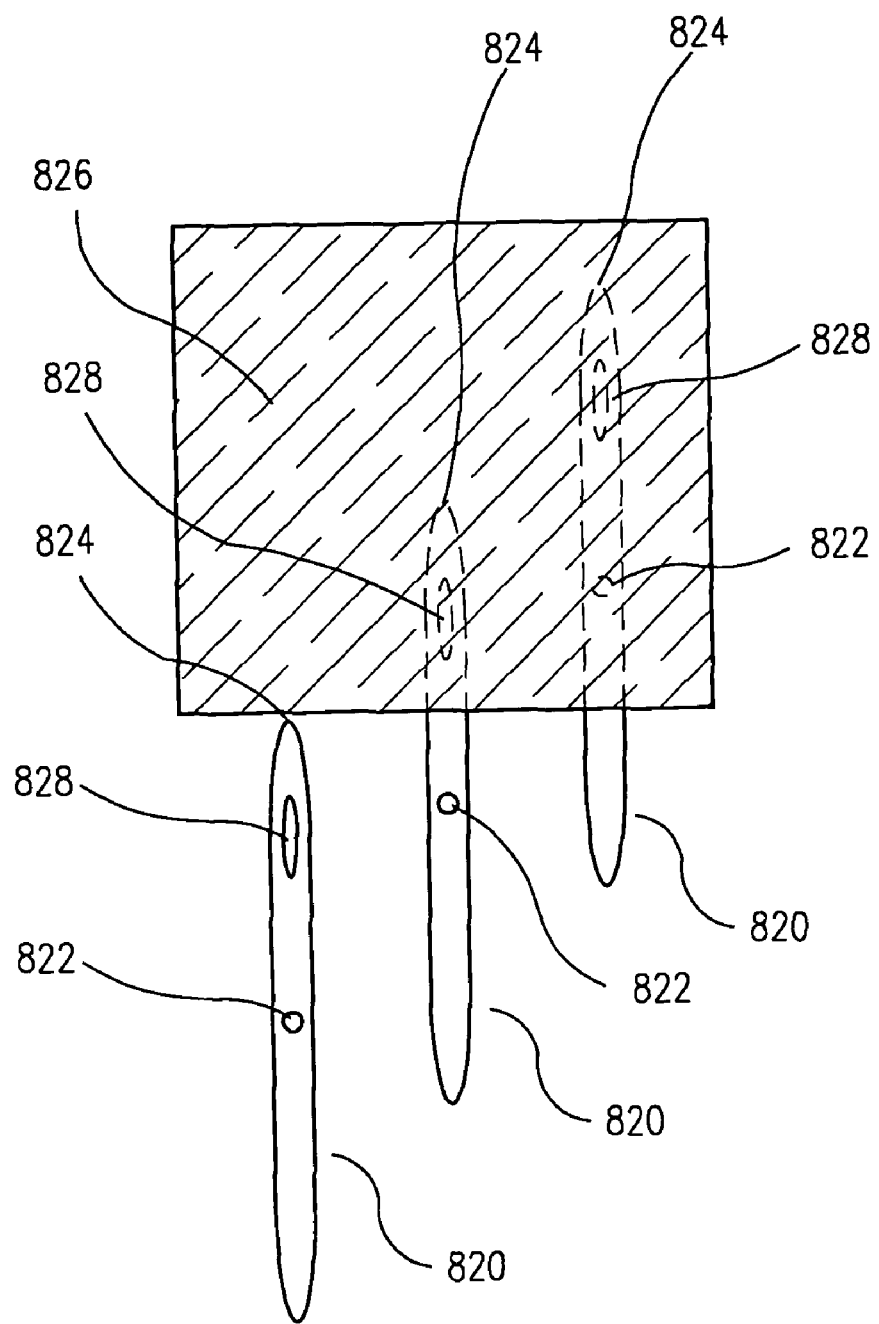

In general, the catheter assembly 800 includes a needle 820 and a fluid pressure measurement assembly or the pressure transducer 802 (FIG. 53A). The needle 820, in one exemplary embodiment, includes a first end and a second end with at least one aperture 822 located a predetermined distance from the first end (FIG. 53B). Except for the addition of the aperture 822, the needle 820 can be similar to the needles previously described in other embodiments. The pressure measurement assembly is connected with a portion of the needle 820 to measure the dynamic injection or static pressure of fluid dispensed through the needle 820. The pressure measurement assembly measures the changes in pressure as the needle 820 is advanced into tissue. The changes in pressure are caused by the compression of the fluid by the tissue. The fluid pressure measurement assembly measures a first pressure with the fluid dispensed in the needle 820, a second pressure when the needle 820 contacts tissue 826 and the lumen 828 at the needle tip 824 becomes occluded by the tissue 826, and a third pressure when the needle 820 penetrates deeper in the tissue 824 and the aperture 822 becomes occluded by the tissue 826. Several apertures 833 can be included for various penetration depth determinations.

In one exemplary application of the catheter assembly 800 that incorporates the pressure transducer 802, the catheter is used to inject a bio-agent to the myocardium from inside the left ventricle of a patient. The following pressure levels are exemplary pressure levels that can be detected based on the needle penetration depth.

First, when the needle 820 is retracted in the catheter within the left ventricle cavity and/or without any needle penetration into the myocardium, the pressure detected is a ventricular pressure waveform, such as a fluctuating pressure between 10 mmHg to 120 mmHg at the rate of the cardiac cycle (pressure levels dependent on the heart's physical and contractile conditions). In one embodiment, a first injection pressure as a result of a continuous injection volumetric rate is measured. The first injection pressure will be low. In another embodiment, the needle 820 is filled with a desired fluid and the initial (first) pressure of the static fluid is measured. The first pressure is measured with the fluid dispensed in, but not flowing through the needle. The first pressure will also be low.

Second, when the needle 820 is fully penetrated into the myocardium, the needle tip lumen 828 is fully occluded by the myocardial tissue; the detected pressure will be a relatively static pressure (without the fluctuations tied to the cardiac cycle). In one embodiment, a second injection pressure, as a result of the same continuous injection volumetric rate above is measured. The second injection pressure will be increased (compared to the first injection pressure). In another embodiment, a second pressure of the fluid column dispensed (but not flowing) in the needle is measured when the needle tip lumen 828 is fully occluded by the myocardial tissue. The second pressure of the fluid will be increased compared to the first pressure of the fluid column.

Third, when the aperture 822 penetrated into the myocardium, the injection pressure or alternatively, the pressure of the fluid will be increased. In one embodiment, a third injection pressure, as a result of the same continuous injection volumetric rate above is measured. The third injection pressure occurs when the aperture 822 is occluded by the myocardial tissue. The third injection pressure will be increased compared to the second injection pressure. In another embodiment, a third pressure of the fluid column dispensed (but not flowing) in the needle is measured when the aperture 822 is occluded by the myocardial tissue. The third pressure of the fluid column will be increased compared to the second pressure of the fluid column.

The fluid pressure measurement assembly also allows for further detection of the needle 820 penetration depth. For instance, in some cases, the needle 820 may penetrate beyond the myocardium. In one embodiment, the needle 820 penetrates into an arterial vessel from the myocardium. When the needle tip penetrates into an arterial vessel, an arterial pressure waveform will be detected. This waveform will not reach as low a pressure as the waveform detected in the ventricle cavity, a typical minimum pressure may be in the range of 60-80 mmHg. In one embodiment, a fourth injection pressure, as a result of the same continuous injection volumetric rate above is measured. The fourth injection pressure will be higher than the second injection pressure. In another embodiment, a fourth pressure of the fluid column dispensed (but not flowing) in the needle is measured when the needle tip penetrates into the arterial vessel. The fourth pressure will be higher than the second pressure.

In another embodiment, the needle 820 may penetrate a vein and when the needle tip penetrates into a vein, the pressure detected will be relatively static with a lower mean value than either the arterial or ventricular mean pressure. In one embodiment, a fifth injection pressure, as a result of the same continuous injection volumetric rate above is measure. The fifth injection pressure will be lower than the first injection pressure and lower than the fourth injection pressure. In another embodiment, a fifth pressure of the fluid dispensed (but not flowing) in the needle is measured when the needle tip penetrates into the vein. The fifth pressure will be lower than the first pressure and lower than the fourth pressure.

In yet another embodiment, the needle 820 may penetrate too far into the pericardial space or through the pericardial sac, outside of the heart. In such an embodiment, the detected pressure will be static (and/or tied the ventilation rate) and the lowest of all situations. Similarly, the injection pressure, as a result of the same continuous injection volumetric rate above, will be also low. Alternatively, the pressure of the fluid dispensed in the needle (but not flowing) will also be lowest of all situations.

These different pressure levels, which may be expressed in wave forms, can be displayed on a display unit 808 or it can be programmed into different audible signals. The indications of the various pressure levels (e.g., injection pressure or static fluid pressure) will allow for the monitoring of the penetration depth of the needle. Before injection, the operator will check the pressure output to ensure appropriate needle depth location and needle penetration. If the needle is penetrated too far or penetrated into a blood vessel, the proximal needle stop can be adjusted to allow for change of needle position. Further details of the pressure sensing system can be found in the referred and entirely incorporated applications previously mentioned.

In any of the embodiments previously describe, the catheter shaft of the catheter assembly may include radiopaque markers or have portions of the catheter shaft made out of radio-opaque markers to facilitate in the monitoring and/or locating of the catheter shaft inside a patient. In one embodiment, a radio-opaque powder is mixed into polymers used for all of the outer jackets of the catheter shaft to make the catheter visible under fluoroscope. In other embodiments, a radio-opaque powder is mixed into polymers used for the catheter guide sheath that is used to guide the catheter shaft into the patient's body. Examples of radio-opaque powder include bismuth subcarbonate, also called bismuth oxycarbonate, barium sulfate, and tungsten. The radio-opaque materials typically come in powder form and are used as a radio-opaque salt compounded with other polymer to make radio-opaque polymer.

Figure 54:
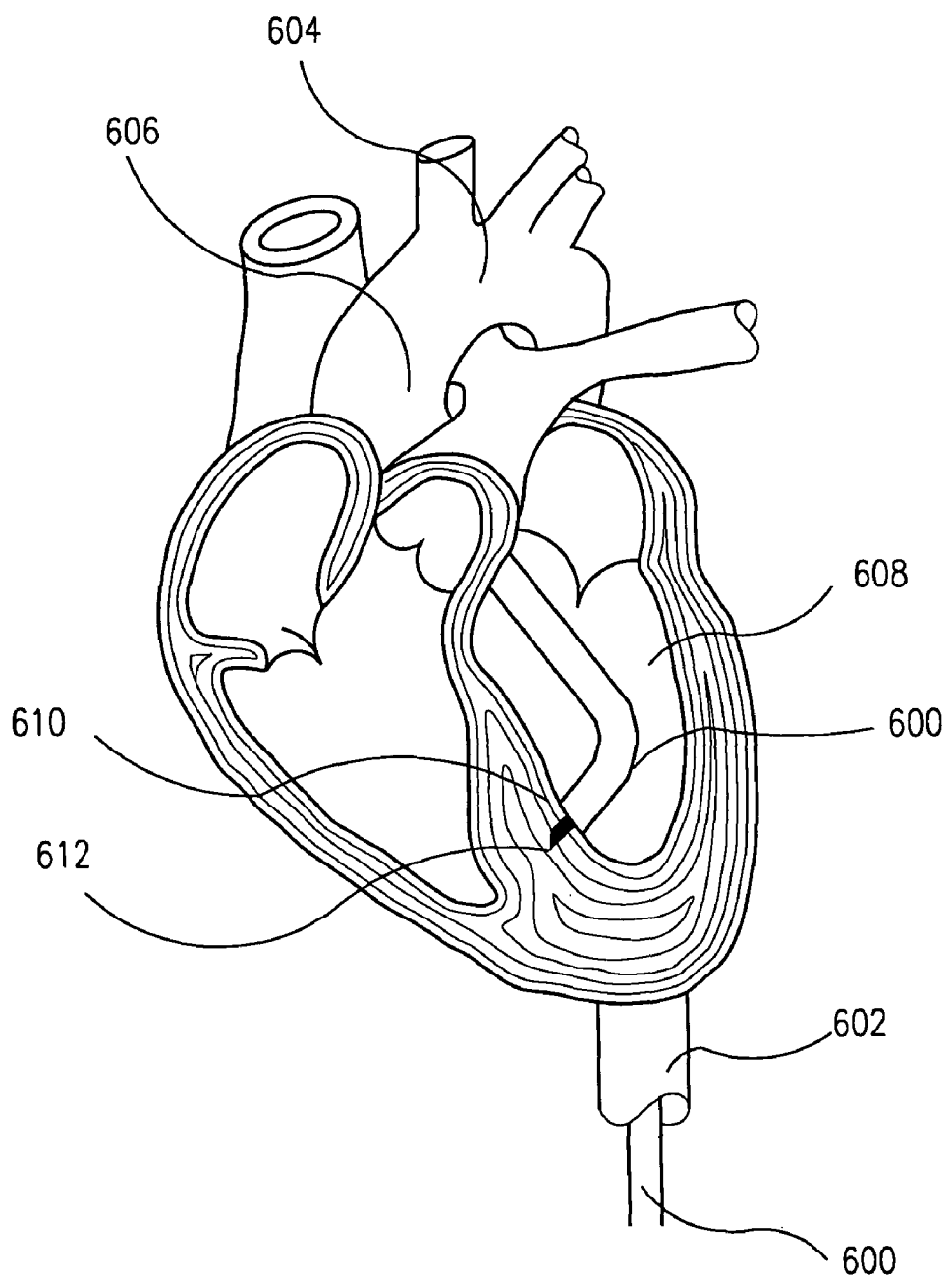
FIG. 54 illustrates an exemplary method of delivering one of the exemplary catheter assemblies of the present invention into the heart.

FIG. 54 illustrates an exemplary procedure that uses one of the catheter assemblies (e.g., 100) previously described. In one embodiment, a catheter assembly 600 is used to deliver an agent into the left ventricle of a patient. The catheter assembly 600 can be anyone of the catheter assemblies previously described.

The catheter assembly 600 is inserted into the femoral artery in the groin region (not shown) through an access path created by a percutaneously placed introducer sheath as is well known in the art. The catheter assembly 600 travels into the descending aorta artery 602, over the aortic arch 604, down the ascending aorta 606, across the aortic valve (not shown) and into the left ventricle 608.

Target injection sites (e.g., a target injection site 610) have been determined prior to the delivery procedure. The operator manipulates the catheter assembly 600 to each target 610 location. The manipulation is done by motions of sliding the catheter assembly 600 up and down the ventricle 608 cavity, rotating the catheter assembly 600 to reach different targets in the radial directions (e.g., anterior, lateral, septal wall), and deflecting the catheter distal section to reach the wall. Deflection of the catheter distal section is activated by pulling the outer housing of the catheter handle (as previously described) away from the distal adapter of the catheter handle. The outer housing carries the tendon holder toward proximal direction, which pulls the tendon of the catheter assembly 600 in tension. Once the catheter tip is in contact with the target wall, the operator holds the catheter assembly 600 steady, extends the needle 612 of the catheter assembly 600 to the pre-set needle stop, injects a prescribed dose of bio-agent, retracts the needle 612 and moves the catheter assembly 600 to another target location. The contact of the catheter assembly 600 with the ventricular wall can be easily identified. The catheter tip will be seen bouncing with the wall at every contraction cycle and the EKG signal will also change. When the procedure is complete, the catheter is withdrawn from the vasculature.

The needles of the embodiments of the disclosure can be used to deliver a wide range of therapeutic agent or biologic such as cells, drugs, or other fluids. For examples, biological agents such as growth factors (endothelial growth factor (VEFG) and fibroblast growth factors (FGF)), angiogenic agents (angiostatin and endostatin), cells (myogenic cells, bone marrow derived stem cells, endothelial cells, cardiomyocytes), genetic materials (DNA, RNA (virus or other vector based), and iRNA), biochemical agents, small molecule agents, and/or any combination of the above agents, can be delivered using the needles included in the catheter assemblies previously described.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the scope of this invention.

We claim:

1. A deflectable catheter assembly comprising:
a catheter shaft having a catheter proximal section and a catheter distal section, the catheter distal section defining a length, said catheter distal section being more flexible than said catheter proximal section and said catheter proximal section having a length greater than that of the catheter distal section;
a tendon disposed within a first lumen of said catheter shaft, said tendon being approximately centrally located within said catheter shaft along an entire length of said catheter proximal section and said first lumen located off-center of said catheter shaft at said catheter distal section, wherein deflection of the tendon deflects said catheter distal section without modifying the catheter distal section length;
a needle disposed within a second lumen of said catheter shaft, said second lumen being located off-center within said catheter shaft at said catheter proximal section and said second lumen approximately centrally located within said catheter shaft at said catheter distal section; and
a catheter handle coupled to said catheter shaft, said catheter handle including a first control mechanism to control said tendon.

2. A deflectable catheter assembly as in claim 1 comprising a plurality of needles each of which is disposed within said second lumen of said catheter shaft.

3. A deflectable catheter assembly as in claim 1 further comprises,
an axial spine disposed around and over a first section of said tendon, said first section being substantially aligned with said catheter proximal section, said axial spine to resist axial compression along said catheter proximal section.

4. A deflectable catheter assembly as in claim 1 further comprises,
an axial spine disposed around and over a first section of said tendon, said first section being substantially aligned with said catheter proximal section, said axial spine to resist axial compression along said catheter proximal section; and
a flexible tendon sheath coupling to said axial spine, said flexible tendon sheath extending a second section of said tendon and said second section being substantially aligned with said catheter distal section.

5. A deflectable catheter assembly as in claim 1 wherein said tendon comprises,
an axial spine disposed over a first section of said tendon, said first section being substantially aligned with said catheter proximal section of said catheter shaft, said axial spine to resist axial compression along said catheter proximal section;
a first plurality of slip bands disposed around a distal section of said axial spine;
a second plurality of slip bands disposed around a proximal section of said axial spine; and
a flexible tendon sheath coupling to said axial spine, said flexible tendon sheath extending a second section of said tendon and said second section being substantially aligned with said catheter distal section.

6. A deflectable catheter assembly as in claim 1 further comprising:
a tip electrode located at the tip of said catheter distal section and coupled to a conductive lead that extends out of said catheter shaft.

7. A deflectable catheter assembly as in claim 1 further comprising:
a tip electrode located at the tip of said catheter distal section and coupled to a conductive lead that extends out of said catheter shaft; and
at least one additional electrode located proximally along said catheter distal section and closely to said tip electrode, said at least one additional electrode coupled to another conductive lead that extends out of said catheter shaft, wherein said tip electrode and said at least one additional electrode forming a bipolar electrode system.

8. A deflectable catheter assembly as in claim 1 further comprising:
a tip electrode located at the tip of said catheter distal section and coupled to a conductive lead that extends out of said catheter shaft;
wherein said tip electrode having an opening to allow said needle to pass therethrough, and
wherein said catheter handle includes a second control mechanism to control said medical device.

9. A deflectable catheter assembly as in claim 8 further comprising:
at least one additional electrode located proximally along said catheter distal section and closely to said tip electrode, said at least one additional electrode coupled to another conductive lead that extends out of said catheter shaft, wherein said tip electrode and said at least one additional electrode forming a bipolar electrode system.

10. A deflectable catheter assembly as in claim 8 wherein said tip electrode is exposed only at a surface section of said catheter shaft proximate to where said needle exits said catheter shaft to reach a target site.

11. A deflectable catheter assembly as in claim 10 further comprising:
at least one additional electrode located proximally along said catheter distal section and closely to said tip electrode, said at least one additional electrode coupled to another conductive lead that extends out of said catheter shaft, wherein said tip electrode and said at least one additional electrode forming a bipolar electrode system.

12. A deflectable catheter assembly as in claim 1 further comprising:
a tip electrode located at the tip of said catheter distal section and coupled to a conductive lead that extends out of said catheter shaft; and
at least one additional electrode located proximally along said catheter distal section, said at least one additional electrode buried beneath a surface of said catheter distal section and coupled to another conductive lead that extends out of said catheter shaft, wherein said catheter distal section includes an opening to expose said at least one additional electrode, and wherein said tip electrode and said at least one additional electrode forming a bipolar electrode system.

13. A deflectable catheter assembly as in claim 1 wherein said catheter proximal section is further divided into a middle catheter proximal section and a catheter proximal section wherein said middle catheter proximal section is more flexible than said catheter proximal section.

14. A deflectable catheter assembly as in claim 1 wherein catheter proximal section is further divided into a middle catheter proximal section and a catheter proximal section wherein said middle catheter proximal section is more flexible than said catheter proximal section and is less flexible than said catheter distal section.

15. A deflectable catheter assembly as in claim 1 wherein said first control mechanism includes a tendon control mechanism that deflects or relaxes a tendon included in said tendon to deflect said catheter distal section and wherein a second control mechanism is included in said catheter handle to control said needle.

16. A deflectable catheter assembly as in claim 1 further comprising:
a pre-shaped guide sheath disposed around said catheter shaft and extending from said catheter distal section to said catheter proximal section, said pre-shaped guide sheath being able to facilitate the maneuvering of said catheter shaft through tortuous pathways.

17. A deflectable catheter assembly as in claim 1 further comprising:
a pre-shaped guide sheath disposed around said catheter shaft and extending from said catheter distal section to said catheter proximal section, said pre-shaped guide sheath having at least one angular bend at a distal end to facilitate the maneuvering of said catheter shaft through tortuous pathways.

18. A deflectable catheter assembly as in claim 1 further comprising:
a pre-shaped guide sheath disposed around said catheter shaft and extending from said catheter distal section to said catheter proximal section, said pre-shaped guide sheath having a dual-angular bend at a distal end to facilitate the maneuvering of said catheter shaft through tortuous pathways.

19. A deflectable catheter assembly as in claim 1 wherein said needle is disposed within a needle tube, said needle tube disposed within said second lumen of said catheter shaft, said needle and said needle tube being extendable from and retractable into said catheter distal section and said needle being extendable from and retractable into said needle tube.

20. A deflectable catheter assembly as in claim 1 further comprises a plurality of needle assemblies, disposed within said second lumen of said catheter shaft, each of said plurality of needle assemblies being extendable from and retractable into said catheter distal section.

21. A deflectable catheter assembly as in claim 1 comprises a plurality of needles, each of said plurality of needles being disposed within a needle tube, each of said needle tubes disposed within said second lumen of said catheter shaft, each of said plurality of needles and said needle tubes being independently extendable from and retractable into said catheter distal section and each of said plurality of needles being independently extendable from and retractable into each of said needle tubes.

22. A deflectable catheter assembly as in claim 1 comprises a plurality of needles and at least one inflatable balloon coupling to said plurality of needles, said inflatable balloon, when inflated, directs said plurality of needles to desired target sites.

23. A deflectable catheter assembly as in claim 1 wherein said needle comprises a divergent angle disposed within a needle tube, said needle tube disposed within said second lumen of said catheter shaft, said at least one needle and said needle tube being extendable from and retractable into said catheter distal section and said needle being extendable from and retractable into said needle tube.

24. A deflectable catheter assembly as in claim 1 wherein said needle comprises a plurality of injection openings disposed within a needle tube, said needle tube disposed within said second lumen of said catheter shaft, said at least one needle and said needle tube being extendable from and retractable into said catheter distal section and said at least one needle being extendable from and retractable into said needle tube.

25. A deflectable catheter assembly as in claim 1 further comprises a needle stop mechanism to control the travel distance of said needle.

26. A deflectable catheter assembly as in claim 1 further comprises a pressure sensor system coupling to said needle, said pressure sensor allows for fluid pressure measurements to indicate penetration depth for said needle.

27. A deflectable catheter assembly as in claim 26 wherein said needle includes a first end and a second end, said needle further having at least one aperture located a predetermined distance from the first end and said pressure sensor system coupled with a portion of said needle to measure pressure of a fluid dispensed in said needle, said pressure measurement assembly measuring a first pressure with said fluid dispensed in said needle, a second pressure when said needle contacts tissue before said aperture becomes occluded and a third pressure as said needle penetrates tissue and said aperture becomes occluded.

28. The catheter assembly of claim 1 wherein the needle is made of a polymer material.

29. A deflectable catheter assembly comprising:
   a catheter shaft having a catheter proximal section fixed directly to a catheter distal section, said catheter distal section being more flexible than said catheter proximal section and said catheter proximal section having a length greater than that of the catheter distal section;
   a tendon disposed within a first lumen of said catheter shaft, said tendon being fixed axially at an approximately central location within said catheter shaft along an entire length of said catheter proximal section and said first lumen fixed axially at a location off-center of said catheter shaft at said catheter distal section, said tendon being able to deflect said catheter distal section when being pulled on without modifying a length of the catheter shaft;
   a needle disposed within a second lumen of said catheter shaft, said second lumen being fixed axially at a location off-center within said catheter shaft at said catheter proximal section and said second lumen fixed axially at an approximately central location within said catheter shaft at said catheter distal section; and
   a catheter handle coupled to said catheter shaft, said catheter handle including a first control mechanism to control said tendon.

* * * * *